(12) United States Patent
Ying et al.

(10) Patent No.: US 12,215,123 B2
(45) Date of Patent: Feb. 4, 2025

(54) CORDYCEPIN-BASED DERIVATIZED COMPOUND WITH ANTI-TUMOR EFFECT

(71) Applicant: NANJING TECH UNIVERSITY, Nanjing (CN)

(72) Inventors: Hanjie Ying, Nanjing (CN); Tao Shen, Nanjing (CN); Chenglun Tang, Nanjing (CN); Dong Liu, Nanjing (CN); Yong Chen, Nanjing (CN); Chenjie Zhu, Nanjing (CN); Pengpeng Yang, Nanjing (CN); Wei Zhuang, Nanjing (CN)

(73) Assignee: NANJING TECH UNIVERSITY, Nanjing (CN)

( * ) Notice: Subject to any disclaimer, the term of this patent is extended or adjusted under 35 U.S.C. 154(b) by 0 days.

(21) Appl. No.: 18/505,822

(22) Filed: Nov. 9, 2023

(65) Prior Publication Data

US 2024/0116976 A1    Apr. 11, 2024

Related U.S. Application Data

(63) Continuation of application No. PCT/CN2023/099859, filed on Jun. 13, 2023.

(30) Foreign Application Priority Data

Jul. 12, 2022 (CN) .......... 202210818492.X

(51) Int. Cl.
| | | |
|---|---|---|
| C07H 19/20 | (2006.01) | |
| A61P 35/00 | (2006.01) | |
| C07H 19/173 | (2006.01) | |

(52) U.S. Cl.
CPC .............. C07H 19/20 (2013.01); A61P 35/00 (2018.01); C07H 19/173 (2013.01)

(58) Field of Classification Search
None
See application file for complete search history.

(56) References Cited

FOREIGN PATENT DOCUMENTS

| | | | |
|---|---|---|---|
| CN | 101574362 A | 11/2009 | |
| CN | 102395590 A | 3/2012 | |
| CN | 107207554 A | 9/2017 | |
| CN | 110049767 A | 7/2019 | |
| WO | WO-2016083830 A1 * | 6/2016 | ......... A61K 31/7076 |
| WO | 2017165489 A1 | 9/2017 | |
| WO | 2018208727 A1 | 11/2018 | |

OTHER PUBLICATIONS

Alimohammadi, International Journal of Nanomedicine 2020: 15, 5279-5288. (Year: 2020).*
Lipson, Clin Cancer Res; 17(22) Nov. 15, 2011. (Year: 2011).*
Ondrej Pav etc.,Activation of human RNase L by 2'- and 5'-O-methylphosphonate-modified oligoadenylates Bioorganic Medicinal hemistry Letters, vol. 22 p. 181-185 Publication date: Nov. 23, 2011.

* cited by examiner

*Primary Examiner* — Layla D Berry
(74) *Attorney, Agent, or Firm* — CBM PATENT CONSULTING, LLC

(57) ABSTRACT

A cordycepin-based derived compound with an anti-tumor effect, and a structure of the compound is as shown in formula I; a cordycepin derivative and a pharmaceutical composition thereof provided by the invention have a good anti-tumor proliferation effect; compared with a parent drug, the cordycepin derivative has better affinity to cell membranes, so that a half-life period of in-vivo metabolism of the drug is longer, and in-vivo remaining time of the drug is longer; compared with other nucleoside anti-tumor drugs, the cordycepin derivative and the pharmaceutical composition thereof provided by the invention have wider types and action ranges of tumors, have excellent inhibition effects on a gastric cancer, a pancreatic cancer, a liver cancer, a small cell lung cancer, a colorectal cancer, melanoma, an ovarian cancer and the like, and have lower side effects and better curative effects.

8 Claims, 6 Drawing Sheets

CORDYCEPIN-BASED DERIVATIZED COMPOUND WITH ANTI-TUMOR EFFECT

CROSS-REFERENCE TO RELATED APPLICATIONS

This application is the U.S. continuation application of International Application No. PCT/CN2023/099859 filed on 13 Jun. 2023 which designated the U.S. and claims priority to Chinese Application No. CN202210818492.X filed on 12 Jul. 2022, the entire contents of each of which are hereby incorporated by reference.

TECHNICAL FIELD

The present invention belongs to the field of biomedicine, and particularly relates to a cordycepin-based derived compound, a preparation method thereof and an application thereof in preparing a product for preventing and treating a disease related to variation caused by a cell functional damage.

BACKGROUND

With the stimulation of external environment and the accumulation of cell damage, the adaptability of cells in a body is changed, wherein one case is the loss of cell adaptability, which eventually evolves into aging, and the other case is the abnormal enhancement of cell adaptability, which turns into a cancer. Cancer is a common disease endangering human life and health, and an incidence rate and a death rate of the cancer have been increased all over the world. At present, treatment methods for malignant tumors mainly comprise surgery, radiotherapy and chemotherapy, wherein a synthetic drug is mainly used in the chemotherapy. An inhibition effect of a chemotherapeutic drug on tumors is worthy of recognition, and the chemotherapeutic drug is also one of more effective and widely used treatment methods for malignant tumors, but has extensive and serious toxic and side effects, and a drug resistance problem. In addition, the chemotherapeutic drug has poor selectivity to tumor cells and normal cells, can damage the growth of the normal cells while killing or inhibiting the tumor cells, may have a direct impact on functions of heart, liver, kidney and nervous system, and has certain toxicity to human body. Therefore, it is very necessary to find an anti-tumor drug with low toxicity and high efficiency in tumor treatment.

Nucleoside, as one of most important endogenous compounds in human body, plays an important role in a metabolic process of the body. Modifying and derivatizing the nucleoside compound is one of main ways to prepare the anti-tumor drug, and at present, nucleoside anti-tumor drugs on the market comprise Forodesine, Fludarabine, Cladribine, Clofarabine, Fludarabine phosphate, Troxacitabine and the like. Cordycepin (3'-deoxyadenosine) is a main active ingredient of Cordyceps sinensis, which belongs to a nucleoside analogue, and has excellent effects on the change of cell adaptivity (anti-aging and anti-cancer) during metabolism in the body, immune regulation and inflammation elimination.

An anti-cancer mechanism of the cordycepin is mainly to induce cell apoptosis, regulate a cell cycle and interfere with the expression of matrix metalloproteinase (MMP), thus inhibiting the invasion and metastasis of the tumor cells. A signal pathway related to the induction of apoptosis of the tumor cells comprises an NF-κB signal pathway and a mitogen-activated protein kinase (MAPK) signal pathway. The regulation of the cell cycle is mainly manifested in the cancer cells, and the cordycepin shortens a G1 phase and prolongs a G2 phase and an M phase in the cell cycle, so that cell cycle arrest occurs in the G2/M phase, thus inhibiting cell proliferation. A generating process of matrix metalloproteinase expression is mainly intervened through inhibiting the NF-κB signal pathway, thus finally inhibiting the expression of MMP-9. However, the nucleoside analogue has poor fat solubility, is difficult to absorb and easily inactivated by deaminase metabolism, and has a short half-life and low targeting, and some tumor cells or viruses are prone to drug resistance, all of which greatly reduce a use effect of the nucleoside drug.

SUMMARY

Object of invention: the technical problem to be solved by the present invention is to provide a series of nucleoside analogues (cordycepin derivatives) chemically modified with cordycepin taken as a parent nucleus in combination with natural pharmacological activity of the cordycepin in view of shortcomings of existing nucleoside drugs.

The technical problem to be further solved by the present invention is to provide a composition comprising the nucleoside analogue above.

The technical problem to be further solved by the present invention is to provide an application of the nucleoside analogue above and a composition thereof in a product for preventing and treating a disease related to variation caused by a cell functional damage in a mammal or a human body.

The technical problem to be finally solved by the present invention is to provide a preparation method of the nucleoside analogue above.

In order to solve the first technical problem above, the present invention discloses a cordycepin derivative as shown in formula I, or a pharmaceutically acceptable salt, a stereoisomer, a tautomer, a solvate, a prodrug, or a metabolite thereof;

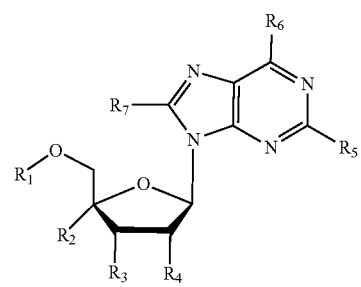

I wherein, R$_1$ is selected from hydrogen, phosphate group, phosphate ester group substituted, phosphonate group, phosphonate ester group substituted, alkyl alcohol group, amino acid alkyl ester group, amino acid alkyl alcohol ester group, alkyl acid alkyl ester group, or cycloalkyl polyol group, wherein the substitution refers to substituting with any one or more functional groups of alkoxyl, alkoxyl substituted by halogen, aryloxy, amino acid ester acylamino, alkyl ester group and methyl alkyl acid oxy; R$_2$ is selected from hydrogen or azido; R$_3$ is selected from hydrogen, fluorine, chlorine, or azido; R$_4$ is selected from hydroxyl, cyano, β-amide-γ-cyclosulfonyloxy, amino acid carboxylic ester group, amino acid alkyl ester phenyl phosphonate group, or amino acid alkyl ester phenyl phosphonate group; $R_5$ is selected from hydrogen, bromovinyl, mercapto, methyl, fluorine, or chlorine; $R_6$ is selected from amino and formamido substituted, wherein the substitution refers to substituting with any one or more functional groups of alkyl, aryl, cycloalkyl, furyl and pyridyl; $R_7$ is selected from hydrogen or isopropylamino; and there is no case that $R_1$, $R_2$, $R_3$, $R_5$ and $R_7$ are selected from hydrogen, $R_4$ is selected from hydroxyl and $R_6$ is selected from amino.

In some embodiments, $R_1$ is selected from hydrogen, such as phosphate group, diethyl phosphate group, di-n-propyl phosphate group, diisopropyl phosphate group, diisobutyl phosphate group, di-n-butyl phosphate group, or diisobutyryloxymethoxy phosphate group represented by $R_1^1$ to $R_1^7$, such as phosphonate group, trifluoroethyl phosphonate group, diisobutyryloxymethoxy phosphonate group, or neopentyloxyphosphonate group represented by $R_1^8$ to $R_1^{11}$, such as epochonoyl trifluoroethanol ester group, or cyclic phosphono ethylene ester group represented by $R_1^{12}$ to $R_1^{13}$, such as (R)-phosphono isoleucine methyl phenyl group, (S)-phosphono isoleucine methyl phenyl group, or phosphono alanine isopropyl phenyl group represented by $R_1^{14}$ to $R_1^{16}$, such as hydroxyethyl, 1,3-dihydroxy-2-propyl, alanine ethyl group, isoleucine ethyl group, isoleucine-1,3-propanediol ester group, or glycine ethyl group represented by $R_1^{17}$ to $R_1^{22}$, or such as dimethyl dicarbonate-propyl diester group, 2-isopropoxy hexahydrocyclopentane[d][1,3,2]phosphoprotein-7-alcohol group, or 1-hydroxymethyl-2,3-dihydroxy-4-cyclopentyl represented by $R_1^{23}$ to $R_1^{25}$; and in some embodiments, $R_1$ is selected from hydrogen, or a structure represented by any one of $R_1^1$, $R_1^5$, $R_1^8$, $R_1^{10}$, $R_1^{15}$, $R_1^{16}$, $R_1^{17}$ and $R_1^{21}$.

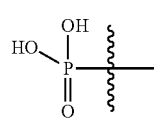

$R_1^1$

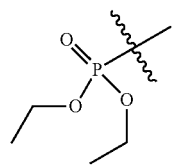

$R_1^2$

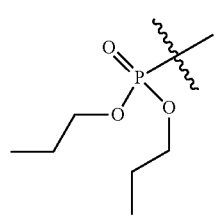

$R_1^3$

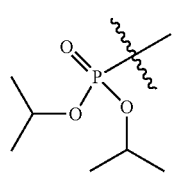

$R_1^4$

-continued

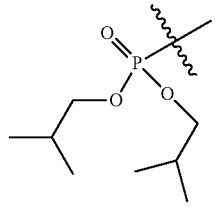

$R_1^5$

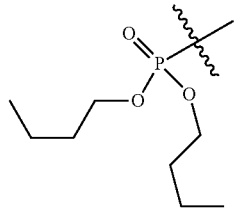

$R_1^6$

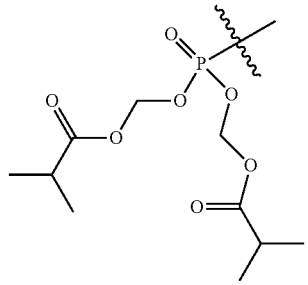

$R_1^7$

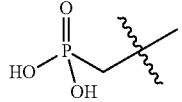

$R_1^8$

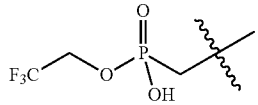

$R_1^9$

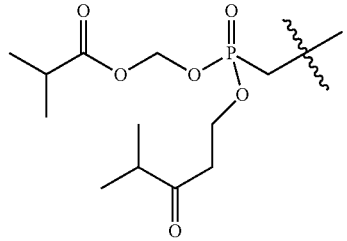

$R_1^{10}$

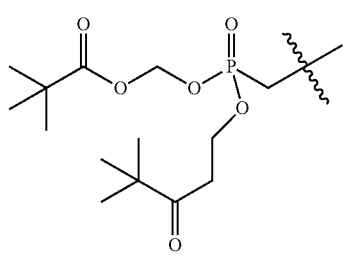

$R_1^{11}$

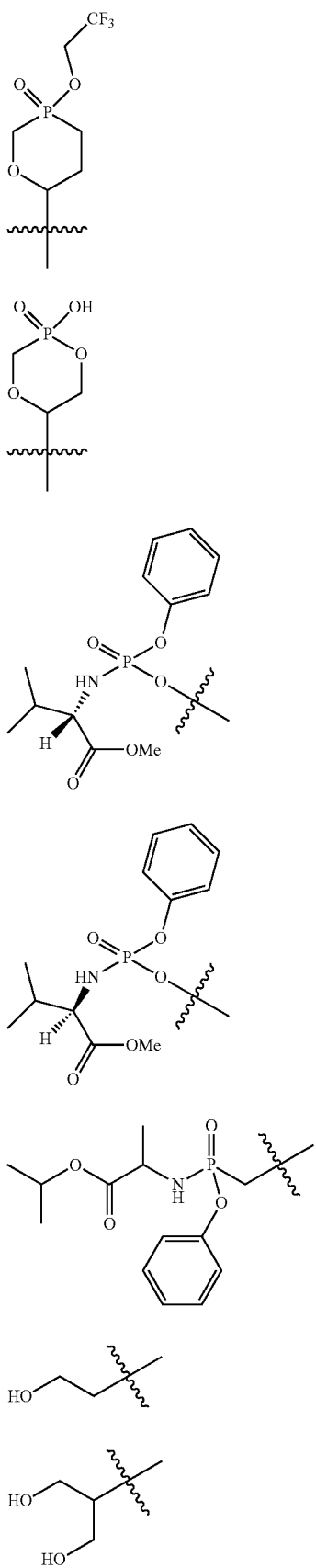
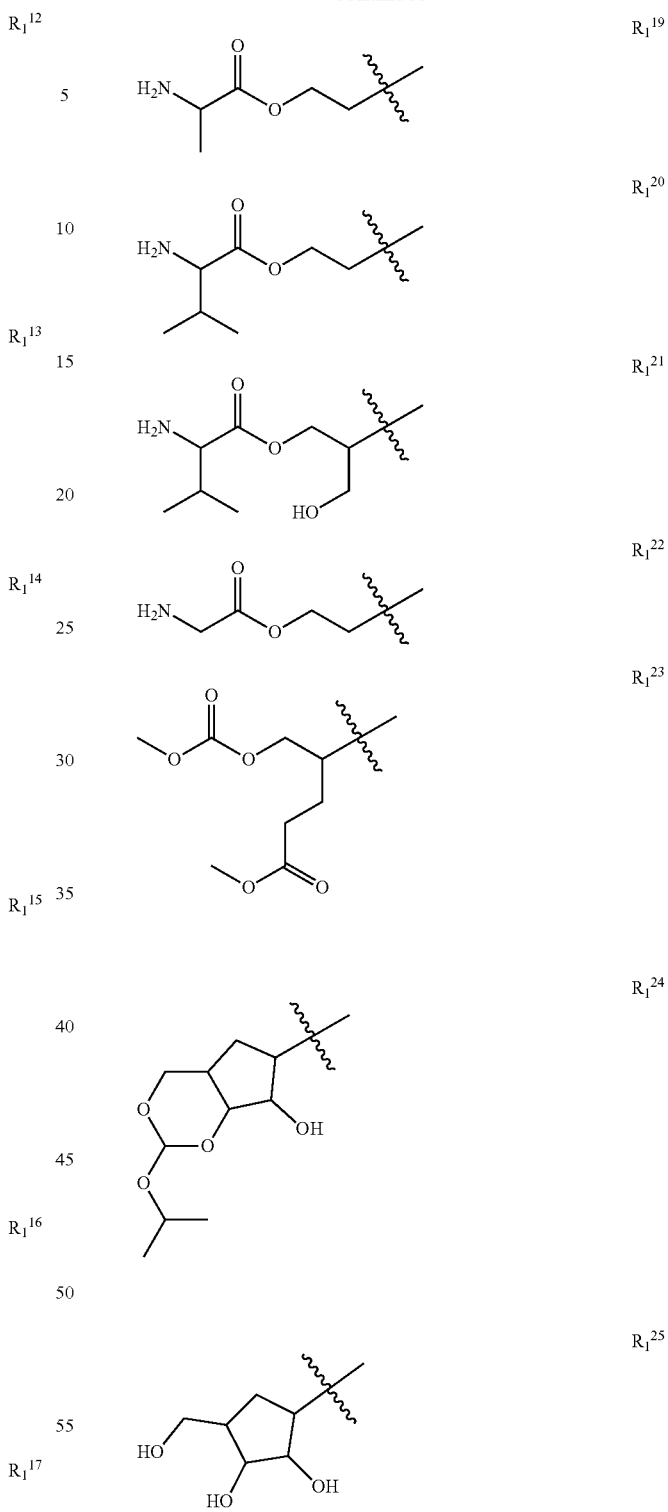

In some embodiments, $R_4$ is selected from hydroxyl, cyano, β-amide-γ-cyclic sulfonyloxy, 2-amino-propionyloxy, 2-amino-3-methyl-butyryloxy, phosphatidyl alanine methyl ester phenyl group, or phosphinamido isoleucine methyl ester phenyl group represented by $R_4^1$ to $R_4^7$; and in some embodiments, $R_4$ is selected from cyano, or a structure represented by any one of $R_4^3$, $R_4^5$ or $R_4^6$.

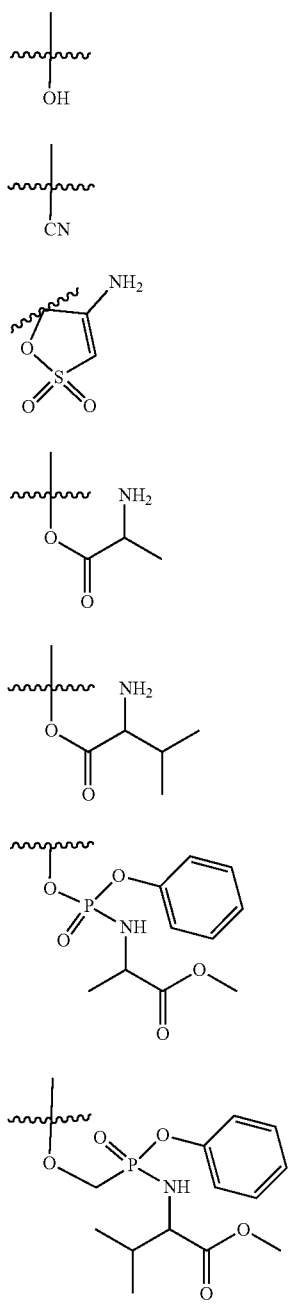

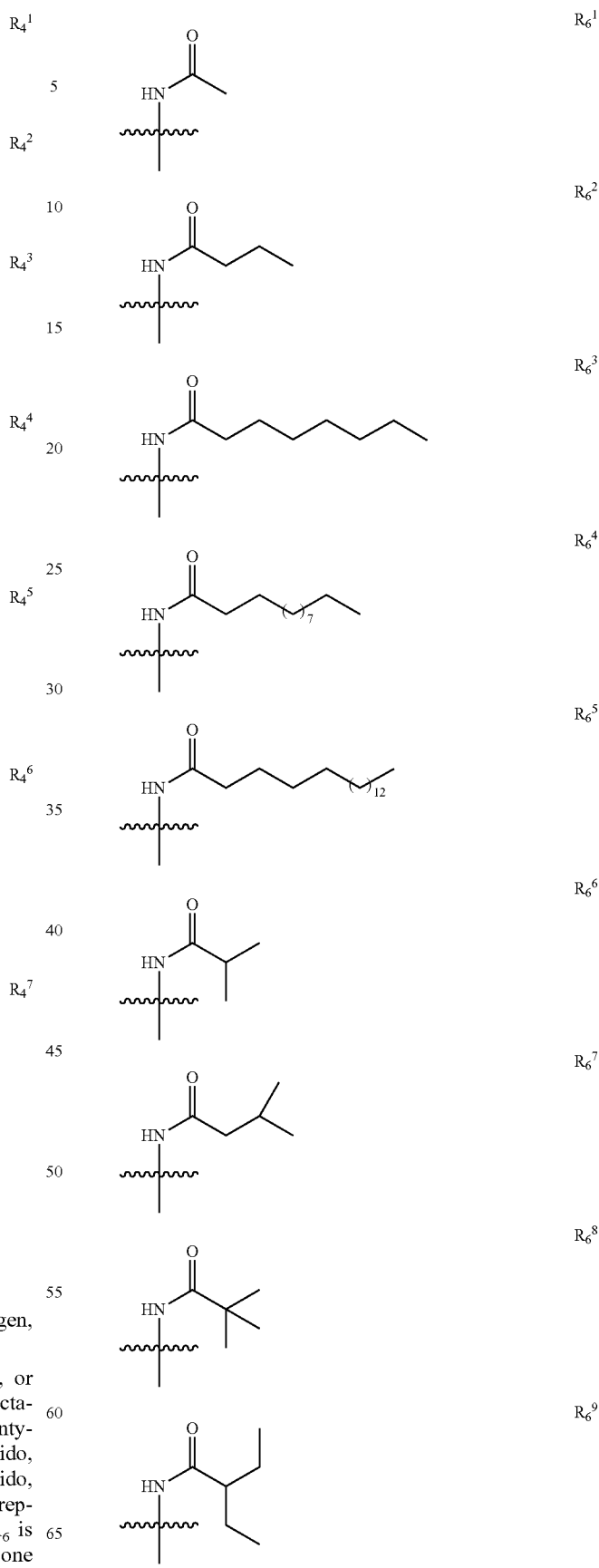

In some embodiments, $R_5$ is selected from hydrogen, bromovinyl, mercapto, fluorine, or chlorine.

In some embodiments, $R_6$ is selected from amino, or acetamido, butylamido, octanamido, dodecyl amido, octadecyl amido, isopropylamido, isobutyramido, neopentylamido, 2-ethyl n-butylamido, 3,3-dimethyl-butylamido, cyclohexyl formamido, cyclopentyl formamido, benzamido, furan formamido, pyridine formamido, or cetylamido represented by $R_6^1$ to $R_6^{16}$; and in some embodiments, $R_6$ is selected from amino, or a structure represented by any one of $R_6^5$, $R_6^{12}$, $R_6^{13}$ or $R_6^{15}$.

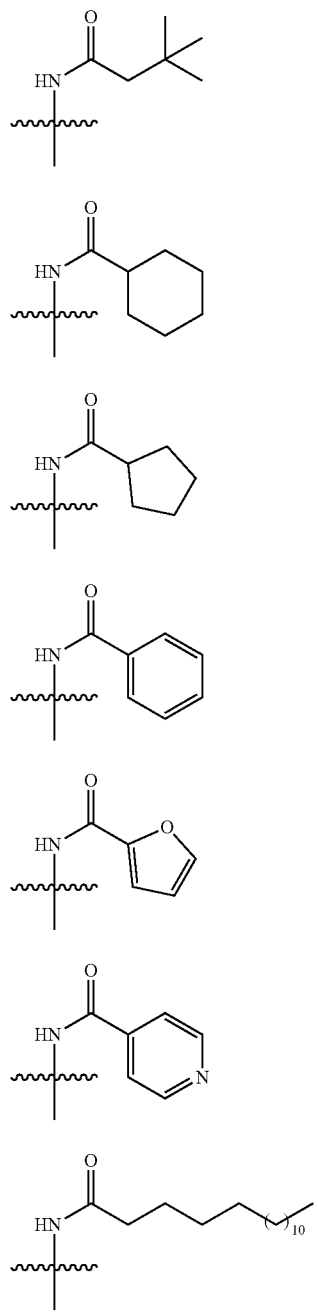

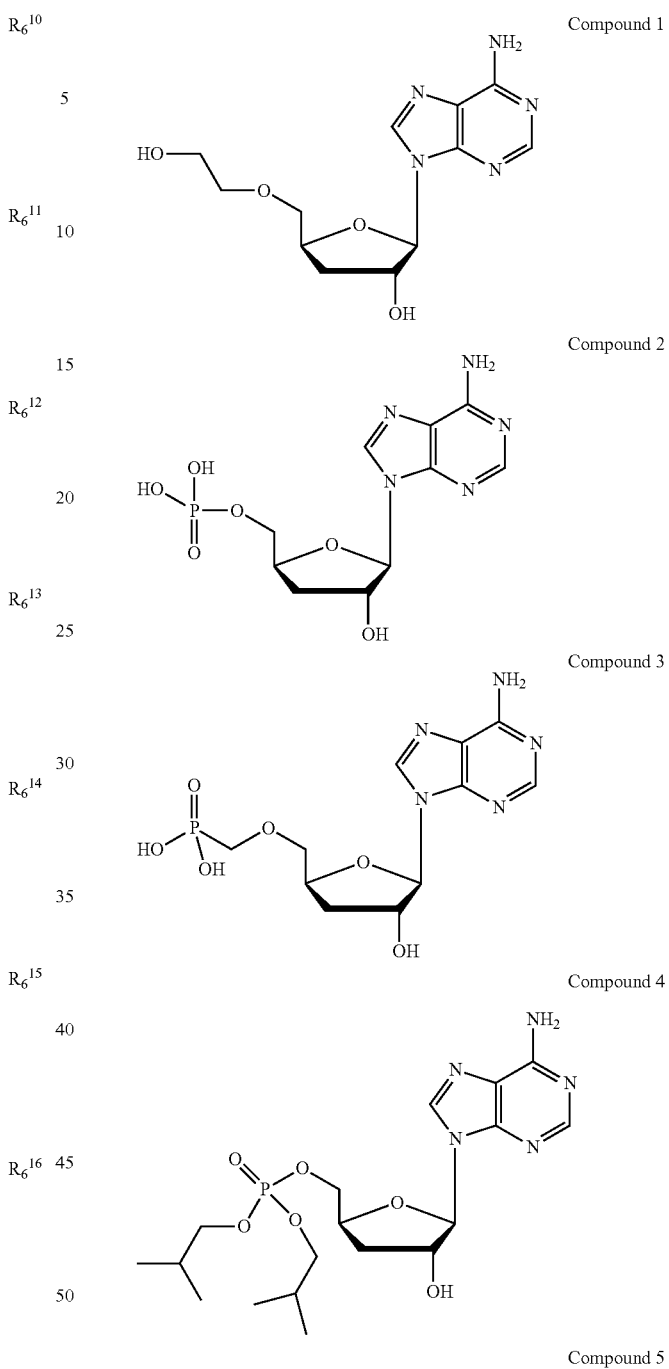

In some embodiments, according to the cordycepin derivative as shown in formula I, or the pharmaceutically acceptable salt thereof, $R_1$ is a group represented by $R_1^{16}$, $R_2$ is selected from hydrogen, $R_3$ is selected from hydrogen, $R_4$ is selected from hydroxyl, $R_5$ is selected from hydrogen, fluorine, or chlorine, $R_6$ is selected from pyridine carboxamido or amino, and $R_7$ is selected from hydrogen; and in some embodiments, the cordycepin derivative as shown in formula I is selected from the following compound 24, the following compound 7 or the following compound 20.

In some embodiments, the cordycepin derivative as shown in formula I is selected from any one of a compound 1 to a compound 40.

Compound 6
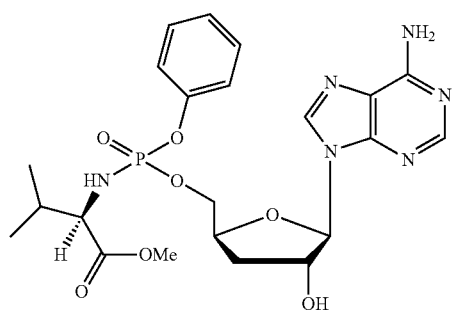
Compound 7
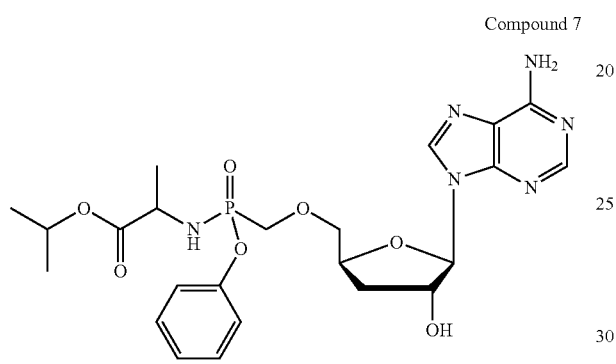
Compound 8
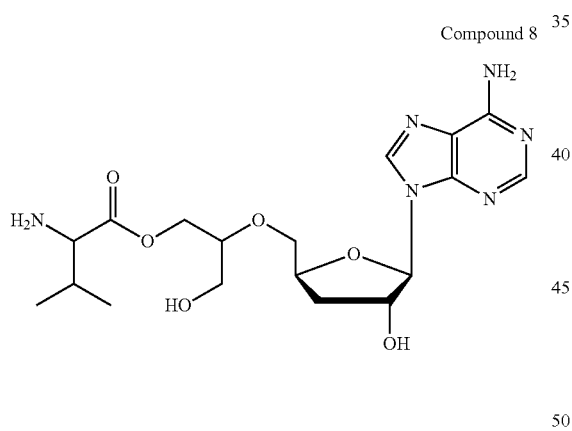
Compound 9
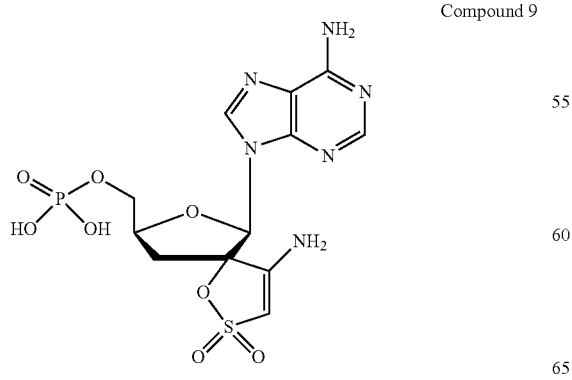
Compound 10
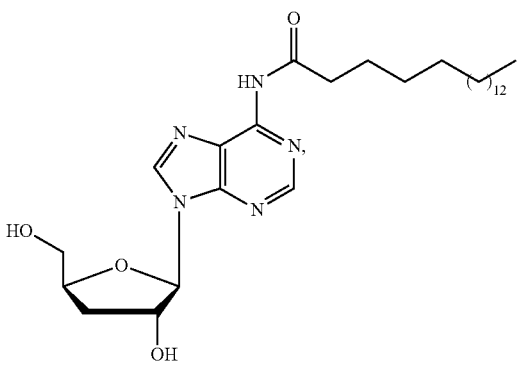
Compound 11
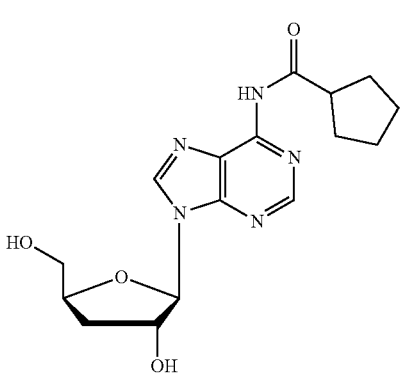
Compound 12
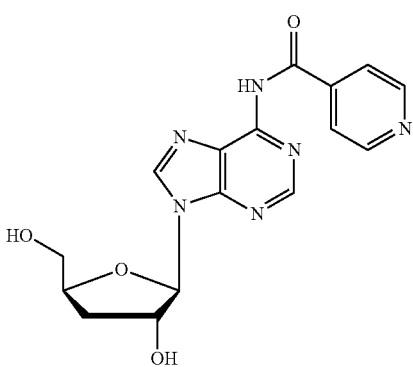
Compound 13
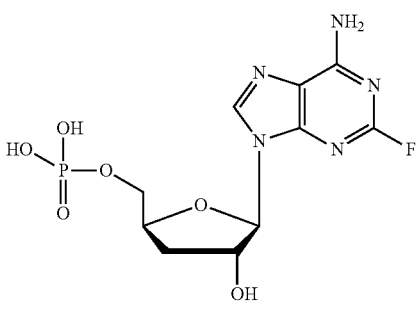

Compound 14
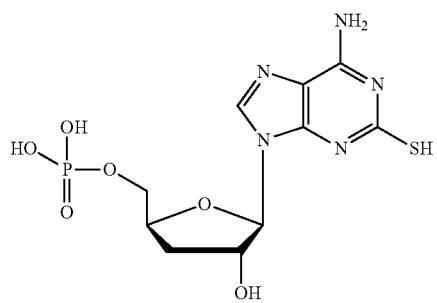
Compound 18
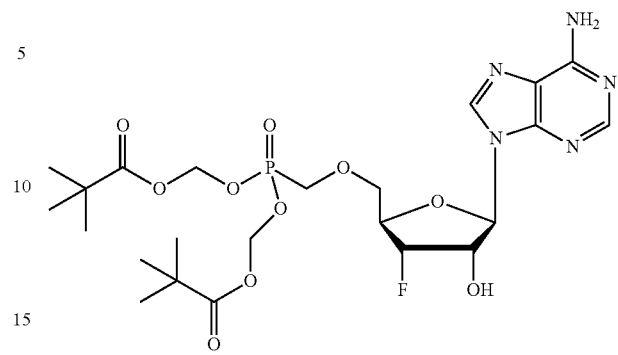
Compound 15
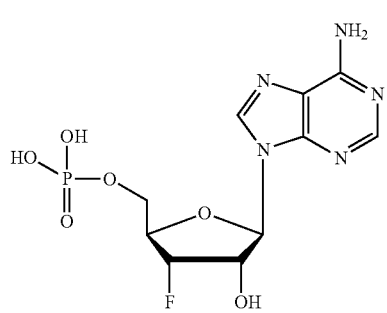
Compound 19
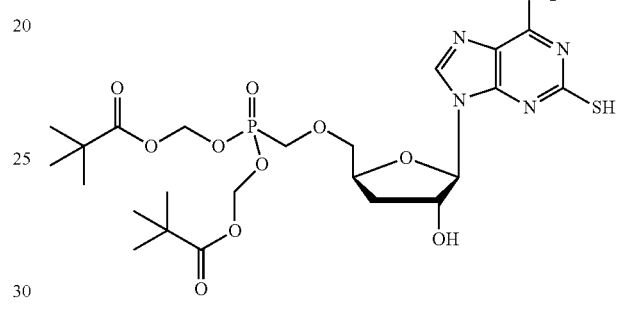
Compound 16
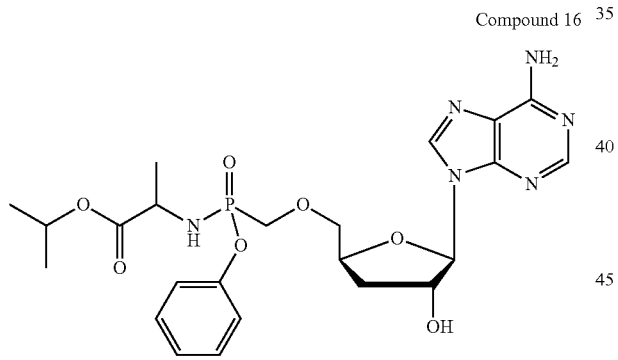
Compound 20
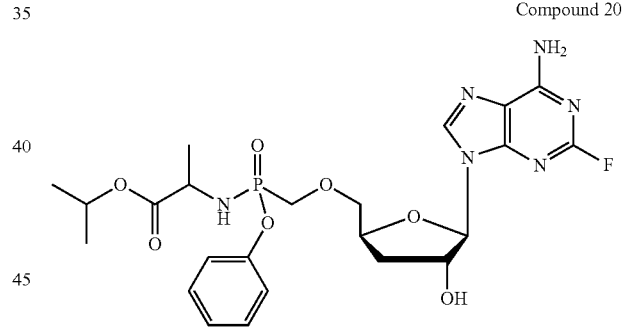
Compound 17
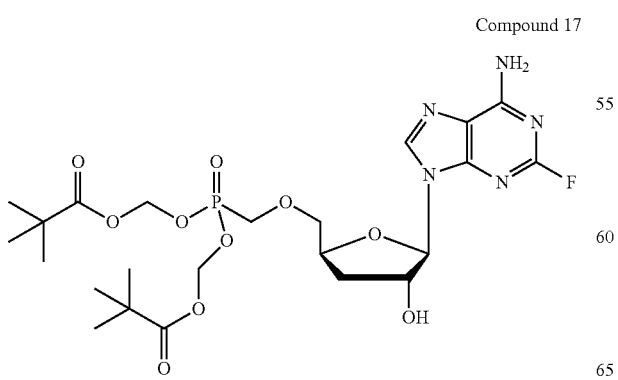
Compound 21
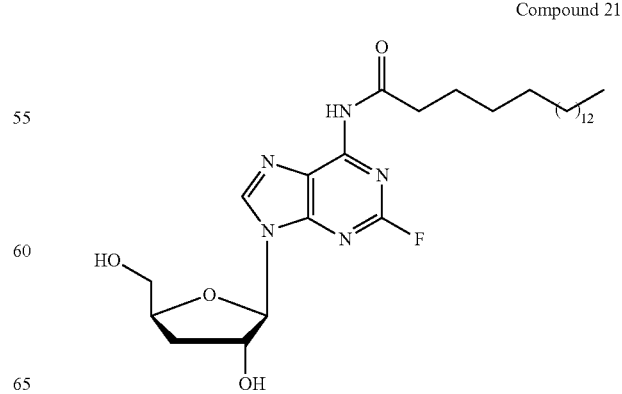

Compound 22
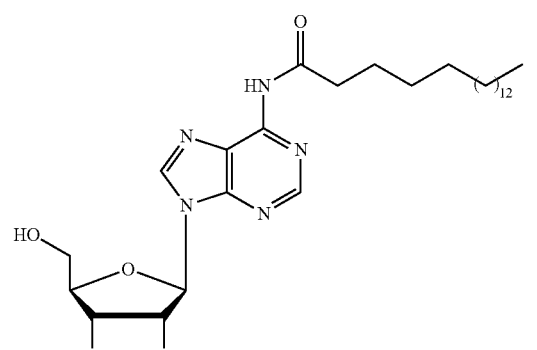
Compound 23
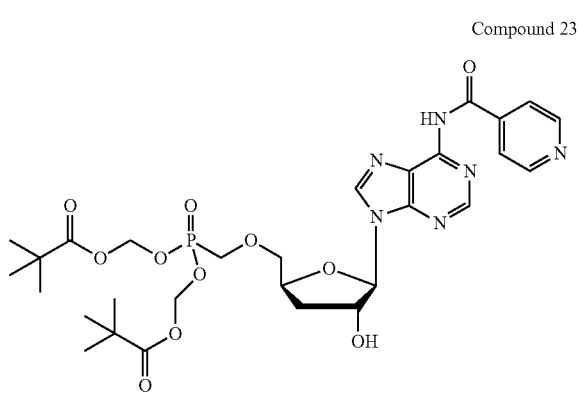
Compound 24
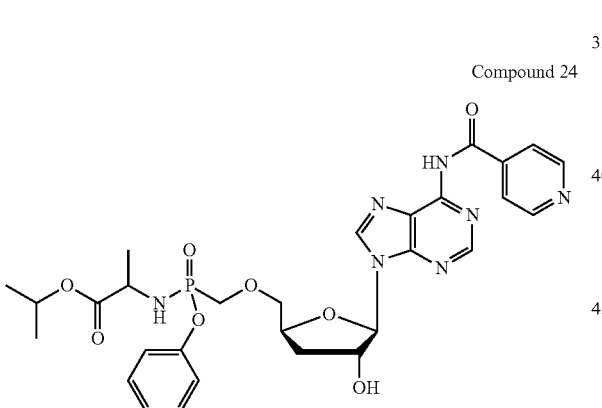
Compound 25
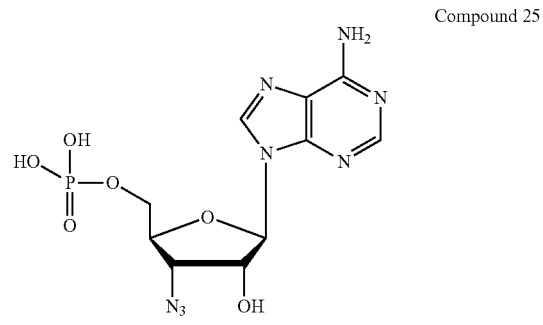
Compound 26
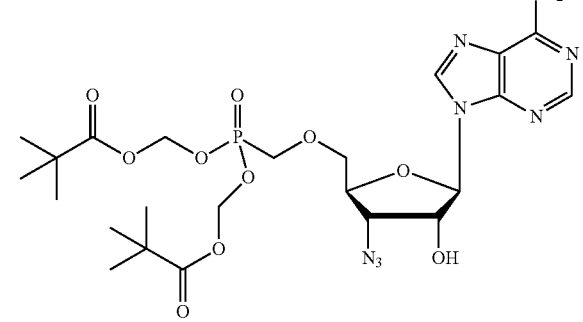
Compound 27
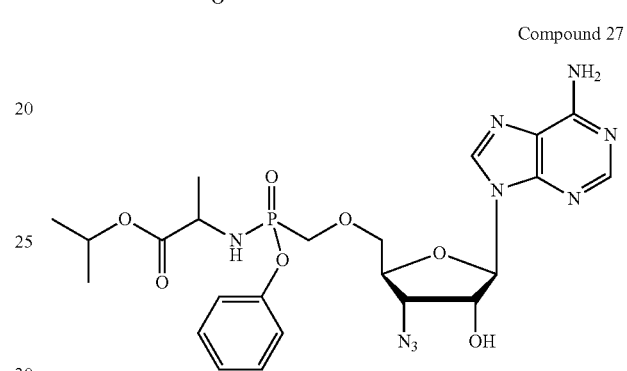
Compound 28
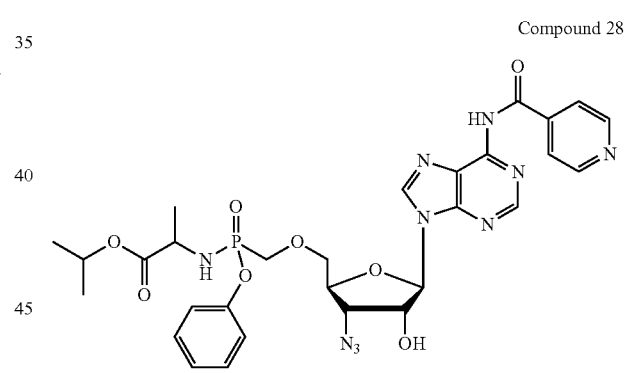
Compound 29
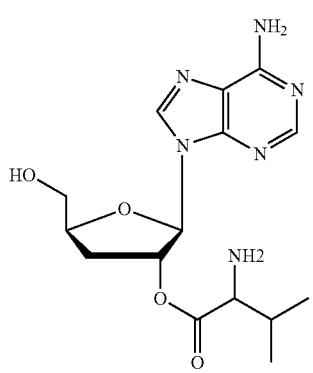

Compound 30
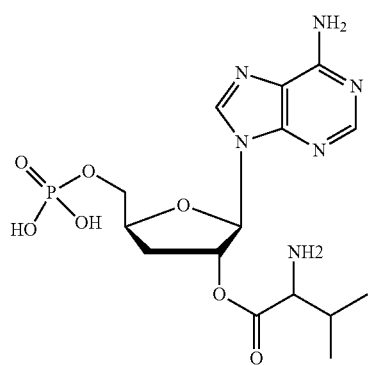
Compound 31
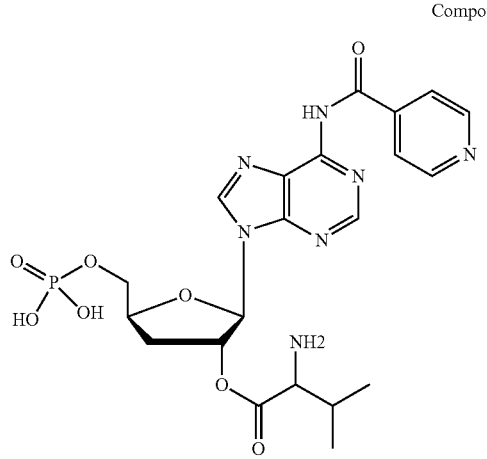
Compound 32
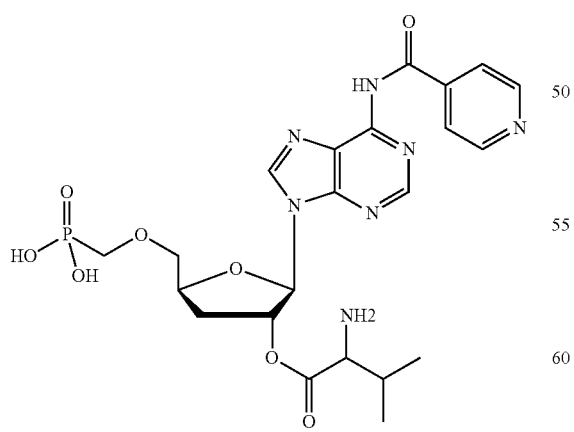
Compound 33
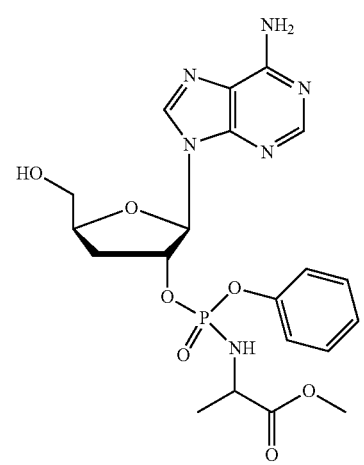
Compound 34
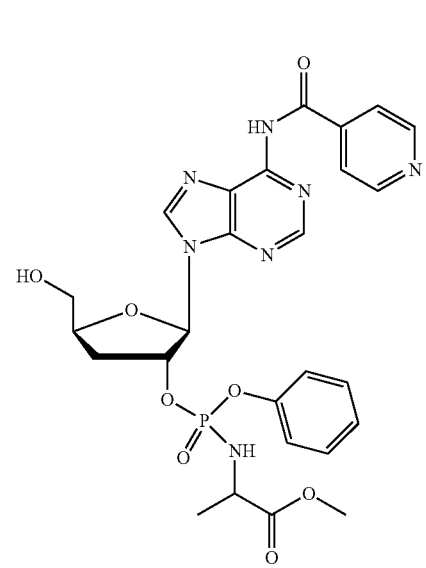
Compound 35
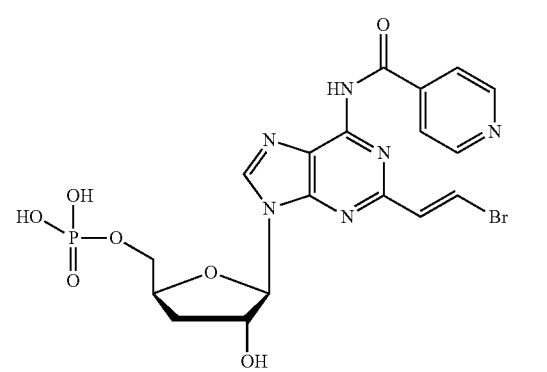

-continued

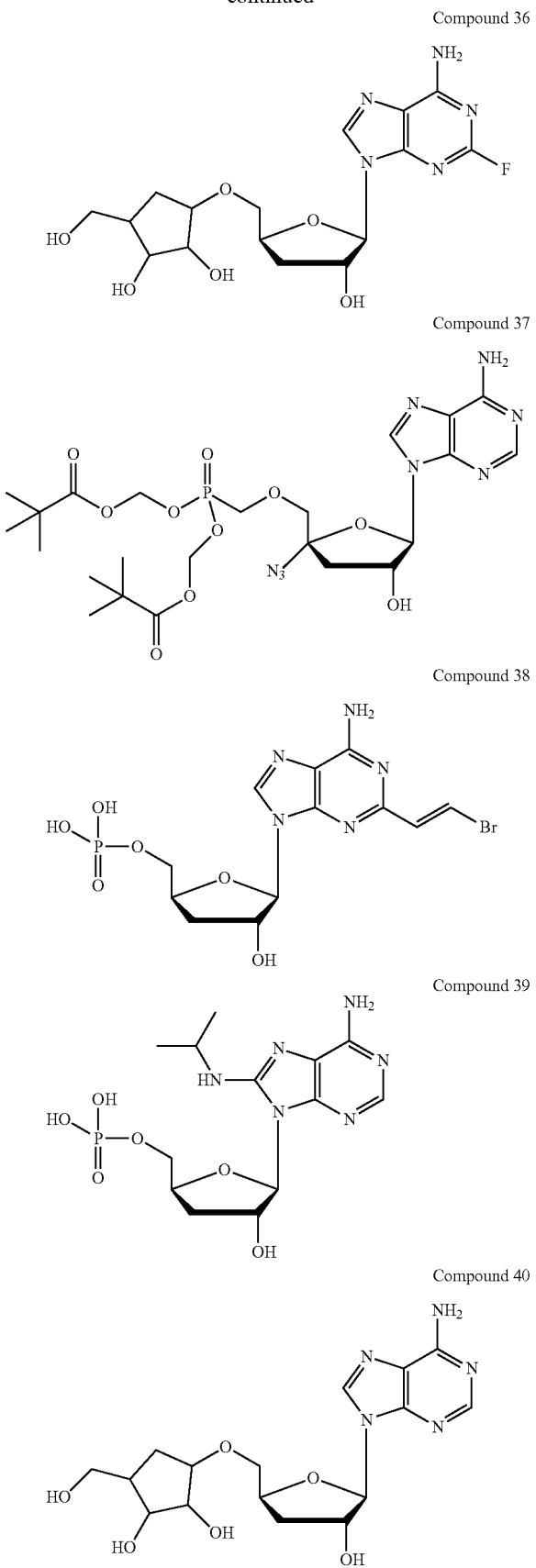

In order to solve the second technical problem above, the present invention discloses a pharmaceutical composition, which comprises at least one cordycepin derivative, or the pharmaceutically acceptable salt, the stereoisomer, the tautomer, the solvate, the prodrug, or the metabolite thereof above; and at least one immune checkpoint inhibitor.

In some embodiments, the immune checkpoint inhibitor is selected from a PD-1 and/or CTLA4 monoclonal antibody.

In some embodiments, a mass ratio of the cordycepin derivative, or the pharmaceutically acceptable salt, the stereoisomer, the tautomer, the solvate, the prodrug, or the metabolite thereof to the immune checkpoint inhibitor is 1:0.2 to 10, in some embodiments, the mass ratio is 1:0.2 to 8, in some embodiments, the mass ratio is 1:0.2 to 5, in some embodiments, the mass ratio is 1:0.2 to 3, in some embodiments, the mass ratio is 1:0.2 to 2, in some embodiments, the mass ratio is 1:0.5 to 1.5, in some embodiments, the mass ratio is 1:0.8 to 1.2, and in some embodiments, the mass ratio is 1:1.

In some embodiments, a dosage form of the pharmaceutical composition is selected from a tablet, a pill, a capsule, a dripping pill, a syrup, a disintegrant, an injection, a sustained to Release agent, or a kit.

In order to solve the third technical problem above, the present invention discloses an application of the cordycepin derivative, or the pharmaceutically acceptable salt, the stereoisomer, the tautomer, the solvate, the prodrug, or the metabolite thereof above, or the pharmaceutical combination above in preparation of a product for preventing and treating a disease related to variation caused by a cell functional damage in a mammal or a human body.

In some embodiments, the disease related to the variation caused by the cell functional damage is a tumor; in some embodiments, the tumor comprises, but is not limited to, a gastric cancer, a pancreatic cancer, a liver cancer, a small cell lung cancer, a non-small cell lung cancer, a colorectal cancer, an esophageal cancer, a prostate cancer, melanoma, glioma, and an ovarian cancer; and in some embodiments, the tumor is any one of the gastric cancer, the pancreatic cancer, the liver cancer, the small cell lung cancer, the colorectal cancer, the melanoma and the ovarian cancer.

In some embodiments, the product comprises, but is not limited to, a drug.

In order to solve the fourth technical problem above, the present invention discloses a preparation method of the cordycepin derivative above, the preparation method is a synthetic method of corresponding modification, considering that the cordycepin or other active groups in modified cordycepin molecules may participate in the reaction in the reaction process, the cordycepin should be properly protected, a protection method involved in the present invention comprises protection and deprotection of hydroxyl and amino, wherein protection and deprotection means are both conventional means in the art, and other reaction systems need to be protected by adding protective gas, which are all conventional means in the experimental process in the art.

Specifically:

A. Modification of $R_1$ $R_1$ is selected from phosphate group, phosphate ester group substituted, phosphonate group, phosphonate ester group substituted, alkyl alcohol group, amino acid alkyl ester group, amino acid alkyl alcohol ester group, alkyl acid alkyl ester group, or cycloalkyl polyol group in formula I, wherein the substitution refers to substituting with any one or more functional groups of alkoxyl, alkoxyl substituted by halogen, aryloxy, amino acid ester acylamino, alkyl ester group and methyl alkyl acid oxy; and the preparation method of the cordycepin derivative as shown in formula I comprises: using a compound I-R-1 as a raw material for a chemical reaction in an organic solvent to prepare the cordycepin derivative as shown in formula I;

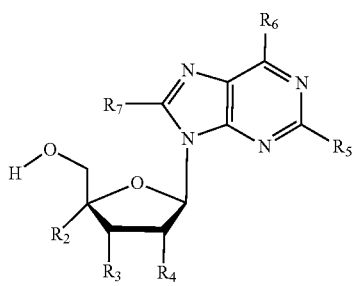

I-R-1 in formula I-R-1, $R_2$ to $R_7$ are the same as $R_2$ to $R_7$ in formula I, or are independently selected from protecting groups respectively.

When $R_1$ is selected from the phosphate group in formula I, in some embodiments, the preparation method of the cordycepin derivative as shown in formula I comprises: reacting the compound I-R-1 with a modifier phosphorus oxychloride in trimethyl phosphite and/or triethyl phosphite, in some embodiments, a dosage ratio of the compound I-R-1 to the modifier and the organic solvent is 1 mmol:3 mmol to 6 mmol:15 mL to 30 mL, in some embodiments, a temperature of the reaction is −10° C. to 5° C., and in some embodiments, the reaction lasts for 0.5 hour to 2 hours.

When $R_1$ is selected from the phosphate ester group substituted in formula I, in some embodiments, the preparation method of the cordycepin derivative as shown in formula I comprises: reacting the compound I-R-1 with nitrophenyl phosphate substituted by a modifier in anhydrous N,N-dimethylformamide and/or tetrahydrofuran with tert-butyl magnesium chloride as a catalyst, wherein the substitution refers to substituting with any one or more functional groups of alkoxyl, alkoxyl substituted by halogen, aryloxy, amino acid ester acylamino, alkyl ester group and methyl alkyl acid oxy, in some embodiments, a dosage ratio of the compound I-R-1 to the modifier, the catalyst and the organic solvent is 1 mmol:1 mmol to 3 mmol:1 mmol to 2 mmol:9 mL to 15 mL, in some embodiments, a temperature of the reaction is 20° C. to 40° C., and in some embodiments, the reaction lasts for 2 hours to 5 hours.

When $R_1$ is selected from the phosphonate group or the phosphonate ester group substituted, in some embodiments, the preparation method of the cordycepin derivative as shown in formula I comprises: reacting the compound I-R-1 with p-toluenesulfonyloxymethyl phosphate substituted or non-substituted by a modifier in anhydrous N,N-dimethylformamide with NaH as a catalyst, wherein the substitution refers to substituting with any one or more functional groups of alkoxyl, alkoxyl substituted by halogen, aryloxy, amino acid ester acylamino, alkyl ester group and methyl alkyl acid oxy, in some embodiments, a dosage ratio of the compound I-R-1 to the modifier, the catalyst and the organic solvent is 0.1 mol:0.1 mol to 0.15 mol:0.2 mol to 0.03 mol:100 mL to 200 mL, in some embodiments, the dosage ratio is 0.1 mol:0.1 mol to 0.15 mol:0.2 mol to 0.03 mol:150 mL, in some embodiments, a temperature of the reaction is −20° C. to 0° C., and in some embodiments, the reaction lasts for 0.5 hour to 6 hours.

When $R_1$ is selected from alkyl alcohol group, amino acid alkyl ester group, amino acid alkyl alcohol ester group, alkyl acid alkyl ester group, or cycloalkyl polyol group in formula I, in some embodiments, the preparation method of the cordycepin derivative as shown in formula I comprises: reacting the compound I-R-1 with a modifier in butanone with potassium carbonate as a catalyst, wherein the modifier is alkyl alcohol substituted by halogen, amino acid alkyl ester, amino acid alkyl alcohol ester, alkyl acid alkyl ester or cycloalkyl polyol, in some embodiments, the halogen is bromine or chlorine, in some embodiments, a dosage ratio of the compound I-R-1 to the modifier, the catalyst and the organic solvent is 1 mmol:0.5 mmol to 1.5 mmol:1 mmol to 3 mmol:5 mL to 8 mL, in some embodiments, the dosage ratio is 1 mmol:1 mmol:1 mmol to 3 mmol:5 mL to 8 mL, in some embodiments, a temperature of the reaction is 40° C. to 100° C., and in some embodiments, the reaction lasts for 8 hour to 20 hours.

B. Modification of $R_2$

When $R_2$ is selected from the azido in formula I, the preparation method of the cordycepin derivative as shown in formula I comprises: using a compound I-R-2 as a raw material for a cyclization reaction in an organic solvent to prepare an intermediate I-R-2a, which is 5-(6-amino-9H-purine-9-yl)-1,4-dioxopyrrole[2.4]heptane-6-alcohol or a derivative thereof; and subjecting the obtained intermediate I-R-2a to a ring-opening reaction in the organic solvent to prepare the cordycepin derivative as shown in formula I;

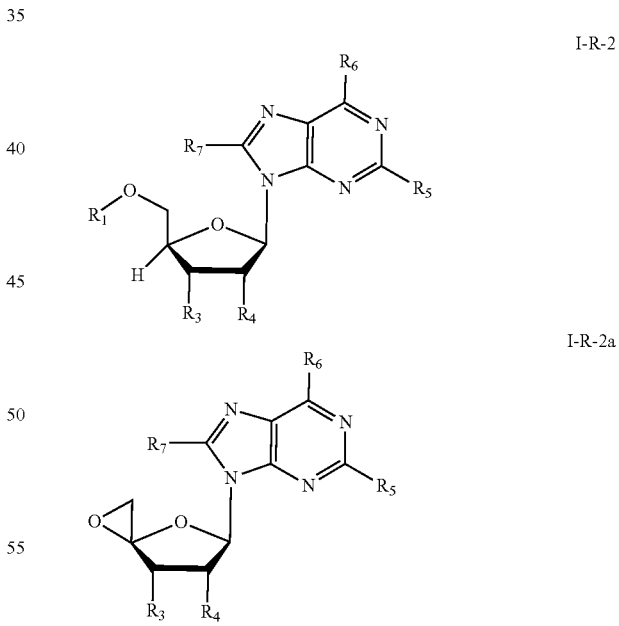

in formula I-R-2, $R_1$ and $R_3$ to $R_7$ are the same as $R_1$ and $R_3$ to $R_7$ in formula I, or are independently selected from protecting groups respectively.

In some embodiments, the preparation method of the intermediate I-R-2a comprises: subjecting the compound I-R-2 to a cyclization reaction under catalysis of phosphorus pentoxide and m-chloroperoxybenzoic acid in dichloromethane, in some embodiments, a dosage ratio of the compound I-R-2 to the phosphorus pentoxide, the m-chloroperoxybenzoic acid and the dichloromethane is 1 mmol: 1.2 mmol to 2 mmol:2 mmol to 3 mmol:10 mL to 20 mL, in some embodiments, a temperature of the cyclization reaction is 20° C. to 60° C., and in some embodiments, the cyclization reaction lasts for 3 hours to 10 hours.

In some embodiments, the preparation method of the cordycepin derivative as shown in formula I comprises: subjecting the intermediate I-R-2a to a ring-opening reaction with sodium azide in anhydrous dimethylformamide, in some embodiments, a dosage ratio of the compound I-R-2a to the sodium azide and the dimethylformamide is 1 mmol:4 mmol to 5 mmol:2 mL to 5 mL, in some embodiments, a temperature of the ring-opening reaction is 100° C. to 120° C., and in some embodiments, the ring-opening reaction lasts for 12 hour to 16 hours.

C. Modification of $R_3$

When $R_3$ is selected from the fluorine, the chlorine or the azido in formula I, the preparation method of the cordycepin derivative as shown in formula I comprises: using a compound I-R-3 as a raw material for a chemical reaction in an organic solvent to prepare the cordycepin derivative as shown in formula I;

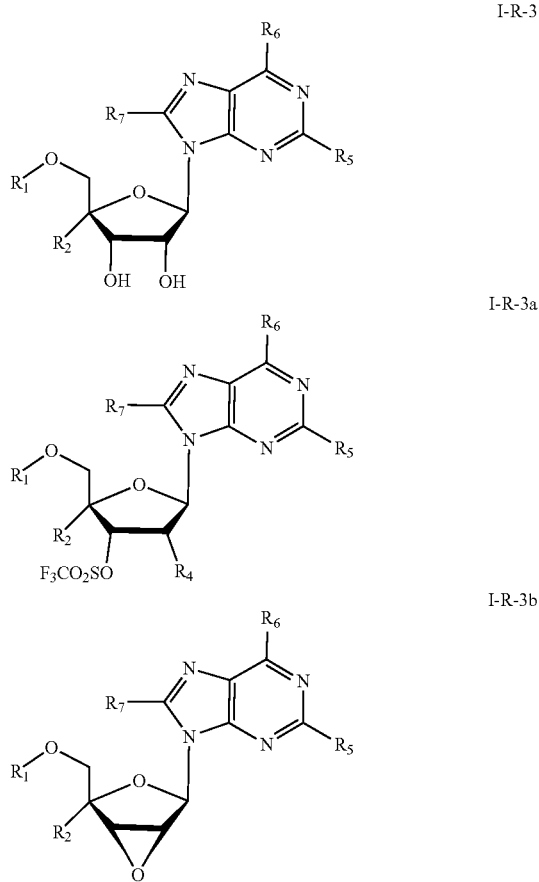

I-R-3

I-R-3a

I-R-3b in formula I-R-3, $R_1$, $R_2$, and $R_5$ to $R_7$ are the same as $R_1$, $R_2$, and $R_5$ to $R_7$ in formula I, or are independently selected from protecting groups respectively;

when $R_3$ is selected from the fluorine or the chlorine in formula I, in some embodiments, the preparation method of the cordycepin derivative as shown in formula I comprises: reacting the compound I-R-3 with trifluoromethanesulfonic anhydride in pyridine and dichloromethane to prepare an intermediate I-R-3a, which is 5-(6-amino-9H-purine-9-yl)-4-hydroxy-2-(hydroxymethyl)tetrahydrofuran-3-yl trifluoromethane sulfonate or a derivative thereof; and subjecting the intermediate I-R-3a to a substitution reaction with hydrofluoric acid, sulfur trifluoride or hydrochloric acid in ethyl acetate to prepare the cordycepin derivative as shown in formula I; wherein, in the preparation method of the intermediate I-R-3a, in some embodiments, a dosage ratio of the compound I-R-3 to the trifluoromethanesulfonic anhydride, the pyridine and the dichloromethane is 1 mmol:1 mmol to 1.5 mmol:0.15 mL to 0.2 mL:10 mL to 20 mL, in some embodiments, a temperature of the reaction is −5° C. to 5° C., in some embodiments, the temperature is 0° C., and in some embodiments, the reaction lasts for 1 hour to 3 hours; wherein, in the preparation method of the cordycepin derivative as shown in formula I, in some embodiments, the intermediate I-R-3a is subjected to the substitution reaction with a triethylamine solution of 37% hydrofluoric acid or diethylamino sulfur trifluoride or hydrochloric acid, in some embodiments, a dosage ratio of the intermediate I-R-3a to the triethylamine solution of 37% hydrofluoric acid or diethylamino sulfur trifluoride or hydrochloric acid and the ethyl acetate is 1 mmol:2 mmol to 3 mmol:4 mL to 10 mL, in some embodiments, a temperature of the reaction is 60° C. to 80° C., and in some embodiments, the reaction lasts for 8 hours to 10 hours.

When $R_3$ is selected from the azido in formula I, in some embodiments, the preparation method of the cordycepin derivative as shown in formula I comprises: subjecting the compound I-R-3 to a cyclization reaction under catalysis of triphenylphosphorus and diisopropyl azodicarboxylate in N,N-dimethylformamide to prepare an intermediate I-R-3b, which is 4-(6-amino-9H-purine 9-yl)-3,6-dioxane[3.1.0] hexane-2-yl)methanol or a derivative thereof; and subjecting the intermediate I-R-3b to a cyclization reaction with sodium azide in dimethylformamide to prepare the cordycepin derivative as shown in formula I; wherein, in the preparation method of the intermediate I-R-3b, in some embodiments, a dosage ratio of the compound I-R-3 to the triphenylphosphorus, the diisopropyl azodicarboxylate and the N,N-dimethylformamide is 10.0 mmol:16 mmol to 28 mmol:1.6 mmol to 2.8 mmol:15 mL to 50 mL, in some embodiments, the dosage ratio is 10.0 mmol:22 mmol:2.2 mmol:15 mL to 50 mL, in some embodiments, a temperature of the reaction is 10° C. to 60° C., and in some embodiments, the cyclization reaction lasts for 1 hour to 5 hours; in some embodiments, in the preparation method of the cordycepin derivative as shown in formula I, a dosage ratio of the intermediate I-R-3b to the sodium azide and the dimethylformamide is 1 mmol:4 mmol to 5 mmol:2 mL to 5 mL, in some embodiments, a temperature of the cyclization reaction is 100° C. to 120° C., and in some embodiments, the cyclization reaction lasts for 12 hours to 16 hours.

D. Modification of $R_4$

When $R_4$ is selected from the cyano, the β-amide-γ-cyclosulfonyloxy, the amino acid carboxylic ester group, the amino acid alkyl ester phenyl phosphonate group, or the amino acid alkyl ester phenyl phosphonate group in formula I, the preparation method of the cordycepin derivative as shown in formula I comprises: using a compound I-R-4 as a raw material for a chemical reaction in an organic solvent to prepare the cordycepin derivative as shown in formula I;

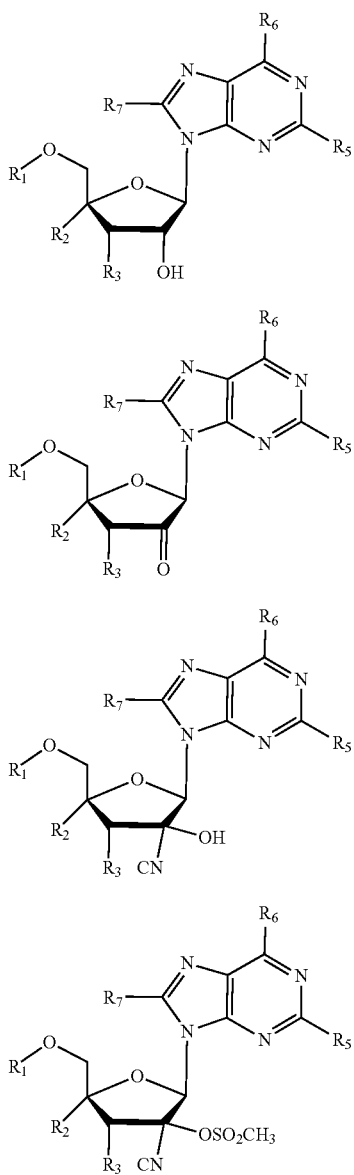

in formula I-R-4, $R_1$ to $R_3$ and $R_5$ to $R_7$ are the same as $R_1$ to $R_3$ and $R_5$ to $R_7$ in formula I, or are independently selected from protecting groups respectively.

When $R_4$ is selected from the cyano in formula I, in some embodiments, the preparation method of the cordycepin derivative as shown in formula I comprises: stirring the compound I-R-4, trifluoromethanesulfonic acid and trimethylsilyl triflate in dichloromethane at −50° C. to −30° C., and then reacting the mixture with trimethyl nitrile silane and triethylamine; in some embodiments, a dosage ratio of the compound I-R-4 to the trifluoromethanesulfonic acid, the trimethylsilyl triflate and the dichloromethane is 10 mmol: 0.8 mL to 1.8 mL:2.2 mL to 3.2 mL:90 mL to 110 mL, in some embodiments, the dosage ratio is 10 mmol:1.3 mL:2.7 mL:100 mL, and in some embodiments, the stirring lasts for 20 minutes to 40 minutes, in some embodiments, the stirring lasts for 30 minutes; in some embodiments, a dosage ratio of the compound I-R-4 to the trimethyl nitrile silane and the triethylamine is 10 mmol:3.4 g to 4.3 g:3 mL to 4 mL, in some embodiments, a temperature of the reaction is 20° C. to 30° C., in some embodiments, the temperature is room temperature, and in some embodiments, the reaction lasts for 2 hours to 4 hours.

When $R_4$ is selected from the β-amide-γ-cyclosulfonyloxy, in some embodiments, the preparation method of the cordycepin derivative as shown in formula I comprises: subjecting the compound I-R-4 to an oxidation reaction to prepare an intermediate I-R-4a, which is 2-(6-amino-1,6-dihydro-9H-purin-9-yl)-5-(hydroxymethyl)dihydrofuran-3(2H)-one or a derivative thereof, then subjecting the intermediate I-R-4a to a cyanation reaction to prepare an intermediate I-R-4b, which is 2-(6-amino-1,6-dihydro-9H-purin-9-yl)-5-(hydroxymethyl)-3-isocyanatotetrahydrofuran-3-ol or a derivative thereof, then subjecting the intermediate I-R-4b to methylsulfonic acid esterification to prepare an intermediate I-R-4c, which is 2-(6-amino-1,6-dihydro-9H-purine-9-yl)-5-(hydroxymethyl)-3-isocyanato-tetrahydrofuran-3-ylmethane sulfonate or a derivative thereof, and finally subjecting the intermediate I-R-4c to a ring-closure reaction to prepare the cordycepin derivative as shown in formula I; in some embodiments, the preparation method of the intermediate I-R-4a comprises: reacting the compound I-R-4 with a Jones reagent 2.2 M chromium trioxide in acetone, in some embodiments, a dosage ratio of the compound I-R-4 to the Jones reagent and the acetone is 20 mmol:5 mL to 8 mL:50 mL to 100 mL, in some embodiments, a temperature of the reaction is 0° C. to 40° C., and in some embodiments, the reaction lasts for 1 hour to 4 hours; in some embodiments, the preparation method of the intermediate I-R-4b comprises: reacting the intermediate I-R-4a with trimethylsilyl cyanide and boron trifluoride diethyl ether in dichloromethane, in some embodiments, a dosage ratio of the intermediate I-R-4a to the trimethylsilyl cyanide, the boron trifluoride diethyl ether and the dichloromethane is 20 mmol:20 mmol to 40 mmol:10 mmol to 30 mmol:50 mL to 100 mL, in some embodiments, the dosage ratio is 20 mmol:20 mmol to 40 mmol:20 mmol:50 mL to 100 mL, and in some embodiments, a temperature of the reaction is 0° C. to 40° C., and in some embodiments, the reaction lasts for 1 hour to 4 hours; in some embodiments, the preparation method of the intermediate I-R-4c comprises: reacting the intermediate I-R-4b with triethylamine and methanesulfonyl chloride in anhydrous dichloromethane, in some embodiments, a dosage ratio of the intermediate I-R-4b to the triethylamine, the methanesulfonyl chloride and the anhydrous dichloromethane is 2.2 mmol:10 mmol to 15 mmol:4 mmol to 8 mmol:5 mL to 10 mL, in some embodiments, a temperature of the reaction is −30° C. to 0° C., and in some embodiments, the reaction lasts for 2 hours to 4 hours; and in some embodiments, the preparation method of the cordycepin derivative as shown in formula I comprises: reacting the intermediate I-R-4c with cesium carbonate in anhydrous acetonitrile, in some embodiments, a dosage ratio of the intermediate I-R-4c to the cesium carbonate and the anhydrous acetonitrile is 1 mmol:0.5 mmol to 2.5 mmol:3 mL to 10 mL, in some embodiments, the dosage ratio is 1 mmol:1.5 mmol:3 mL to 10 mL, in some embodiments, a temperature of the reaction is 0° C. to 40° C., and in some embodiments, the reaction lasts for 2 hours to 4 hours.

When $R_4$ is selected from the amino acid carboxylic ester group in formula I, in some embodiments, the preparation method of the cordycepin derivative as shown in formula I preferably comprises: reacting the compound I-R-4 with amino acid acyl chloride in anhydrous pyridine to prepare the cordycepin derivative as shown in formula I; in some embodiments, a dosage ratio of the compound I-R-4 to the amino acid acyl chloride and the pyridine is 10 mmol:5 mmol to 15 mmol:50 mL to 100 mL, in some embodiments, the dosage ratio is 10 mmol:10 mmol:50 mL to 100 mL, in some embodiments, a temperature of the reaction is 20° C. to 60° C., in some embodiments, the temperature is 40° C., and in some embodiments, the reaction lasts for 6 hours to 20 hours.

When $R_4$ is selected from the amino acid alkyl ester phenyl phosphonate group in formula I, in some embodiments, the preparation method of the cordycepin derivative as shown in formula I comprises: reacting the compound I-R-4 with phenyl p-toluenesulfonyloxymethyl phosphate substituted by a modifier amino acid alkyl ester in anhydrous N,N-dimethylformamide with NaH as a catalyst, in some embodiments, a dosage ratio of the compound I-R-4 to the modifier, the NaH and the anhydrous N,N-dimethylformamide is 0.1 mol:0.1 mol to 0.15 mol:0.2 mol to 0.03 mol:100 mL to 200 mL, in some embodiments, the dosage ratio is 0.1 mol:0.1 mol to 0.15 mol:0.2 mol to 0.03 mol:150 mL, in some embodiments, a temperature of the reaction is −20° C. to 0° C., and in some embodiments, the reaction lasts for 0.5 hour to 6 hours.

When $R_4$ is selected from the amino acid alkyl ester phenyl phosphonate group in formula I, in some embodiments, the preparation method of the cordycepin derivative as shown in formula I comprises: reacting the compound I-R-4 with nitrophenyl phosphate substituted by a modifier in anhydrous N,N-dimethylformamide and/or tetrahydrofuran with tert-butyl magnesium chloride as a catalyst, wherein the substitution refers to substituting with any one or more functional groups of aryloxy and methyl alkyl ester oxy, in some embodiments, a dosage ratio of the compound I-R-4 to the modifier, the catalyst and the organic solvent is 1 mmol:1 mmol to 3 mmol:1 mmol to 2 mmol:9 mL to 15 mL, in some embodiments, a temperature of the reaction is 20° C. to 40° C., and in some embodiments, the reaction lasts for 2 hours to 5 hours.

E. Modification of $R_5$

When $R_5$ is selected from the bromovinyl, the mercapto, the methyl, the fluorine, or the chlorine in formula I, the preparation method of the cordycepin derivative as shown in formula I comprises: using a compound I-R-5 as a raw material for a chemical reaction in an organic solvent to prepare the cordycepin derivative as shown in formula I;

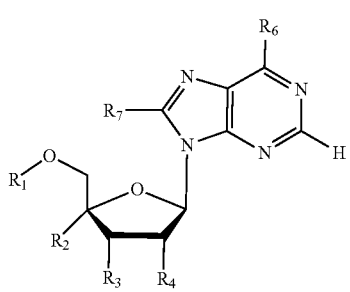

I-R-5 in formula I-R-5, $R_1$ to $R_4$ and $R_6$ to $R_7$ are the same as $R_1$ to $R_4$ and $R_6$ to $R_7$ in formula I, or are independently selected from protecting groups respectively.

When $R_5$ is selected from the bromovinyl in formula I, in some embodiments, the preparation method of the cordycepin derivative as shown in formula I comprises: subjecting the compound I-R-5 to an iodization reaction to prepare an intermediate I-R-5a, which is 2-(6-amino-2-iodine-1,6-dihydro-9H-purine-9-yl)-5-(hydroxymethyl)tetrahydrofuran-3-ol or a derivative thereof, subjecting the intermediate I-R-5a to a substitution reaction with methyl acrylate to prepare an intermediate I-R-5b, which is methyl(E)-3-(6-amino-3-hydroxy-5-(hydroxymethyl)tetrahydrofuran-2-yl)-6,9-dihydro-1H-purine-2-yl)acrylate or a derivative thereof, hydrolyzing the intermediate I-R-5b to prepare an intermediate I-R-5c, which is (E)-3-(6-amino-9-3-hydroxy-5-(hydroxymethyl)tetrahydrofuran-2-yl)-6,9-dihydro-1H-purine-2-yl)acrylic acid or a derivative thereof, and subjecting the intermediate I-R-5c to a bromination reaction with N-bromosuccinimide to prepare the cordycepin derivative as shown in formula I; in some embodiments, the preparation method of the intermediate I-R-5a comprises: subjecting the compound I-R-5 to an iodination reaction with iodine in dilute nitric acid to prepare the intermediate I-R-5a, in some embodiments, a dosage ratio of the compound I-R-5 to the iodine is 1 mmol:0.5 mmol to 0.8 mmol, in some embodiments, a temperature of the reaction is 100° C. to 120° C., in some embodiments, the temperature is 110° C., and in some embodiments, the reaction lasts for 4 hours to 6 hours; in some embodiments, the preparation method of the intermediate I-R-5b comprises: reacting the intermediate I-R-5a with methyl acrylate and triethylamine in under catalysis of palladium acetate and triphenylphosphine in 1,4-dioxane, in some embodiments, a dosage ratio of the intermediate I-R-5a to the methyl acrylate, the triethylamine, the palladium acetate, the triphenylphosphine and the 1,4-dioxane is 1 mmol:3 mmol to 4 mmol:0.1 mL to 0.5 mL:0.01 mmol to 0.09 mmol:0.05 mmol to 0.15 mmol:10 mL to 20 mL, in some embodiments, the dosage ratio is 1 mmol:3 mmol to 4 mmol:0.1 mL to 0.5 mL:0.05 mmol:0.01 mmol:10 mL to 20 mL, in some embodiments, a temperature of the reaction is 50° C. to 90° C., and in some embodiments, the reaction lasts for 0.5 hour to 2 hours; in some embodiments, the preparation method of the intermediate I-R-5c comprises: hydrolyzing the intermediate I-R-5b with a sodium hydroxide solution, in some embodiments, a concentration of the sodium hydroxide solution is 0.5 mol/L to 3.5 mol/L, in some embodiments, the concentration is 2 mol/L, in some embodiments, a dosage ratio of the intermediate I-R-5b to the sodium hydroxide solution is 1 g:10 mL to 14 mL, in some embodiments, the dosage ratio is 1 g:12 mL, in some embodiments, a temperature of the reaction is 20° C. to 30° C., in some embodiments, the temperature is room temperature, and in some embodiments, the reaction lasts for 3 hours to 5 hours; and in some embodiments, the preparation method of the cordycepin derivative as shown in formula I comprises: reacting the intermediate I-R-5c with N-bromosuccinimide under catalysis of potassium carbonate in a mixed solvent of water and acetone, in some embodiments, a dosage ratio of the intermediate I-R-5c to the N-bromosuccinimide, the potassium carbonate and the mixed solvent is 1 mmol:1 mmol to 3 mmol:1 mmol to 3 mmol:15 mL to 30 mL, in some embodiments, a volume ratio of the water to the acetone is 1:4 to 8, and in some embodiments, the volume ratio is 1:6.

I-R-5a

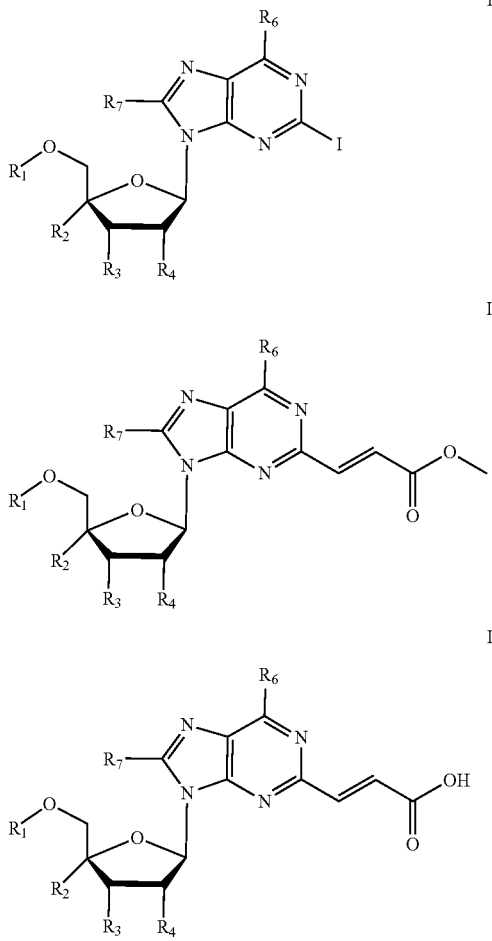

I-R-5b

I-R-5c

In some embodiments, the unmodified cordycepin is directly modified by bromovinyl, with a reaction path as follows:

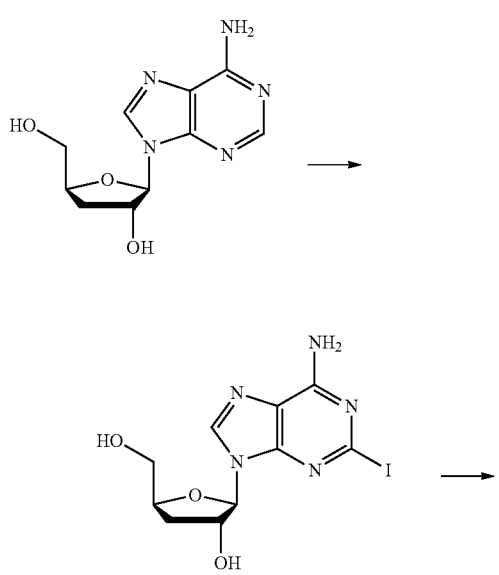

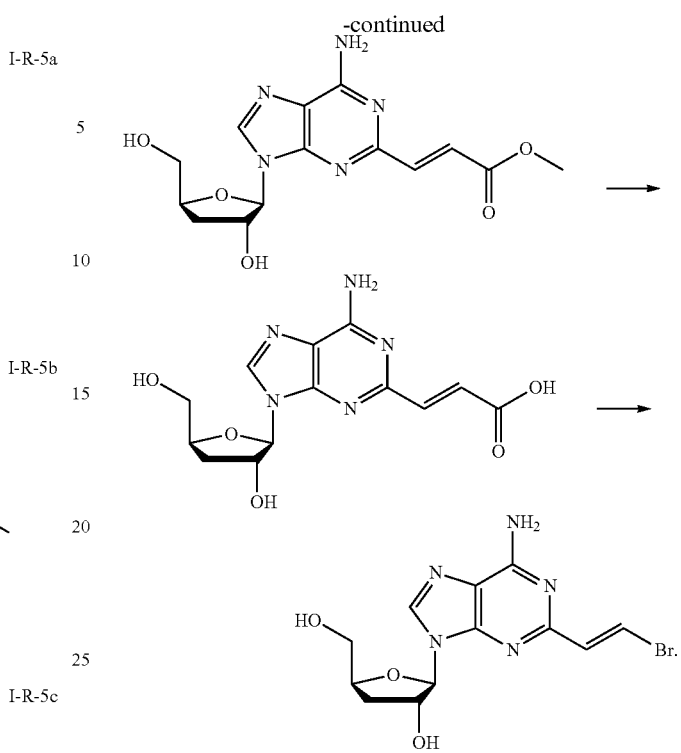

When $R_5$ is selected from the mercapto in formula I, in some embodiments, the preparation method of the cordycepin derivative as shown in formula I comprises: making the compound I-R-5 react with hydrogen peroxide in acetic acid to prepare an intermediate I-R-5d, which is 1N-oxidized-3'-deoxyadenosine or a derivative thereof, heating and refluxing the intermediate I-R-5d in a hydrochloric acid aqueous solution to prepare an intermediate I-R-5e, which is 5-amino-N'-hydroxy-3-hydroxy-5-(hydroxymethyl)tetrahydrofuran-2-yl)-1H-imidazole-4-carboxamide or a derivative thereof, dissolving the intermediate I-R-5e in water, making the mixture react in a hydrogen environment under catalysis of raney nickel to prepare an intermediate I-R-5f, which is 5-amino-3-hydroxy-5-(hydroxymethyl)tetrahydrofuran-2-yl)-1H-imidazole-4-carboxamide or a derivative thereof, and reacting the intermediate I-R-5f with methanol, methanol and carbon disulfide to prepare the cordycepin derivative as shown in formula I; in some embodiments, the preparation method of the intermediate I-R-5d comprises: making the compound I-R-5 react with the acetic acid in the hydrogen peroxide, in some embodiments, a concentration of the hydrogen peroxide is 20% to 40%, in some embodiments, the concentration is 30%, and in some embodiments, a dosage ratio of the compound I-R-5 to the hydrogen peroxide and the acetic acid is 1 mmol:2 mol to 3 mol:1 mL to 6 mL, in some embodiments, a temperature of the reaction is 30° C. to 50° C., and in some embodiments, the reaction lasts for 2 days to 4 days; in some embodiments, the preparation method of the intermediate I-R-5e comprises: heating and refluxing the intermediate I-R-5d in the hydrochloric acid aqueous solution, in some embodiments, a concentration of the hydrochloric acid aqueous solution is 1 mol/L to 5 mol/L, in some embodiments, the concentration is 3 mol/L, in some embodiments, a dosage ratio of the intermediate I-R-5d to the hydrochloric acid aqueous solution is 1 mmol:3 mL to 5 mL, and in some embodiments, the heating and refluxing last for 10 minutes to 30 minutes;

wherein, in the preparation method of the intermediate I-R-5f, in some embodiments, a dosage ratio of the intermediate I-R-5e to the raney nickel and the water is 1 mmol:0.08 g to 0.2 g:10 mL to 20 mL, in some embodiments, a temperature of the reaction is 50° C. to 70° C., and in some embodiments, the reaction lasts for 2 days to 5 days; and wherein, in the preparation method of the cordycepin derivative as shown in formula I, in some embodiments, a dosage ratio of the intermediate I-R-5f to the methanol, the pyridine and the carbon disulfide is 1 mmol:5 mL to 10 mL, in some embodiments, a volume dosage ratio of the methanol to the pyridine and the carbon disulfide is 4:3 to 7:0.5 to 3.5, in some embodiments, the volume dosage ratio is 4:5:2, in some embodiments, a temperature of the reaction is 30° C. to 50° C., in some embodiments, the temperature is 40° C., and in some embodiments, the reaction lasts for 3 days to 5 days.

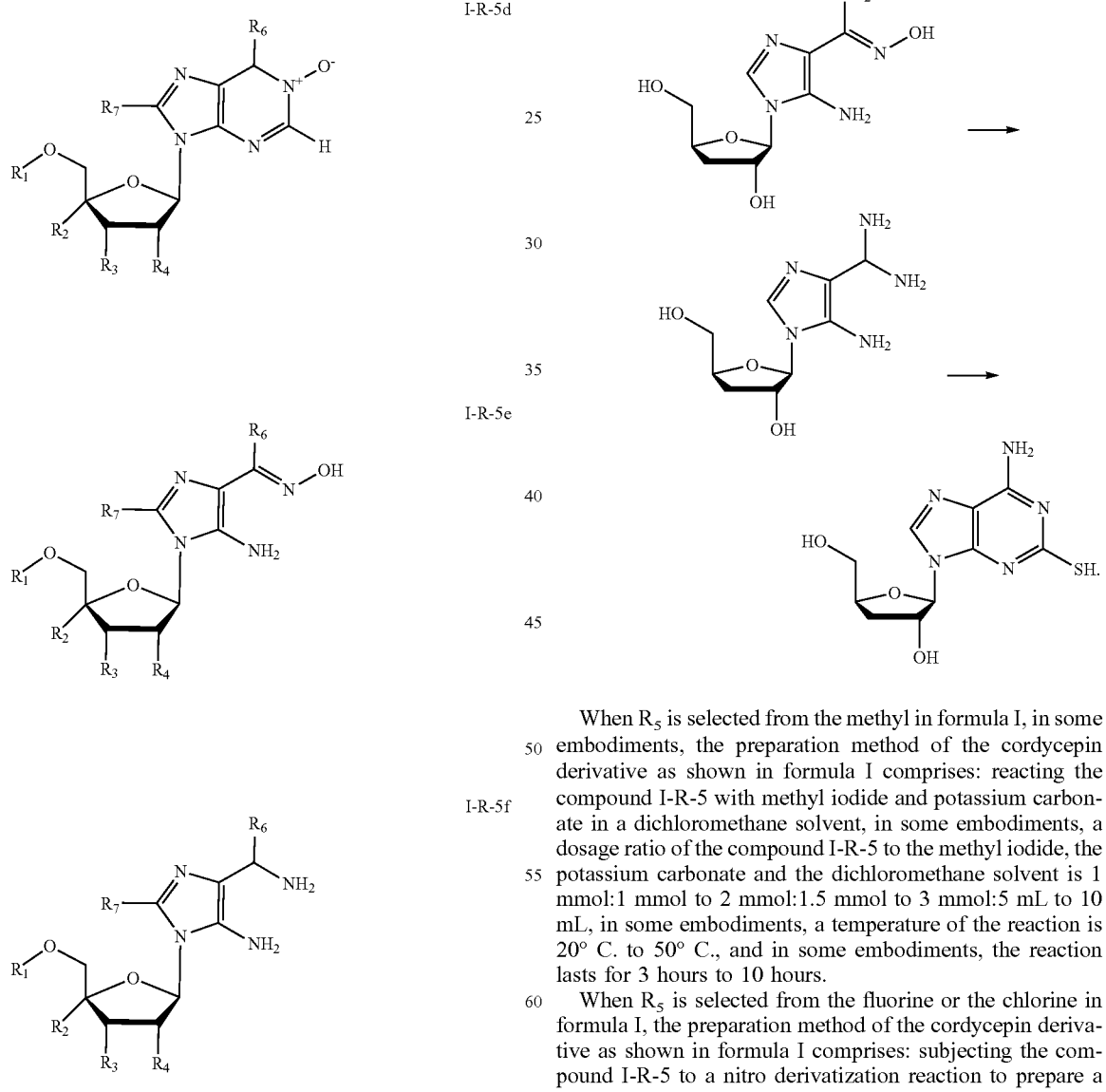

In some embodiments, the unmodified cordycepin is directly modified by sulfydryl, with a reaction method as follows:

When $R_5$ is selected from the methyl in formula I, in some embodiments, the preparation method of the cordycepin derivative as shown in formula I comprises: reacting the compound I-R-5 with methyl iodide and potassium carbonate in a dichloromethane solvent, in some embodiments, a dosage ratio of the compound I-R-5 to the methyl iodide, the potassium carbonate and the dichloromethane solvent is 1 mmol:1 mmol to 2 mmol:1.5 mmol to 3 mmol:5 mL to 10 mL, in some embodiments, a temperature of the reaction is 20° C. to 50° C., and in some embodiments, the reaction lasts for 3 hours to 10 hours.

When $R_5$ is selected from the fluorine or the chlorine in formula I, the preparation method of the cordycepin derivative as shown in formula I comprises: subjecting the compound I-R-5 to a nitro derivatization reaction to prepare a nitration intermediate I-R-5g, which is 2-(6-amino-2-nitro-1,6-dihydro-9H-purine-9-yl)-5-(hydroxymethyl)tetrahydrofuran-3-ol, and then subjecting the intermediate to a substitution reaction to prepare the cordycepin derivative as shown in formula I; in some embodiments, the preparation method of the intermediate I-R-5g comprises: reacting the compound I-R-5 with tetrabutylammonium nitrate under catalysis of trifluoroacetic anhydride in dichloromethane, in some embodiments, a dosage ratio of the compound I-R-5 to the tetrabutylammonium nitrate, the trifluoroacetic anhydride and the dichloromethane is 1 mmol:1.4 mmol to 2 mmol:1 mmol to 2 mmol:15 mL to 35 mL, in some embodiments, a temperature of the reaction is −10° C. to 10° C., and in some embodiments, the reaction lasts for 0.5 hour to 20 hours; in some embodiments, the preparation method of the cordycepin derivative as shown in formula I comprises: reacting the nitration intermediate I-R-5g with tetrabutylammonium fluoride or tetrabutylammonium chloride in acetonitrile, in some embodiments, a dosage ratio of the nitration intermediate I-R-5g to the tetrabutylammonium fluoride or the tetrabutylammonium chloride and the acetonitrile is 1 mmol:1.3 mmol to 1.5 mmol:30 mL to 50 mL, a temperature of the reaction is −5° C. to 5° C., in some embodiments, the temperature is 0° C., and in some embodiments, the reaction lasts for 20 minutes to 30 minutes.

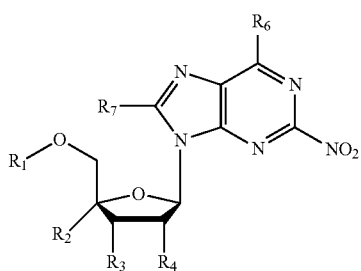

I-R-5g

F. Modification of $R_6$

When $R_6$ is selected from the formamido substituted in formula I, wherein the substitution refers to substituting with any one or more functional groups of alkyl, aryl, cycloalkyl, furyl and pyridyl; and the preparation method of the cordycepin derivative as shown in formula I comprises: using a compound I-R-6 as a raw material for a chemical reaction in an organic solvent to prepare the cordycepin derivative as shown in formula I;

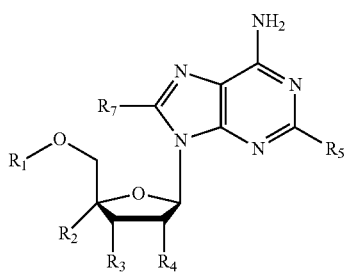

I-R-6 in formula I-R-6, $R_1$, $R_5$ and $R_7$ are the same as $R_1$, $R_5$ and $R_7$ in formula I, or are independently selected from protecting groups respectively.

In some embodiments, the preparation method of the cordycepin derivative as shown in formula I comprises: reacting the compound I-R-6 with acyl chloride substituted under anhydrous pyridine, wherein the substitution refers to substituting with any one or more functional groups of alkyl, aryl, cycloalkyl, furyl and pyridyl, in some embodiments, a dosage ratio of the compound I-R-6 to the acyl chloride substituted and the anhydrous pyridine is 1 mmol:1 mmol to 2 mmol:5 mL to 10 mL, in some embodiments, a temperature of the reaction is 0° C. to 60° C., and in some embodiments, the reaction lasts for 2 hours to 20 hours.

G. Modification of $R_7$

When $R_7$ is selected from the isopropyl amino in formula I, the preparation method of the cordycepin derivative as shown in formula I comprises: using a compound I-R-7 as a raw material for a chemical reaction in an organic solvent to prepare the cordycepin derivative as shown in formula I;

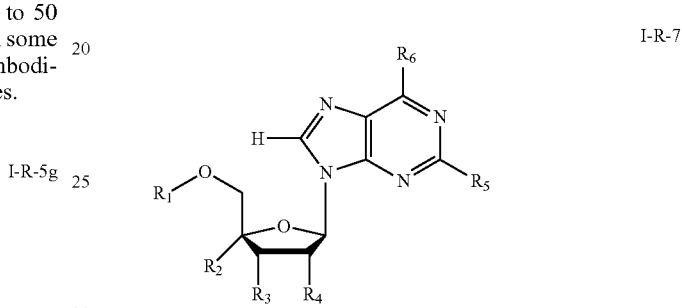

I-R-7 in formula I-R-7, $R_1$ to $R_6$ are the same as $R_1$ to $R_6$ in formula I, or are independently selected from protecting groups respectively.

In some embodiments, the preparation method of the cordycepin derivative as shown in formula I comprises: subjecting the compound I-R-7 to a substitution reaction with 2-propylamina in dioxane, in some embodiments, a dosage ratio of the compound I-R-7 to the 2-propylamina and the dioxane is 10 mmol:10 mmol to 30 mmol:50 mL to 100 mL, in some embodiments, a temperature of the reaction is 60° C. to 120° C., and in some embodiments, the reaction lasts for 10 hours to 30 hours.

In the present invention, the protecting groups comprise, but are not limited to, —OTBS, —OAc, —NHCbz, —OTBPS and —OTBDPS; in some embodiments, $R_4$ is the same as $R_4$ in formula I or is selected from —OTBS, —OAc and —OTBDPS; and in some embodiments, $R_6$ is the same as $R_6$ in formula I or is selected from —NHCbz.

In the present invention, the nitrophenyl phosphate substituted (the substitution refers to substituting with any one or more functional groups of alkoxyl, alkoxyl substituted by halogen, aryloxy, amino acid ester acylamino, alkyl ester group and methyl alkyl acid oxy) is prepared according to the following method or other methods in the prior art.

In anhydrous dichloromethane, phenyl chlorophosphate, p-nitrophenol and corresponding alcohol or amine substituted are prepared under catalysis of triethylamine at 0° C. to 25° C., wherein the substitution refers to substituting with any one or more functional groups of alkoxyl, alkoxyl substituted by halogen, aryloxy, amino acid ester acylamino, alkyl ester group and methyl alkyl acid oxy, in some embodiments, a molar volume ratio of the phenyl chlorophosphate to the p-nitrophenol, the corresponding substituent, the triethylamine and the anhydrous dichloromethane is 1 mmol:1 mmol:1 mmol to 2 mmol:2 mmol to 5 mmol:5 mL to 10 mL.

In the present invention, the p-toluenesulfonyloxymethyl phosphate substituted (the substitution refers to substituting with any one or more functional groups of alkoxyl, alkoxyl substituted by halogen, aryloxy, amino acid ester acylamino, alkyl ester group and methyl alkyl acid oxy) is prepared according to the following method or other methods in the prior art.

In toluene, corresponding chlorophosphate substituted, p-toluenesulfonyl chloride and formaldehyde are prepared under catalysis of triethylamine at 0° C. to 105° C., wherein the chlorophosphate substituted is chlorophosphate substituted by any one or more functional groups of alkoxyl, alkoxyl substituted by halogen, aryloxy, amino acid ester acylamino, alkyl ester group and methyl alkyl acid oxy, in some embodiments, a molar volume ratio of the corresponding chlorophosphate substituted to the p-toluenesulfonyl chloride, the formaldehyde, the triethylamine and the toluene is 1 mol:1 mol:0.8 mol to 1.2 mol:180 mL to 210 mL:500 mL to 800 mL.

Those skilled in the art can easily understand that $R_1$ to $R_7$ are modified with groups based on the cordycepin in the present invention, and when $R_1$ is hydrogen, $R_2$ is hydrogen, $R_3$ is hydrogen, $R_5$ is hydrogen, $R_7$ is hydrogen, $R_4$ is hydroxyl, or $R_6$ is amino, it is unnecessary to modify $R_1$ to $R_7$. In the preparation method of the present invention, the above substituents may be modified according to a priority order of stability of the prepared intermediates without violating the common sense in the art, so as to obtain various embodiments of the present invention, for example, modifications without ester group, phosphate group and phosphonate group may be carried out first, such as modifying —CN, —$N_3$, —F, —SH, and the like, then modification with ester group is carried out, and finally, modification with phosphate group or phosphonate group is carried out.

The term "prevention" in the present invention means that the compounds or preparations described in the present application are administered to prevent a disease or one or more symptoms related to the disease, and comprises: preventing a disease or a disease state from appearing in mammals, especially when these mammals are prone to induce related cancer symptoms.

The term "pharmaceutically acceptable" in the present invention aims at those compounds, materials, compositions and/or dosage forms, which are within the range of reliable medical judgment and are suitable for contact with human and animal tissues without excessive toxicity, irritation, allergic reaction or other problems or complications, thus being commensurate with a reasonable benefit/risk ratio.

The compounds of the present invention may exist in specific geometric or stereoisomeric forms. All such compounds are proposed in the present invention, comprising cis and trans isomers, (−)- and (+)-enantiomers, (R)- and (S)-enantiomers, diastereomers, (D)-isomers, (L)-isomers, racemic mixtures thereof and other mixtures, such as mixtures enriched with the enantiomers or the diastereomers, and all these mixtures are within the scope of the present invention. There may be other asymmetric carbon atoms in substituents such as alkyl. All these isomers and mixtures thereof are included in the scope of the present invention.

Beneficial effects: compared with the prior art, the present invention has the following advantages:

The cordycepin derivative and the pharmaceutical composition thereof provided by the present invention have a good anti-tumor proliferation effect. Compared with a parent drug, the cordycepin derivative has better affinity to cell membranes, so that a half-life period of in-vivo metabolism of the drug is longer, and in-vivo remaining time of the drug is longer. Compared with other nucleoside anti-tumor drugs, the cordycepin derivative and the pharmaceutical composition thereof provided by the invention have wider types and action ranges of tumors, have excellent inhibition effects on a gastric cancer, a pancreatic cancer, a liver cancer, a small cell lung cancer, a colorectal cancer, melanoma, an ovarian cancer and the like, and have lower side effects and better curative effects.

DETAILED DESCRIPTION

Figure 1:
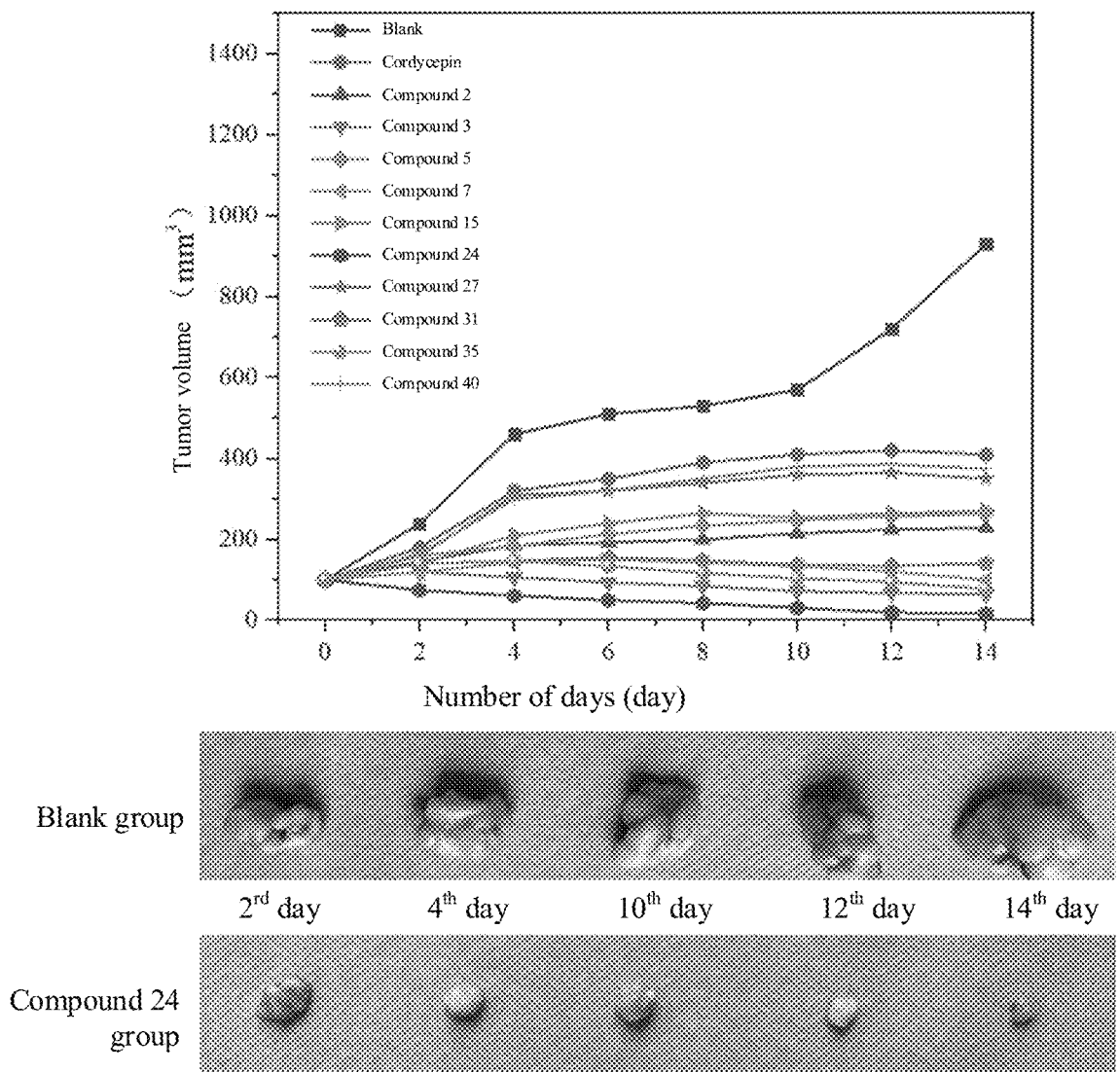
FIG. 1 shows anti-tumor effects of a blank group, a cordycepin control group and a compound group on a mouse model transplanted with liver cancer cells Hep-1-6.

The experimental methods described in the following embodiments are all conventional methods unless otherwise specified. The reagents and materials can all be obtained commercially unless otherwise specified. The cell models and animal models in the drug evaluation experiments can be obtained commercially unless otherwise specified.

The cordycepin in the present invention is prepared by biological fermentation (CN 111117896B), wherein the cordycepin or the derivative thereof is prepared according to the method in the specification, and the post-treatment method mainly adopts a conventional organic experiment post-treatment operation method which comprises, but is not limited to, filtration, quenching, extraction, rotary steaming, recrystallization, column chromatography and the like. The preparation methods of the compounds mentioned in the embodiments do not comprise all compounds, and only a few representative compounds are listed herein for the convenience of explanation.

In the embodiments, not all the animal model experiments on anti-cancer related cells of the cordycepin or the derivative thereof have effective experimental results, the animal model experiments are only related experiments listed to illustrate the effects, and the drug evaluation experiments comprise cell model and animal model experiments following ethical rules.

The feeding of the mouse model in the drug evaluation follows that: mice are fed and treated in a laminar flow cabinet, with 5 nude mice in each cage, drinking water and feedstuffs are added once every 3 days, and paddings are replaced once a week; a number of mice kept in each cage is no more than 5, the mice in separate cages are kept in groups as far as possible, and the mice should not be kept in a single cage; the animal management must conform to the relevant national standards on animal feeding management, and the behavioral needs of animals should be concerned at the same time to avoid unnecessary stress; the normal physiological and behavioral needs of animals, such as defecation, urination, constant body temperature maintenance, normal activities, posture adjustment and reproduction are met; good ventilation and dry animals are kept; the animals can access to drinking water and food at will, and supplementation, replacement and cleaning operations are easily carried out; a solid and safe environment is provided to avoid accidents of animals, such as escaping or limb trapping in a gap; the animals are avoided from being damaged by sharp edges or protrusions; and the animals are not disturbed during observation.

The zebrafish model is a wild-type AB-line zebrafish from College of Biotechnology and Pharmaceutical Engineering, Nanjing Tech University, and is carried out by a natural mating reproduction method, with 30 zebrafish of 2 dpf in each experimental group. The zebrafish is fed in fish culture water at 28° C. (water quality:200 mg of instant sea salt and $CaCO_3$ are added into 1 L of reverse osmosis water with a conductivity of 480 uS/cm to 510 uS/cm, a pH value of 6.9 to 7.2, and a hardness of 53.7 mg/L to 71.6 mg/L), and the feeding management meets the requirements of international AAALAC certification.

The method for determining inhibitory activities of the compounds on the proliferation of tumor cells by an MTT method is as follows: a bottle of cells in a good state in an exponential growth phase is added with 0.25% trypsin digestive juice, the digestion makes adherent cells fall off, with 2 to $4 \times 10^4$ cells/mL, and a cell suspension is prepared. The cell suspension is inoculated on a 96-well plate, with 90 μL/well, and cultured in a constant-temperature $CO_2$ incubator for 24 hours. The prepared compounds are added for testing, with 10 μL/well, and cultured for 72 hours. An MTT reagent is added into a 96-well plate, with 10 μL/well, and reacts in an incubator for 4 hours to absorb a supernatant, and then dimethyl sulfoxide is added, with 100 μL/well. After a crystal is dissolved, an absorbance of each well at a wavelength of 570 nm is measured by an enzyme-linked immunosorbent assay instrument, and a cell inhibition rate is calculated. An S curve is made with a compound concentration and a corresponding inhibition rate. Therefore, $IC_{50}$ of a corresponding compound is obtained.

Embodiment 1: Preparation of Compound: 2-(6-amino-9H-purin-9-yl)-5-(2-hydroxyethoxy)methyl)tetrahydrofuran-3-ol (1) Protection and Deprotection Methods for Hydroxyl in Cordycepin 1a protection and deprotection methods for hydroxyl at $R_1$ and $R_4$ sites of cordycepin were as follows.

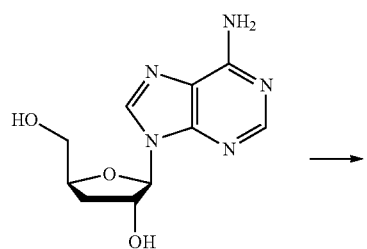

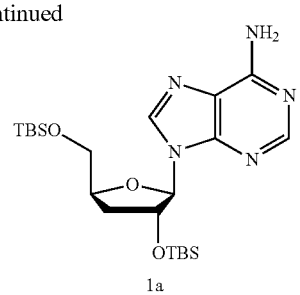

1a

Protection: 0.251 g (1 mmol) of cordycepin, 0.3618 g (2.4 mmol) of TBSCL and 0.3404 g (5 mmol) of imidazole were added into 10 mL of DMF, stirred at room temperature for 10 hours, and extracted with water and ethyl acetate after the reaction, and an organic phase was concentrated to obtain 0.4607 g of 1a, with a yield of 96.03%, and MSI-MS: 480.8 $[M+H]^+$.

Deprotection: 10 mL of (tetrabutylammonium fluoride: THF=2:1) solvent was prepared, added with 0.48 g (1 mmol) of 1a, stirred at room temperature for 5 hours, and extracted with water and ethyl acetate after the reaction, and an organic phase was concentrated, and recrystallized to obtain 0.246 g of cordycepin, with a yield of 97.96%.

1b protection and deprotection methods for hydroxyl at $R_1$ site of cordycepin were as follows.

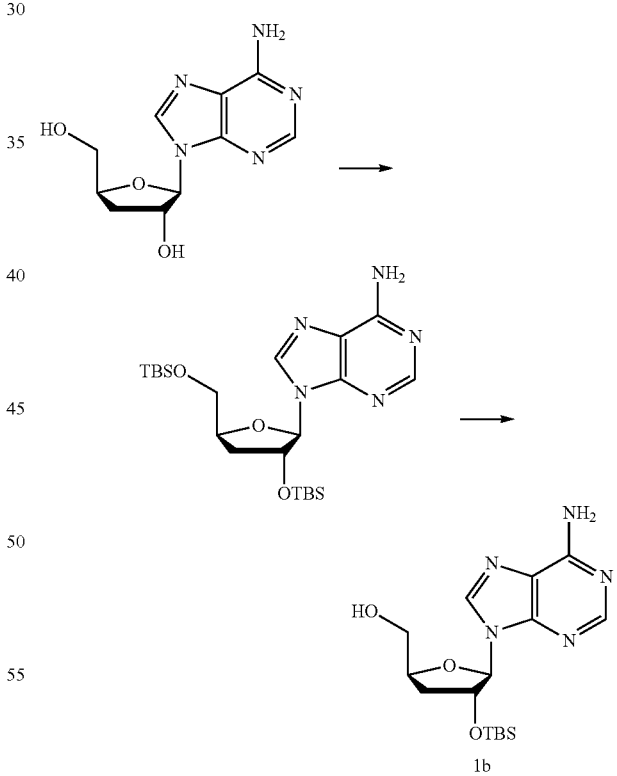

1b

Protection: 0.251 g (1 mmol) of cordycepin, 0.3618 g (2.4 mmol) of TBSCL and 0.3404 g (5 mmol) of imidazole were added into 10 mL of DMF, stirred at room temperature for 10 hours, and extracted with water and ethyl acetate after the reaction, and an organic phase was concentrated to obtain 0.4607 g of 1a, with a yield of 96.03%. In addition, subsequently, 10 mL of (acetic acid:water:THF=13:7:3.)

solvent was prepared, added with 0.48 g (1 mmol) of 1a, stirred at room temperature for 15 hours, and extracted with water and ethyl acetate after the reaction, and an organic phase was concentrated, and subjected to column chromatography to obtain 0.293 g of 1b, with a yield of 79.99%, MSI-MS: 366.5 $[M+H]^+$.

Deprotection: 10 mL of 0.1 M hydrochloric acid methanol solution was added with 0.366 g (1 mmol) of 1b, and stirred at room temperature for 10 hours, pH of the mixture was adjusted to be neutral with 0.1 M sodium carbonate aqueous solution after the reaction, the mixture was extracted with ethyl acetate, and an organic phase was concentrated, rotationally evaporated and recrystallized to obtain 0.215 g of cordycepin, with a yield of 85.56%.

1c protection and deprotection methods for hydroxyl at $R_4$ site of cordycepin were as follows.

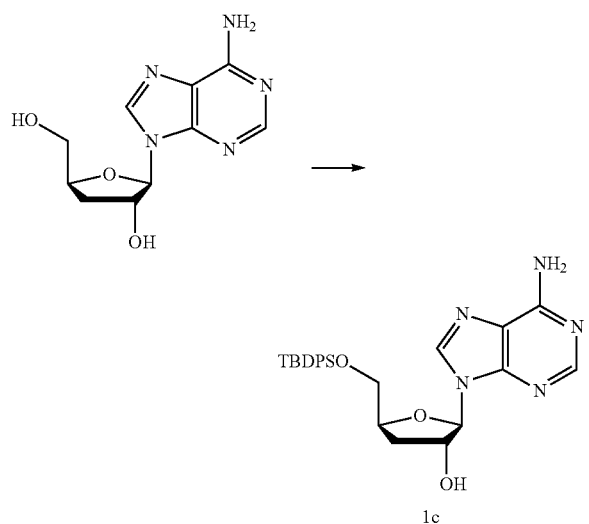

Protection: 1.256 g (5 mmol) of cordycepin was added into 10 mL of dichloromethane and 10 mL of diisopropylethylamine under protection of nitrogen, then dropwise added with 0.451 g (1.6 mmol) of TBDPSCl, stirred at room temperature for 2 hours, concentrated and then purified by column chromatography to obtain 2.20 g of 1c, with a yield of 89.9%, and MSI-MS: 366.5 $[M+H]^+$.

Deprotection: 10 mL of (tetrabutylammonium fluoride: THF=2:1) solvent was prepared, added with 0.490 g (1 mmol) of 1c, stirred at room temperature for 5 hours, and extracted with water and ethyl acetate after the reaction, and an organic phase was concentrated, and recrystallized to obtain 0.244 g of cordycepin, with a yield of 97.01%.

(2) Specific Preparation Method of Compound: 2-(6-amino-9H-purin-9-yl)-5-(2-hydroxyethoxy)methyl)tetrahydrofuran-3-ol The compound 1b was used as a raw material, 3.65 g (10 mmol) of 1b and 0.81 g (10 mmol) of compound 2-chloroethanol were placed in a round-bottomed flask, and added with 60 mL of butanone, and the reactant was heated and dissolved, and additionally added with 2.07 g (15 mmol) of potassium carbonate. The reaction was carried out at 80° C. for 8 hours, and the reaction was monitored by TLC. The reaction solution was filtered and concentrated after the reaction, and extracted twice with 60 mL of water and 60 mL of ethyl acetate, organic phases were combined, and rotationally evaporated under a reduced pressure to obtain a viscous liquid, and the viscous liquid was deprotected and subjected to column chromatography to obtain a compound 1, with a weight of 2.24 g and a yield of 76%. Detection results of the prepared compound 1 were as follows: $^1$H NMR (400 MHz, DMSO-d6) δ8.56 (s, 1H), 8.35 (s, 1H), 7.09 (s, 2H), 6.14 (d, 1H), 5.47-5.3 (d, 2H), 5.01 (m, 1H), 4.12 (m, 1H), 3.74 (m, 1H), 3.61-3.56 (m, 4H), 3.51-3.46 (m, 2H), 2.04-1.92 (m, 2H). $^{13}$C NMR (100 MHz, DMSO-d6) δ156.1, 152.4, 149.8, 140.1, 119.6, 95.2, 82.1, 75.2, 74.7, 70.4, 61.1, 34.5. MSI-MS: 296.3 $[M+H]^+$.

Embodiment 2: Preparation of Compound: (5-(6-amino-9H-purine-9-yl)-4-hydroxytetrahydrofuran-2-yl)dihydromethyl phosphate According to the protection method in Embodiment 1, 3.65 g (10 mmol) of compound 1b was added with 150 mL of triethyl phosphite and 4.62 g (30 mmol) of phosphorus oxychloride in ice bath. The reaction was carried out at 0° C. for 2 hours, after the reaction, the mixture was added with 1,000 mL of water in the ice bath for a quenching reaction, and added with dichloromethane for multiple extractions, organic phases were combined, and rotationally evaporated to remove a solvent, so as to obtain a viscous liquid, the prepared viscous liquid was separated and purified by a preparative liquid phase (C18 preparative column, Waters preparative liquid phase, mobile phase of 30% acetonitrile aqueous solution, flow rate of 2 mL/min), and an effluent of a peak segment of a sample was concentrated and then weighed to obtain a phosphorylated compound, which was 3.02 g in total, with a yield of 70%.

A compound 2 was prepared according to the deprotection solution of 1b in Embodiment 1. Detection results of the prepared compound 2 were as follows: $^1$H NMR (400 MHz, DMSO-d6) δ8.54 (s, 1H), 8.36 (s, 1H), 7.11 (s, 2H), 6.19 (d, 1H), 5.15 (d, 1H), 4.28-4.23 (m, 2H), 4.2 (s, 2H), 4.02 (m, 1H), 3.71 (m, 1H), 2.06-1.90 (m, 2H). $^{13}$C NMR (100 MHz, DMSO-d6) δ156.2, 152.7, 149.5, 140.2, 119.3, 97.2, 76.1, 74.6, 69.5, 34.5. MSI-MS: 332.2 $[M+H]^+$.

Embodiment 3: ((((5-(6-amino-9H-purine-9-yl)-4-hydroxytetrahydrofuran-2-yl)methoxy)methyl)phosphonic acid

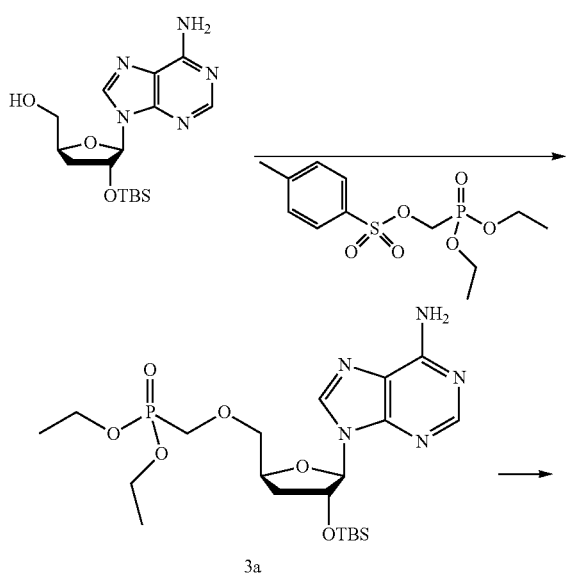

3a

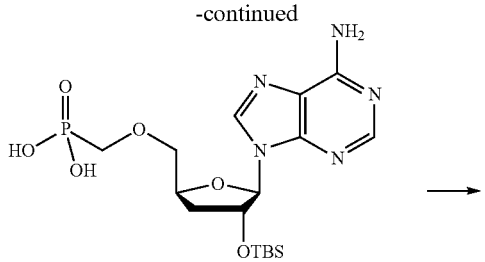

3b

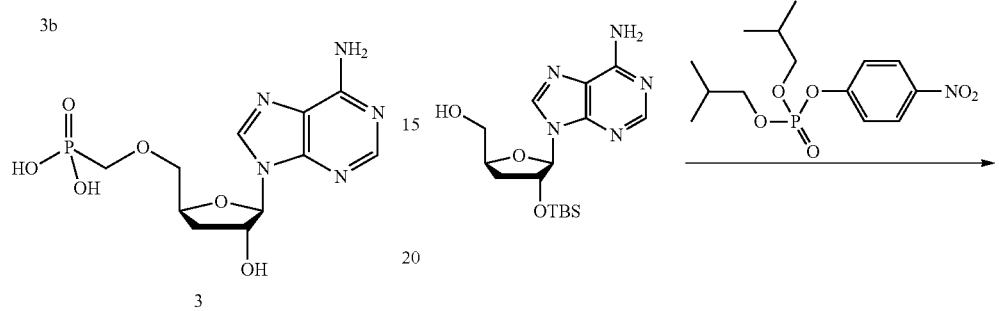

3

δ156.7, 152.6, 149.1, 140.4, 119.5, 98.2, 81.1, 76.3, 74.3, 73.1, 34.7. MSI-MS: 346.3 [M+H]$^+$.

Embodiment 4: Preparation of Compound: (5-(6-amino-9H-purine-9-yl)-4-hydroxytetrahydrofuran-2-yl)diisobutyl methylphosphate

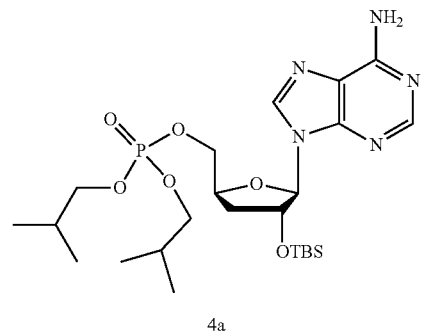

4a 36.5 g (100 mmol) of compound 1b was added into a 500 mL reaction flask, added with 150 mL of DMF as a solvent, and heated and dissolved. After rapid cooling to room temperature, 6.4 g (267 mmol) of 80% NaH was added in batches under stirring, and stirred at room temperature for 15 minutes. The reaction solution was cooled to −10° C. in a low-temperature reactor, dropwise added with 45.1 g (140 mmol) of diethyl p-toluenesulfonyloxymethyl phosphate, stirred for reaction at this temperature for 1 hour after dropwise adding, and then gradually subjected to temperature rise to room temperature and stirred for 4 hours. After the reaction, glacial acetic acid was dropwise added to adjust pH to be neutral, the reaction solution was filtered, and washed with dichloromethane, the filtrate was extracted with water (60 mL) thrice, dichloromethane phases were combined, and evaporated under a reduced pressure to remove a solvent, and toluene was added into the residue for recrystallization. A crystallization mother liquor was filtered, the filter cake was dried at 50° C. under a reduced pressure to obtain a white powdery solid 3a, with a weight of 26.87 g and a yield of 52%, and MSI-MS: 540.6 [M+23]$^+$.

5.17 g (10 mmol) of compound 3a was added into a 100 mL reaction flask, added with 20 mL of n-butyronitrile, and dropwise added with 6.52 g (60 mmol) of trimethylchlorosilane at room temperature, and the reaction solution was subjected to temperature rise and refluxed for reaction for 24 hours after dropwise adding. The solvent was concentrated to be dry by distillation under a reduced pressure after the reaction, 20 mL of water was added into the residue, 2 M sodium hydroxide was additionally added to adjust pH of the mixture to be about 8, then the mixture was extracted thrice with ethyl acetate (50 mL), and a water phase was neutralized with 1 M hydrochloric acid to make pH equal to 3 to 4. Subsequently, the mixture was heated to 70° C. to 80° C. for crystallization to obtain a compound 3b, with a weight of 3.40 g and a yield of 74%, and MSI-MS: 460.6 [M+H]$^+$.

The compound 3b was treated according to the deprotection solution of 1b in Embodiment 1 to obtain a compound 3. Detection results of the prepared compound were as follows: $^1$H NMR (400 MHz, DMSO-d6) δ8.58 (s, 1H), 8.32 (s, 1H), 7.13 (s, 2H), 6.12 (d, 1H), 5.39 (d, 1H), 4.81 (s, 2H), 4.02 (m, 1H), 3.98 (m, 1H), 3.74 (d, 2H), 3.63-3.56 (m, 2H), 2.08-1.94 (m, 2H). $^{13}$C NMR (100 MHz, DMSO-d6)

3.65 g (10 mmol) of compound 1b was added into a 500 mL reaction flask, dissolved in 100 mL of anhydrous DMF, and additionally added with 4.96 g (15 mmol) of diisobutyl phosphate(4-nitrophenyl). In addition, 1.17 g (10 mmol) of tert-butyl magnesium chloride was dissolved in 20 mL of THF, and the solution was slowly dropwise added into the reaction solution above. The reaction solution was gradually subjected to temperature rise to room temperature for reaction for 2 hours, and the reaction was monitored by a TLC plate. After the reaction, the obtained mixture was allowed to stand for reaction, diluted with 100 mL of ethyl acetate, washed and extracted thrice with saturated sodium bicarbonate aqueous solution, with 50 mL each time, and then extracted with 50 mL of saturated sodium chloride aqueous solution. An organic layer was dried on anhydrous sodium sulfate, and concentrated under a reduced pressure. The obtained oil was purified by silica gel column chromatography (eluent:dichloro/methanol=10:1) to obtain a compound 4a, with a weight of 4.24 g and a yield of 76%.

The 4a was treated according to the deprotection method of 1b in Embodiment 1 to obtain a compound 4. Detection results of the prepared compound 4 were as follows: $^1$H NMR (400 MHz, DMSO-d6) δ8.52 (s, 1H), 8.31 (s, 1H), 7.11 (s, 2H), 6.15 (d, 1H), 5.33 (d, 1H), 4.24-4.05 (m, 2H), 4.02 (m, 1H), 3.93 (m, 4H), 3.77 (m, 1H), 2.08-1.83 (m, 2H), 1.33 (m, 2H), 0.90 (d, 12H). $^{13}$C NMR (100 MHz, DMSO-d6) δ154.3, 151.7, 148.4, 141.9, 119.2, 98.2, 74.1, 74.0, 73.5, 68.1, 34.2, 28.6, 19.5. MSI-MS: 466.7 [M+Na]$^+$.

Embodiment 5: Preparation of Compound: (((((((5-(6-amino-9H-purine-9-yl)-4-hydroxytetrahydro-furan-2-yl)methoxy)methyl)phosphoryl) bis(oxy)bis(methylene)bis(2-methylpropionic acid))

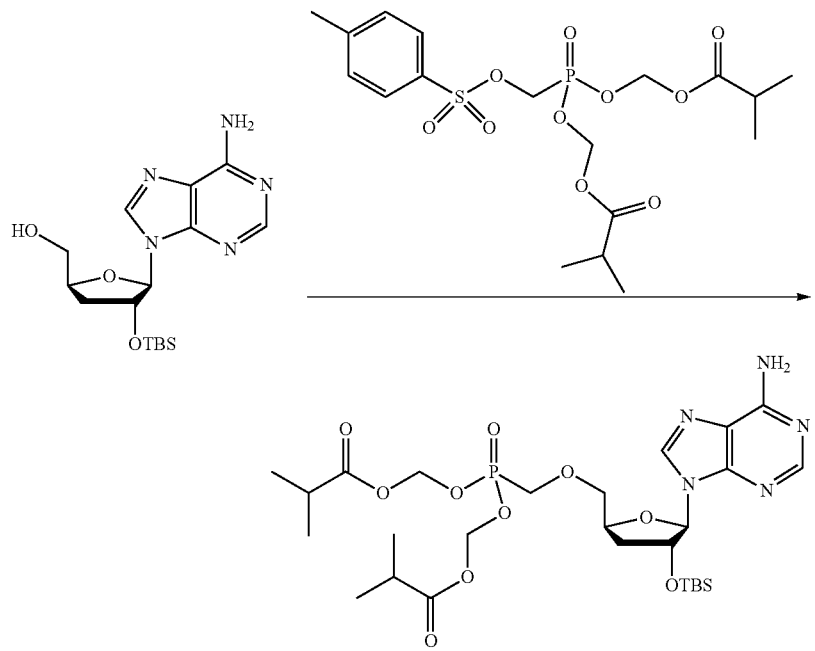

A compound 5 was prepared according to the preparation method of 3a in Embodiment 3 in combination with the deprotection method of 1b in Embodiment 1, wherein diethyl p-toluenesulfonyloxymethyl phosphate was replaced by ((tolyloxy)methyl)phosphoryl)bis(oxy))bis(methylene) bis(2-methylpropionic acid) in equivalent amount, and a total yield of the prepared compound 5 was 74%. Detection results of the prepared compound 5 were as follows: $^1$H NMR (400 MHz, DMSO-d6) δ8.57 (s, 1H), 8.33 (s, 1H), 7.11 (s, 2H), 6.84 (d, 4H), 6.18 (d, 1H), 5.46 (d, 1H), 4.12 (m, 1H), 3.94 (m, 1H), 3.81 (d, 2H), 3.60-3.44 (m, 2H), 2.55 (m, 2H), 2.08-1.82 (m, 2H), 1.14 (d, 12H). $^{13}$C NMR (100 MHz, DMSO-d6) δ174.2, 155.7, 153.6, 149.5, 141.2, 119.5, 99.4, 93.2, 77.4, 74.5, 74.1, 71.5, 34.2, 33.6, 19.3. MSI-MS: 546.5 [M+H]$^+$.

Embodiment 6: Preparation of Compound: methyl ((5-(6-amino-9H-purin-9-yl)-4-hydroxytetrahydro-furan-2-yl)methoxy)(phenoxy)phosphoryl)-D-valine, with a Preparation Process as Follows -continued

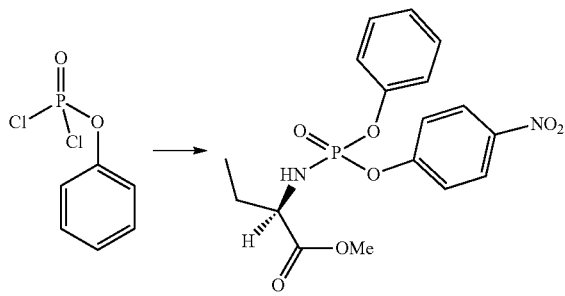

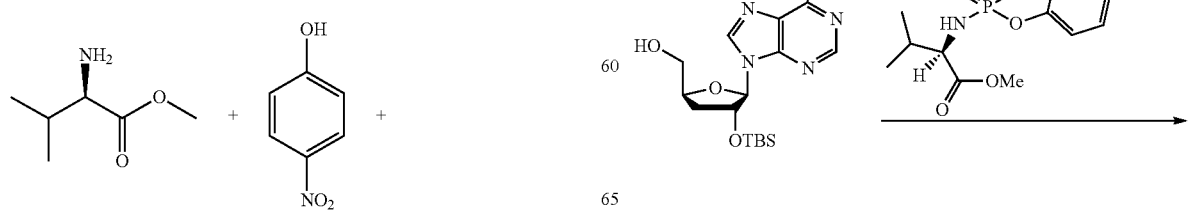

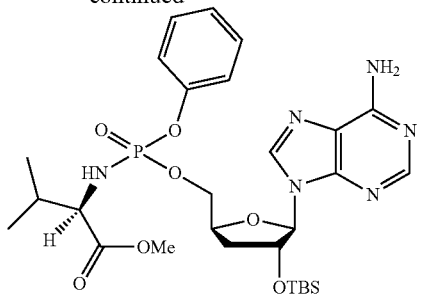

A preparation method of methyl((4-nitrophenoxy)(phenoxy)phosphoryl)-D-valine was as follows.

1.17 g (10 mmol) of valine was dissolved in 50 mL of dichloromethane. The solution was cooled to about 0° C., added with 2.11 g (10 mmol) of phenyl phosphate dichloride, and then slowly dropwise added with 2.02 g (20 mmol) of triethylamine, the reaction was subjected to temperature rise to room temperature, and the mixture was stirred for 80 minutes. 1.39 g (10 mmol) of reactant p-nitrophenol was added, then dropwise added with 2.02 g (20 mmol) of triethylamine, and stirred at room temperature for 180 minutes. After the reaction, the mixture was washed with ether, and filtered to remove a generated solid. The filtrate was concentrated on a rotary evaporator, and an obtained sample was purified by silica gel column chromatography (eluent:n-hexane/ethyl acetate (1:1)). Detection results of the prepared compound were as follows: $^1$H NMR (400 MHz, DMSO-d6) δ8.25 (d, 2H), 7.40 (m, 2H), 7.35 (d, 2H), 7.20 (m, 3H), 3.68 (s, 1H), 3.65 (s, 3H), 3.35 (m, 1H), 1.90 (m, 2H), 0.86 (m, 3H). $^{13}$C NMR (100 MHz, DMSO-d6) δ171.6, 156.5, 150.5, 141.1, 130.2, 126.5, 121.7, 121.4, 120.4, 52.2, 51.9, 26.4, 9.6. MSI-MS: 395.3 [M+H]$^+$.

A compound 6 was prepared according to the preparation method of 4a in Embodiment 4 in combination with the deprotection method of 1b in Embodiment 1, wherein diisobutyl p-phosphate(4-nitrophenyl) was replaced by methyl((4-nitrophenoxy)(phenoxy)phosphoryl)-D-valine in equivalent amount, and a yield of the prepared compound 6 was 68%. Detection results of the finally prepared compound 6 were as follows: $^1$H NMR (400 MHz, DMSO-d6) δ8.58 (s, 1H), 8.33 (s, 1H), 7.43 (m, 2H), 7.20 (m, 3H) 7.08 (s, 2H), 6.15 (d, 1H), 5.47 (d, 1H), 4.26-4.12 (m, 2H), 4.02 (m, 1H), 3.75 (m, 1H), 3.67 (d, 1H), 3.62 (s, 3H), 3.28 (d, 1H), 2.41 (m, 1H), 2.08-1.96 (m, 2H), 0.98 (d, 6H). $^{13}$C NMR (100 MHz, DMSO-d6) δ173.6, 154.9, 151.5, 150.6, 149.8, 141.3, 132.7, 123.3, 120.8, 119.2, 98.2, 76.1, 74.5, 72.0, 57.6, 52.3, 35.2, 32.4, 20.1. MSI-MS: 521.4 [M+H]$^+$.

Embodiment 7: Preparation of Compound: isopropyl((((((5-(6-amino-9H-purin-9-yl)-4-hydroxytetrahydrofuran-2-yl)methoxy)methyl)(phenoxy)phosphoryl)alanine ester, with a Preparation Process as Follows

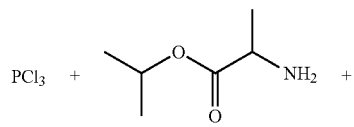

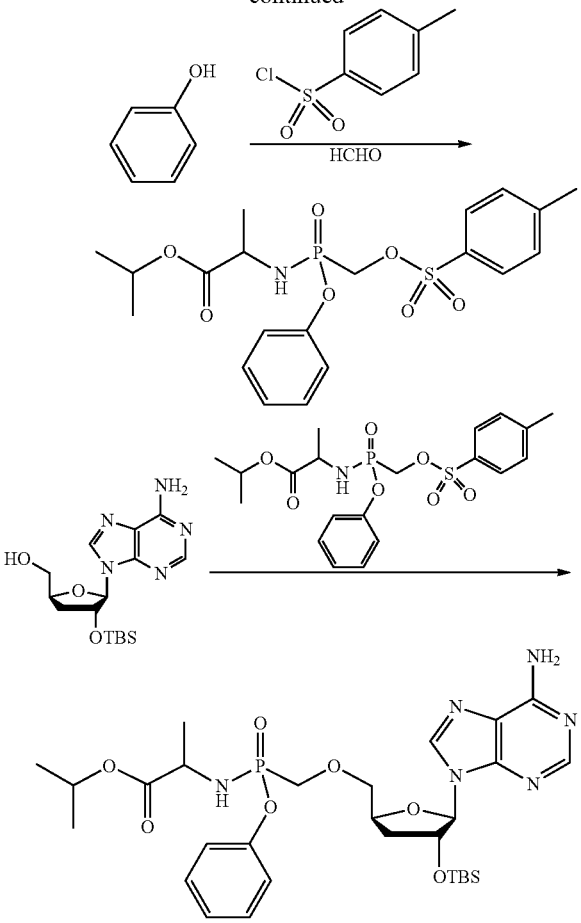

A preparation method of isopropyl(phenoxy((tolyloxy)methyl)phosphoryl)alanine ester was as follows.

216.15 g (1.65 mol) of isopropyl alanine, 155 g (1.65 mol) of phenol and 240 mL of chloroform were added into a 1,000 mL reaction flask, and stirred at about 5° C. in ice salt bath and then dropwise added with 138.8 g (1 mol) of phosphorus trichloride, and a reaction temperature was kept at 5° C. to 10° C. After dropwise adding the phosphorus trichloride, the mixture was continuously stirred for 30 minutes and removed from the ice salt bath, and gradually subjected to temperature rise to room temperature and continuously stirred for 2 hours, and then, hydrogen chloride gas was removed under a reduced pressure at 50° C. The reaction was cooled to room temperature, the mixture was slowly added with 80 mL of saturated sodium bicarbonate aqueous solution, and then added with sodium bicarbonate solid powder to adjust a pH value of the reaction solution to be 7 to 8. Precipitated salt was removed by filtering, the filtrate was placed in a separatory funnel to separate a chloroform layer, a water layer was extracted with 100 mL of chloroform once, organic phases were combined, and washed with saturated sodium bicarbonate solution and water once in sequence, the chloroform layer was distilled under a reduced pressure, and the residue was a target product phenyl chlorophosphate alanine isopropyl ester, with a yield of 87%.

306 g (1 mol) of phenyl chlorophosphate alanine isopropyl ester, 40.6 g (1.35 mol) of paraformaldehyde, 14 mL of triethylamine and 260 mL of toluene were put into a 1,000 mL reaction flask. The reaction was slowly subjected to temperature rise to 105° C. under protection of nitrogen, the reaction was intense at the moment, and the mixture was refluxed for reaction for 3 hours. After the reaction, the ice salt bath was cooled to 0° C., the mixture was added with 169.5 g (0.9 mol) of p-toluenesulfonyl chloride, added with 220 mL of toluene, and additionally dropwise added with 177 mL of triethylamine, the reaction temperature was kept at 0° C. and the mixture was stirred for 2 hours, and the mixture was gradually subjected to temperature rise to room temperature and stirred for 12 hours. The mixture was filtered after the reaction, the filter cake was washed with toluene (50 mL×3), and mother liquors were combined and washed with 5% sodium carbonate aqueous solution (200 mL×2) and water (200 mL×2) in sequence, and then layered to obtain an organic phase. The organic phase was distilled under a reduced pressure to obtain a light yellow oil substance, which was isopropyl(phenoxy((tolyloxy)methyl) phosphoryl)alanine ester and used for subsequent reaction, with a weight of 291 g and a yield of 64%. Detection results of the prepared compound were as follows: $^1$H NMR (400 MHz, DMSO-d6) δ7.74 (d, 2H), 7.45-7.39 (m, 4H), 7.22 (m, 3H), 4.95 (m, 1H), 3.91 (d, 2H), 3.65 (s, 1H), 3.57 (m, 1H), 2.42 (s, 3H), 1.28 (d, 3H), 1.18 (d, 6H). $^{13}$C NMR (100 MHz, DMSO-d6) δ171.6, 150.4, 144.4, 140.3, 130.5, 130.1, 128.5, 121.4, 120.2, 69.6, 63.8, 50.5, 21.7, 21.5, 19.2. MSI-MS: 456.5 [M+H]$^+$.

A compound 7 was prepared according to the preparation method of 3a in Embodiment 3 in combination with the deprotection method of 1b in Embodiment 1, wherein diethyl p-toluenesulfonyloxymethyl phosphate was replaced by the isopropyl(phenoxy((tolyloxy)methyl)phosphoryl)alanine ester in equivalent amount, and a yield of the prepared compound 7 was 52%. Detection results of the prepared compound 7 were as follows: $^1$H NMR (400 MHz, DMSO-d6) δ8.59 (s, 1H), 8.37 (s, 1H), 7.45 (m, 2H), 7.24 (m, 3H), 7.12 (s, 2H), 6.16 (d, 1H), 5.33 (d, 1H), 4.98 (m, 1H), 4.08-3.99 (m, 2H), 3.84 (m, 1H), 3.77 (m, 2H), 3.58-3.42 (m, 3H), 2.08-1.96 (m, 2H), 1.29 (d, 3H), 1.16 (d, 6H). $^{13}$C NMR (100 MHz, DMSO-d6) δ172.1, 156.3, 152.5, 150.4, 149.8, 140.1, 130.2, 122.1, 120.5, 119.1, 98.2, 79.1, 74.8, 74.7, 73.1, 69.6, 52.3, 34.5, 22.5, 18.8. MSI-MS: 535.6 [M+H]$^+$.

Embodiment 8: 2-(-5-(6-amino-9H-purin-9-yl)-4-hydroxytetrahydrofuran-2-yl)methoxy)-3-hydroxypropyl valine salt

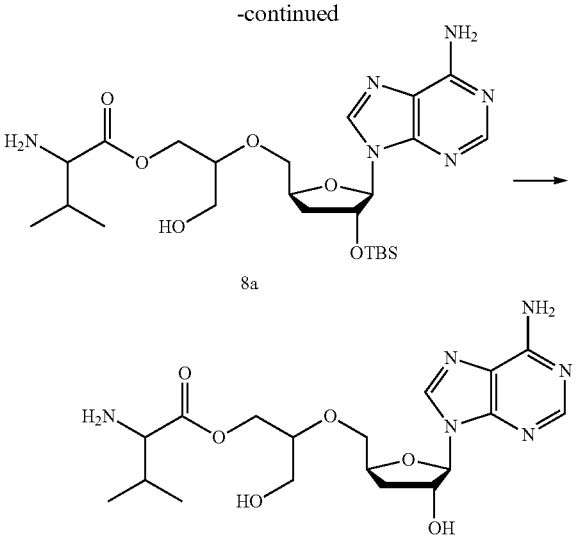

A compound 1b was used as a raw material, 3.65 g (10 mmol) of 1b and 2.10 g (10 mmol) of compound 2-chloro-3-hydroxypropyl valine were placed in a round-bottomed flask, and added with 60 mL of butanone, and the reactant was heated and dissolved, and additionally added with 2.07 g (15 mmol) of potassium carbonate. The reaction was carried out at 80° C. for 10 hours, and the reaction was monitored by TLC. The reaction solution was filtered and concentrated after the reaction, and extracted twice with 60 mL of water and 60 mL of ethyl acetate, organic phases were combined, and rotationally evaporated under a reduced pressure to obtain a viscous liquid, and the viscous liquid was subjected to column chromatography to obtain a compound 8a, with a weight of 3.24 g and a yield of 52%, and MSI-MS: 539.6 [M+H]$^+$.

The compound 8a was used as a substrate, which was treated by the deprotection method of 1b in Embodiment 1 to prepare a compound 8, with a yield of 91%. Detection results of the prepared compound 8 were as follows: $^1$H NMR (400 MHz, DMSO-d6) δ8.88 (s, 2H), 8.54 (s, 1H), 8.37 (s, 1H), 7.14 (s, 2H), 6.18 (d, 1H), 5.57 (d, 1H), 4.33-4.11 (m, 3H) 4.03 (m, 1H), 3.96-3.89 (m, 3H), 3.61-3.36 (m, 4H), 2.37 (m, 1H), 2.08-1.82 (m, 2H), 0.98 (d, 6H). $^{13}$C NMR (100 MHz, DMSO-d6) δ173.5, 154.6, 153.5, 150.4, 141.3, 119.6, 99.5, 85.6, 75.7, 74.0, 73.1, 63.3, 62.5, 58.7, 34.7, 30.8, 18.8. MSI-MS: 425.4 [M+H]$^+$.

Embodiment 9: Preparation of Compound: (4-amino-6-(6-amino-9H-purin-9-yl)-2,2-dioxide-1,7-dioxane-2-thiaspiro[4.4]non-3-ene-8-yl)dihydromethyl phosphate, with a Preparation Method as Follows

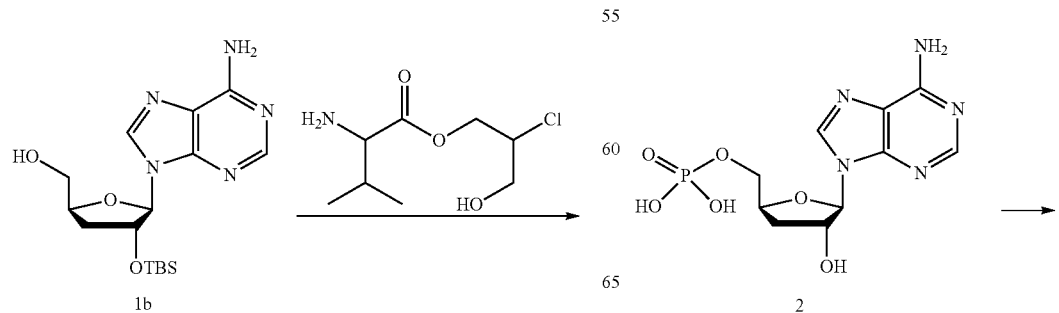

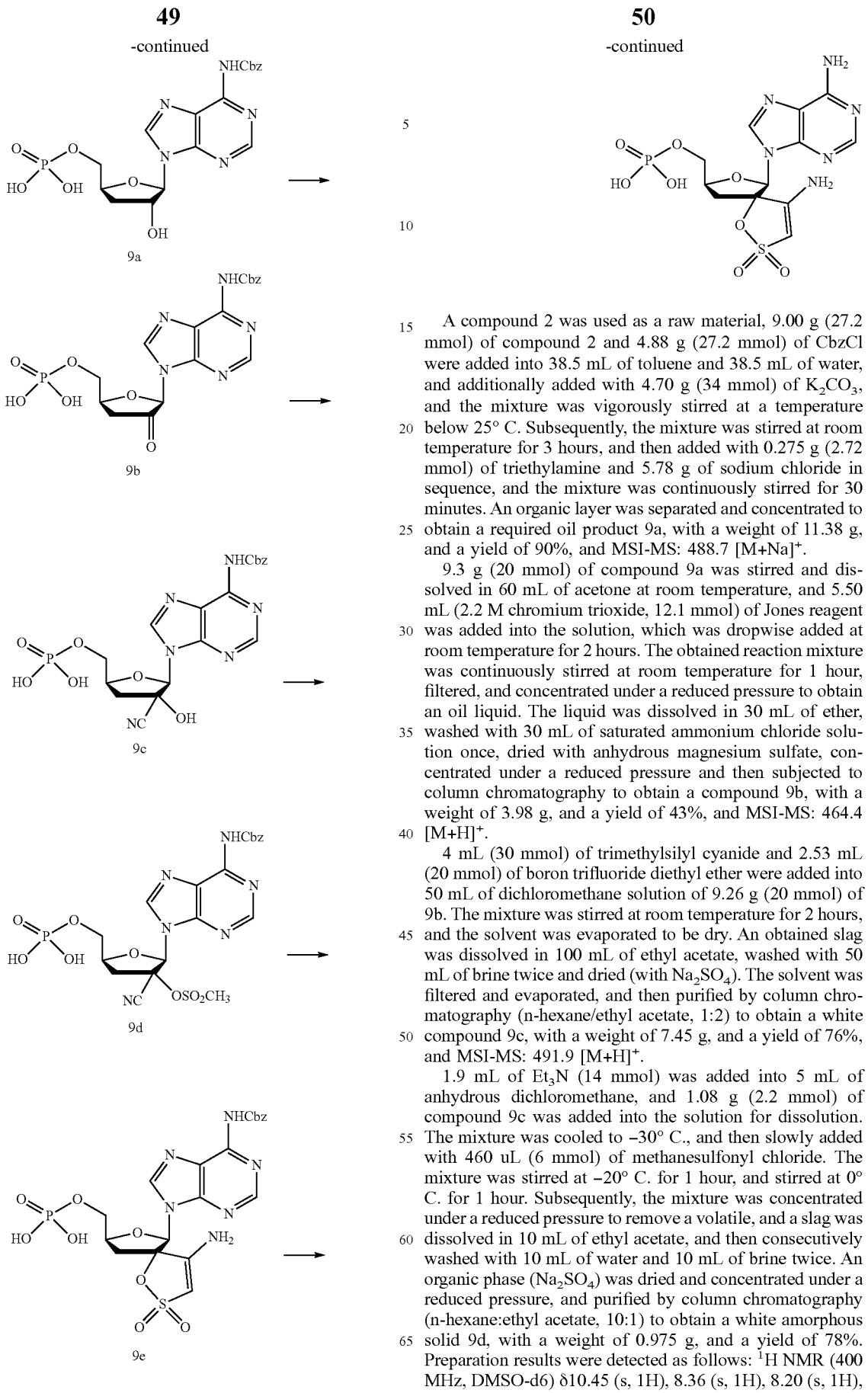

A compound 2 was used as a raw material, 9.00 g (27.2 mmol) of compound 2 and 4.88 g (27.2 mmol) of CbzCl were added into 38.5 mL of toluene and 38.5 mL of water, and additionally added with 4.70 g (34 mmol) of $K_2CO_3$, and the mixture was vigorously stirred at a temperature below 25° C. Subsequently, the mixture was stirred at room temperature for 3 hours, and then added with 0.275 g (2.72 mmol) of triethylamine and 5.78 g of sodium chloride in sequence, and the mixture was continuously stirred for 30 minutes. An organic layer was separated and concentrated to obtain a required oil product 9a, with a weight of 11.38 g, and a yield of 90%, and MSI-MS: 488.7 [M+Na]$^+$.

9.3 g (20 mmol) of compound 9a was stirred and dissolved in 60 mL of acetone at room temperature, and 5.50 mL (2.2 M chromium trioxide, 12.1 mmol) of Jones reagent was added into the solution, which was dropwise added at room temperature for 2 hours. The obtained reaction mixture was continuously stirred at room temperature for 1 hour, filtered, and concentrated under a reduced pressure to obtain an oil liquid. The liquid was dissolved in 30 mL of ether, washed with 30 mL of saturated ammonium chloride solution once, dried with anhydrous magnesium sulfate, concentrated under a reduced pressure and then subjected to column chromatography to obtain a compound 9b, with a weight of 3.98 g, and a yield of 43%, and MSI-MS: 464.4 [M+H]$^+$.

4 mL (30 mmol) of trimethylsilyl cyanide and 2.53 mL (20 mmol) of boron trifluoride diethyl ether were added into 50 mL of dichloromethane solution of 9.26 g (20 mmol) of 9b. The mixture was stirred at room temperature for 2 hours, and the solvent was evaporated to be dry. An obtained slag was dissolved in 100 mL of ethyl acetate, washed with 50 mL of brine twice and dried (with $Na_2SO_4$). The solvent was filtered and evaporated, and then purified by column chromatography (n-hexane/ethyl acetate, 1:2) to obtain a white compound 9c, with a weight of 7.45 g, and a yield of 76%, and MSI-MS: 491.9 [M+H]$^+$.

1.9 mL of $Et_3N$ (14 mmol) was added into 5 mL of anhydrous dichloromethane, and 1.08 g (2.2 mmol) of compound 9c was added into the solution for dissolution. The mixture was cooled to −30° C., and then slowly added with 460 uL (6 mmol) of methanesulfonyl chloride. The mixture was stirred at −20° C. for 1 hour, and stirred at 0° C. for 1 hour. Subsequently, the mixture was concentrated under a reduced pressure to remove a volatile, and a slag was dissolved in 10 mL of ethyl acetate, and then consecutively washed with 10 mL of water and 10 mL of brine twice. An organic phase ($Na_2SO_4$) was dried and concentrated under a reduced pressure, and purified by column chromatography (n-hexane:ethyl acetate, 10:1) to obtain a white amorphous solid 9d, with a weight of 0.975 g, and a yield of 78%. Preparation results were detected as follows: $^1$H NMR (400 MHz, DMSO-d6) δ10.45 (s, 1H), 8.36 (s, 1H), 8.20 (s, 1H), 7.34-7.32 (s, 5H), 6.12 (s, 1H), 4.65 (s, 2H), 4.30-4.03 (m, 4H), 3.74 (m, 1H), 3.15 (s, 3H), 2.41-2.16 (m, 2H). $^{13}$C NMR (100 MHz, DMSO-d6) δ153.6, 152.5, 151.7, 149.8, 140.2, 136.4, 128.9, 127.7, 127.2, 123.5, 120.4, 97.4, 71.6, 69.2, 68.2, 66.9, 38.2, 37.8. MSI-MS: 569.4 [M+H]$^+$.

490 mg (1.5 mmol) of cesium carbonate was added into 3 mL of anhydrous acetonitrile suspension of 0.568 g (1 mmol) of 9d, and the mixture was stirred at room temperature for 2 hours. The solvent was removed, and an obtained residue was dissolved in 20 mL of ethyl acetate, and washed with 10 mL of water and 10 mL of brine twice in sequence. An organic phase (Na$_2$SO$_4$) was dried and filtered, then concentrated under a reduced pressure, and purified by column chromatography (n-hexane/ethyl acetate, 3:1) to obtain a white solid 9e, with a weight of 4.49 g, and a yield of 79%, and MSI-MS: 569.4 [M+H]$^+$.

5.68 g of compound 9e (10 mmol) was dissolved in 200 mL of methanol. Subsequently, 1.5 g of ammonium formate (30 mmol) and 0.75 g of 10% Pd—C were added, and the reaction mixture was stirred at room temperature for 10 minutes, and then heated and refluxed for 45 minutes. The mixture was filtered through diatomaceous earth, and the filtrate was evaporated to be dry to obtain 4.12 g of compound 9, with a yield of 95%. Detection results of the prepared compound 9 were as follows: $^1$H NMR (400 MHz, DMSO-d6) δ8.59 (s, 1H), 8.38 (s, 1H), 7.14 (s, 2H), 6.88 (s, 2H), 6.16 (d, 1H), 5.25 (s, 1H), 4.28 (m, 1H), 4.18 (s, 2H), 4.02 (m, 1H), 3.74 (m, 1H), 2.09-1.96 (m, 2H). $^{13}$C NMR (100 MHz, DMSO-d6) δ168.5, 155.1, 151.4, 147.8, 141.1, 119.4, 98.2, 88.9, 86.1, 73.0, 68.1, 37.9. MSI-MS: 435.3 [M+H]$^+$.

Embodiment 10: Preparation of Compound: N-(3-hydroxy-5-(hydroxymethyl)tetrahydrofuran-2-yl)-9H-purine-6-yl)octadecylamine

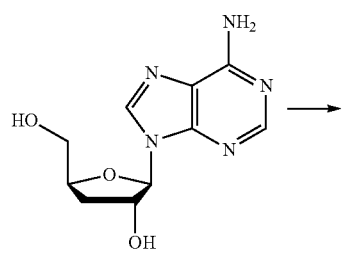

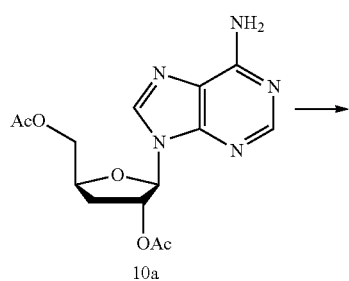

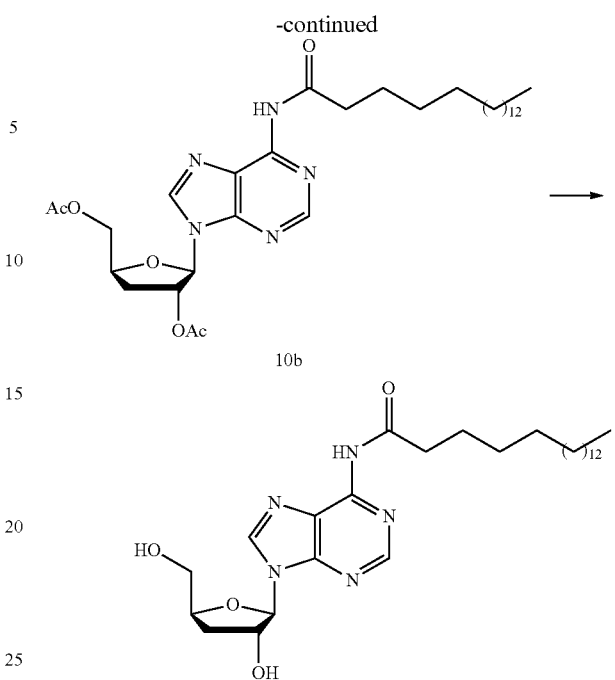

2.51 g (10 mmol) of cordycepin was added with 40.00 mL of anhydrous pyridine and 8.5 mL of acetic anhydride in ice bath. The reaction was monitored by HPLC, and the reaction was ended after reacting for about 5 hours. The solvent was removed to obtain a viscous liquid 10a, with a weight of 2.68 g, and a yield of 80%, and MSI-MS: 358.6 [M+Na]$^+$.

3.35 g (10 mmol) of compound 10a and 2.89 g (10 mmol) of octadecyl chloride were added with 60 mL of anhydrous pyridine in ice bath, the reaction was gradually subjected to temperature rise to 40° C. for reaction for 10 hours, the reaction was monitored by TLC, water and ethyl acetate were added for extraction after the reaction, an organic phase was reverse-extracted, the organic phase was collected for rotary evaporation to obtain an oil liquid 10b, and the oil liquid 10b was purified by column chromatography to obtain 5.40 g of purified product of 10b, with a yield of 90%, and MSI-MS: 624.4 [M+Na]$^+$.

6.01 g (10 mmol) of compound 10b was dissolved in 450 mL of ammonia methanol solution for reaction, and stirred at room temperature, the reaction was detected by thin layer chromatography, and the reaction was stopped 4 hours later. The solvent was removed to obtain a target product 10, and 4.67 g of the compound was weighed, with a yield of 90%.

Alternatively, protection and deprotection were carried out according to the preparation method of 1a in Embodiment 1, wherein the protected 1a was subjected to an acylation reaction in the second step herein, and then subjected to deprotection to prepare a compound 10. Detection results of the prepared compound 10 were as follows: $^1$H NMR (400 MHz, DMSO-d6) δ10.55 (s, 1H), 8.64 (s, 1H), 8.38 (s, 1H), 6.18 (d, 1H), 5.35 (d, 1H), 5.04 (m, 1H), 4.02 (m, 1H), 3.76 (m, 1H), 3.58 (m, 1H), 3.52 (m, 1H), 2.35 (m, 2H), 2.07-1.94 (m, 2H), 1.58 (m, 2H), 1.30-1.26 (m, 28H), 0.89 (m, 3H). $^{13}$C NMR (100 MHz, DMSO-d6) δ173.5, 153.3, 152.5, 148.8, 141.0, 122.6, 99.2, 84.1, 74.3, 63.8, 38.5, 34.8, 31.5, 29.5, 28.8, 25.6, 22.4, 14.7. (Some alkyl peaks were overlapped) MSI-MS: 540.7 [M+Na]$^+$.

Embodiment 11: N-(3-hydroxy-5-(hydroxymethyl)tetrahydrofuran-2-yl)-9H-purine-6-yl)cyclopentane carboxamide According to the method of Embodiment 10, cordycepin was subjected to steps of protection, acylation and deprotection to prepare a compound 11, wherein the octadecanoyl chloride was replaced by cyclopentyl formyl chloride, with an overall yield of 72%. Detection results of the prepared compound 11 were as follows: $^1$H NMR (400 MHz, DMSO-d6) δ10.52 (s, 1H), 8.66 (s, 1H), 8.38 (s, 1H), 6.16 (d, 1H), 5.28 (d, 1H), 5.01 (m, 1H), 4.01 (m, 1H), 3.77 (m, 1H), 3.57-3.46 (m, 2H), 2.46 (m, 1H), 2.08-1.88 (m, 2H), 1.80-1.55 (m, 8H). $^{13}$C NMR (100 MHz, DMSO-d6) δ172.5, 153.3, 151.5, 149.5, 139.8, 123.6, 98.4, 82.1, 74.9, 63.8, 49.5, 34.5, 32.4, 24.5. MSI-MS: 348.2 [M+H]$^+$.

Embodiment 12: N-(3-hydroxy-5-(hydroxymethyl)tetrahydrofuran-2-yl)-9H-purine-6-yl)isonicotinamide According to the method of Embodiment 10, cordycepin was subjected to steps of protection, acylation and deprotection to prepare a compound 12, wherein the octadecanoyl chloride was replaced by pyridine-3-formyl chloride, with an overall yield of 76%. Detection results of the prepared compound 12 were as follows: $^1$H NMR (400 MHz, DMSO-d6) δ11.05 (s, 1H), 8.86 (d, 2H), 8.41 (s, 1H), 8.22 (s, 1H), 8.01 (d, 2H), 6.15 (d, 1H), 5.22 (d, 1H), 4.98 (m, 1H), 4.02 (m, 1H), 3.75 (m, 1H), 3.58-3.46 (m, 2H), 2.08-1.88 (m, 2H). $^{13}$C NMR (100 MHz, DMSO-d6) δ165.5, 152.3, 151.9, 149.8, 149.7, 140.9, 140.4, 123.4, 120.5, 99.4, 82.8, 74.7, 63.8, 35.4. MSI-MS: 357.3 [M+H]$^+$.

Embodiment 13: (5-(6-amino-2-fluoro-9H-purine-9-yl)-4-hydroxytetrahydrofuran-2-yl)dihydromethyl phosphate

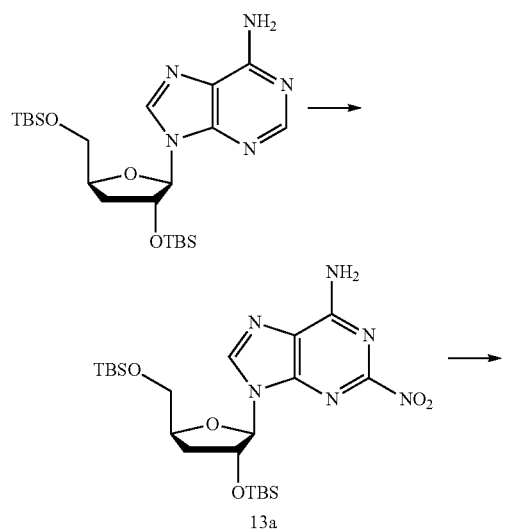

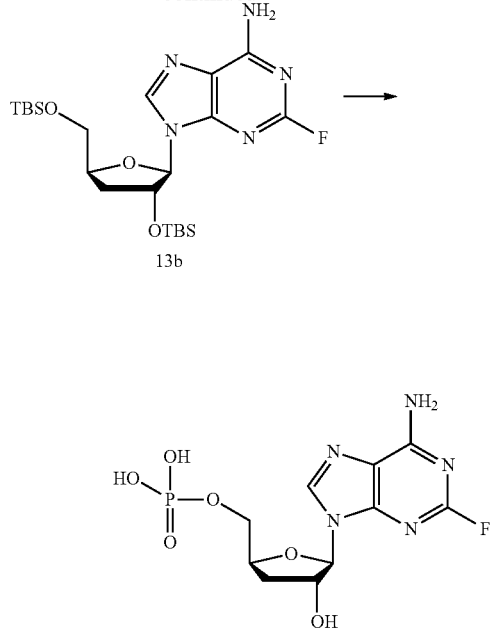

193 μL (1.39 mmol) of 2,2,2-trifluoroacetic anhydride was added into a solution of dry dichloromethane (15 mL) containing 428 mg (1.40 mmol) of tetrabutylammonium nitrate at 0° C. to prepare a nitration mixture. After reacting at 0° C. for 45 minutes, the solution was slowly added into dry dichloromethane (15 mL) of 480 mg (1 mmol) of compound 1a. After reacting at room temperature in the dark for 14 hours, the reaction mixture was poured into a cold mixture of H$_2$O (50 mL), saturated NaHCO$_3$ (35 mL) and CH$_2$Cl$_2$:Et$_2$O (1:2, 30 mL) for extraction, and extracted with CH$_2$Cl$_2$:Et$_2$O (1:2, 30 mL) twice. An organic extract was washed with brine, dried with anhydrous Na$_2$SO$_4$, and dried in vacuum (the temperature was kept below 40° C.). A crude product was purified by column chromatography, and eluted with CH$_2$Cl$_2$, and then a compound 13a was obtained by using CH$_2$Cl$_2$:acetone (99:1 to 95:5), with a weight of 273 mg, and a yield of 52%, and MSI-MS: 525.4 [M+H]$^+$.

TBAF (equivalent amount of 1.3, 600 μL, 0.6 mmol) was dropwise added into a suspension of dry acetonitrile (15 mL) containing 236 mg (0.45 mmol) of 13a within 1 minute at 0° C. The mixture was stirred for 20 minutes, and an obtained solution was evaporated in vacuum without heating. A crude product was purified by column chromatography (CH$_2$Cl$_2$:acetone, 100:0 to 90:10) to obtain a compound 13b, with a weight of 78 mg, and a yield of 35%, and MSI-MS: 498.8 [M+H]$^+$.

The prepared compound 13b was treated by the phosphorylation method in Embodiment 2 and the deprotection method in Embodiment 1 to obtain a compound 13, with a yield of 65%. Detection results of the prepared compound 13 were as follows: $^1$H NMR (400 MHz, DMSO-d6) δ8.38 (s, 1H), 6.98 (s, 2H), 6.16 (d, 1H), 5.36 (d, 1H), 4.28 (m, 1H), 4.21 (s, 2H), 4.02 (m, 1H), 3.95 (m, 1H), 3.74 (m, 1H), 2.02-1.82 (m, 2H). $^{13}$C NMR (100 MHz, DMSO-d6) δ158.3, 157.2, 148.8, 141.5, 118.6, 97.2, 74.9, 74.6, 67.1, 35.5. MSI-MS: 372.2 [M+Na]$^+$.

Embodiment 14: (5-(6-amino-2-mercapto-9H-purine-9-yl)-4-hydroxytetrahydrofuran-2-yl)dihydromethyl phosphate

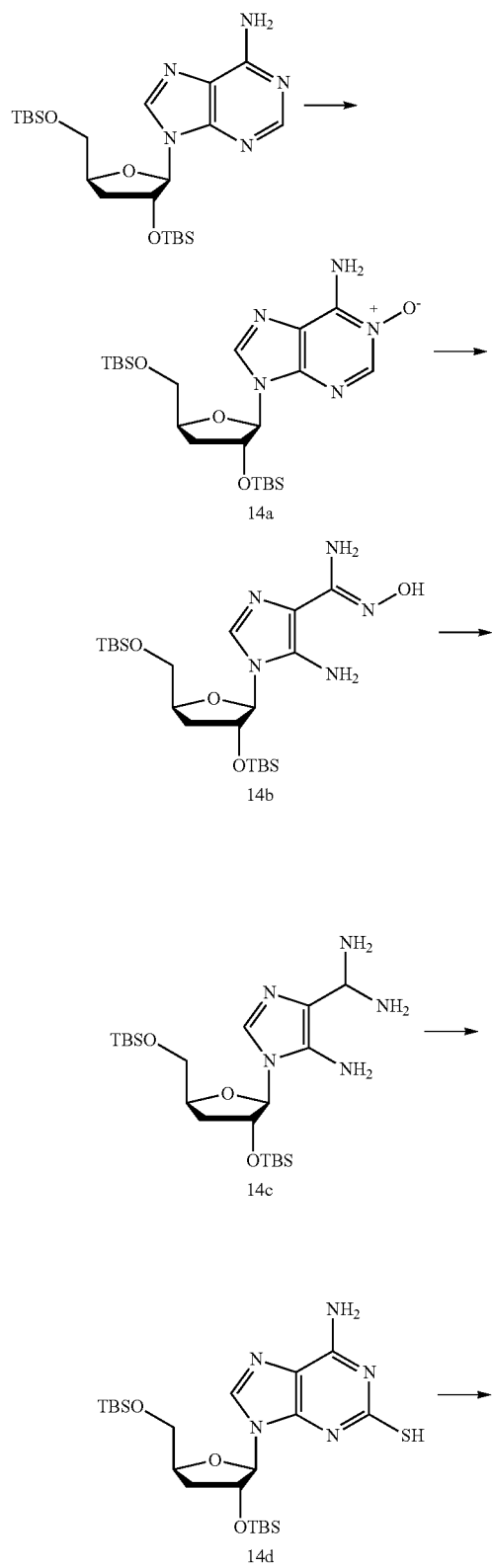

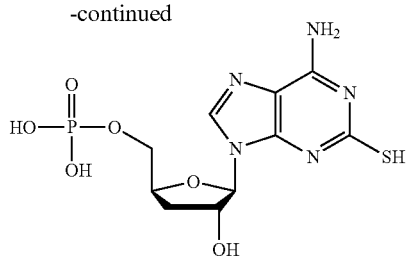

4.80 g (10 mmol) of compound 1a was added into 60 mL of acetic acid, and stirred at 40° C. and dissolved. After the solution was cooled to room temperature, 5 mL (25 mmol) of 30% hydrogen peroxide was added. The solution was stirred at 40° C. for 3 days, and filtered, and a solid was recrystallized in water to obtain a compound 14a, with a weight of 3.37 g, and a yield of 68%, and MSI-MS: 497.4 [M+H]$^+$.

4.96 g (10 mmol) of 14a was added into 40 mL of 3 M hydrochloric acid aqueous solution, heated and refluxed until the solid was completely dissolved, continuously refluxed for 10 minutes, and then cooled to room temperature, and 20 mL of ethanol was added after removing the solvent. A precipitated crystal was filtered and dried to obtain a compound 14b, with a weight of 2.92 g, and a yield of 62%, and MSI-MS: 487.5 [M+H]$^+$.

4.86 g (10 mmol) of compound 14b was dissolved in 100 mL of water, added with 1.0 g of activated Raneyni in batches, and introduced with hydrogen. The reaction mixture was stirred at 55° C. for reaction for 4 days. The introduction of hydrogen was stopped, inorganic salt was removed by filtration, and then the solvent was removed by distillation under a reduced pressure. A crude product was washed with ethanol and ether respectively, and dried to obtain a gray solid 14c, with a weight of 3.30 g, and a yield of 70%, and MSI-MS: 495.8 [M+Na]$^+$.

Methanol, pyridine and carbon disulfide were mixed according to a volume ratio of 4:5:2 to obtain 50 mL of solution, and added with 4.72 g (10 mmol) of 14c, and a balloon was sleeved on a reflux condensing tube to prevent carbon disulfide from volatilizing. The reaction mixture was stirred at 40° C. for reaction for 4 days, and filtered. A crude product was heated and refluxed in 5% sulfuric acid aqueous solution for 20 minutes, filtered while the mixture was hot to remove impurities, cooled to room temperature, and then filtered and dried to obtain a gray crystal 14d, with a weight of 2.82 g, and a yield of 55%. The prepared compound 14d was treated by the phosphorylation method in Embodiment 2 and the deprotection method in Embodiment 1 to obtain a compound 14, with a yield of 71%. Detection results of the prepared compound 14 were as follows: $^1$H NMR (400 MHz, DMSO-d6) δ12.22 (s, 1H), 8.36 (s, 1H), 6.99 (s, 2H), 6.16 (d, 1H), 5.33 (d, 1H), 4.30 (m, 1H), 4.21 (s, 2H), 4.02 (m, 1H), 3.94 (m, 1H), 3.71 (m, 1H), 2.06-1.88 (m, 2H). $^{13}$C NMR (100 MHz, DMSO-d6) δ154.3, 152.1, 149.2, 139.8, 118.6, 99.2, 74.8, 74.3, 67.1, 35.1. MSI-MS: 364.3 [M+H]$^+$.

Embodiment 15: (5-(6-amino-9H-purine-9-yl)-3-fluoro-4-hydroxytetrahydrofuran-2-yl)dihydromethyl phosphate

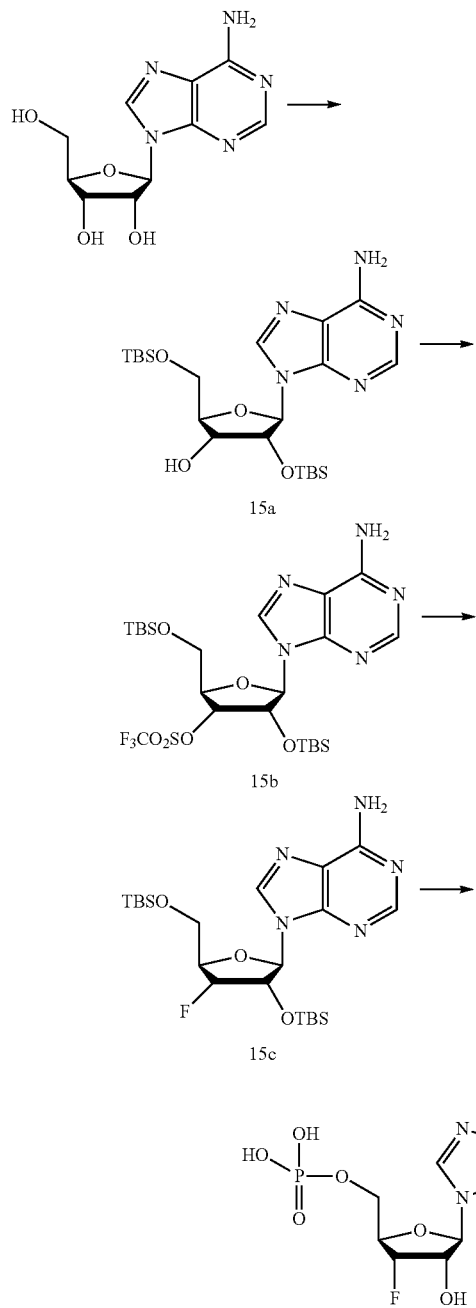

15a

15b

15c 2.67 g (10 mmol) of adenosine, 3.618 g (24 mmol) of TBSCL and 3.95 g (50 mmol) of pyridine were added into 10 mL of DMF, stirred at room temperature for 10 hours, and extracted with water and ethyl acetate after the reaction, and an organic phase was concentrated and subjected to column chromatography to obtain 2.33 g of 15a, with a yield of 47%, and MSI-MS: 497.7 [M+H]+.

The solution of dichloromethane (100 mL) containing 4.96 g (10 mmol) of 15a and pyridine (1.5 mL) was stirred and cooled to −5° C. under protection of nitrogen, dropwise added with 2.5 mL (15 mmol) of trifluoromethanesulfonic anhydride for continuous reaction at 0° C. for 2 hours, poured into ice water (100 mL) after complete reaction was shown in TLC, and stirred and layered, and a water phase was extracted with dichloroalkane (100 mL). Dichloromethane phases were combined, washed with saturated sodium chloride solution, dried with anhydrous sodium sulfate, and then filtered, the filtrate was concentrated under a reduced pressure, and petroleum ether (40 mL) was added into the residue for recrystallization, filtered and then dried to obtain 15b, with a weight of 5.65 g, and a yield of 90%. Preparation results were detected as follows: $^1$H NMR (400 MHz, DMSO-d6) δ8.59 (s, 1H), 8.35 (s, 1H), 7.11 (s, 2H), 6.15 (d, 1H), 5.05 (m, 1H), 4.55 (m, 1H), 4.12 (m, 1H), 4.02-3.79 (m, 2H), 0.99 (s, 18H), 0.20 (s, 12H). $^{13}$C NMR (100 MHz, DMSO-d6) δ156.2, 152.5, 149.7, 140.2, 119.5, 118.4, 96.5, 86.4, 83.5, 73.8, 63.2, 30.8, 30.6, 25.8, 0. MSI-MS: 628.8 [M+H]+.

6.28 g (10 mmol) of 15b was dissolved in ethyl acetate (40 mL) under protection of nitrogen, added with 10 mL (22 mmol) of triethylamine solution of 37% hydrofluoric acid, stirred and subjected to temperature rise to 70° C. for reaction for about 8 hours. The mixture was cooled to room temperature after complete reaction was shown in TLC, washed with saturated sodium bicarbonate solution to be neutral, then washed with saturated sodium chloride solution, dried with anhydrous sodium sulfate, and filtered, the filtrate was concentrated under a reduced pressure, and the residue was recrystallized with anhydrous methanol (30 mL) to obtain a solid 15c, with a weight of 2.04 g, and a yield of 41%. The prepared compound 15c was treated by the phosphorylation method in Embodiment 2 and the deprotection method in Embodiment 1 to obtain a compound 15, with a yield of 77%. Detection results of the prepared compound 15 were as follows: $^1$H NMR (400 MHz, DMSO-d6) δ8.58 (s, 1H), 8.37 (s, 1H), 7.07 (s, 2H), 6.15 (d, 1H), 5.33 (d, 1H), 4.70 (m, 1H), 4.44 (m, 1H), 4.28 (m, 1H), 4.18 (s, 2H), 4.02 (m, 1H) 3.55 (m, 1H). $^{13}$C NMR (100 MHz, DMSO-d6) δ155.3, 151.4, 148.9, 141.1, 119.6, 97.2, 90.1, 79.0, 73.4, 61.5. MSI-MS: 350.2 [M+H]+.

Embodiment 16: isopropyl ((((((5-(6-amino-9H-purin-9-yl)-4-cyano tetrahydrofuran-2-yl)methoxy)methyl)(phenoxy)phosphoryl)alanine ester

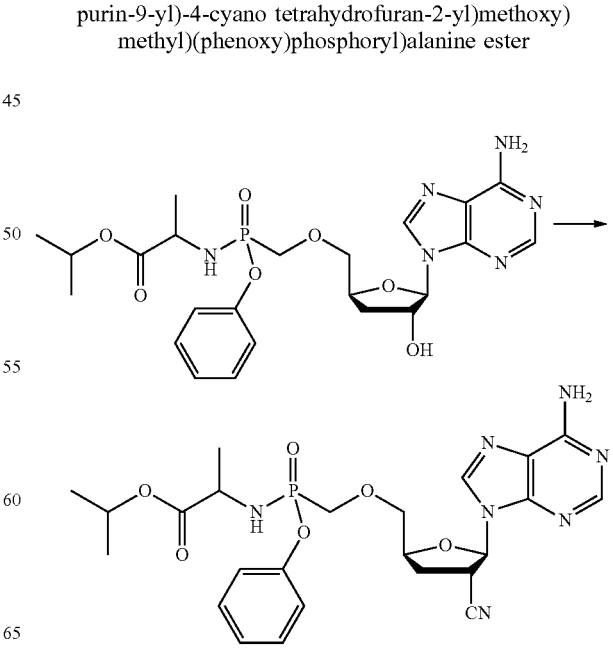

A compound 7 was prepared according to the method in Embodiment 7, and the compound 7 was used as a raw material to prepare a compound 16. 5.34 g (10 mmol) of compound 7 was dissolved in 100 mL of dichloromethane solution, and then added with 1.3 mL (1.50 g, 10 mmol) of trifluoromethylsulfonic acid. After reacting and being stirred for 10 minutes, 2.7 mL of trimethylsilyl triflate (10 mmol) was slowly dropwise added into the solution, and the obtained mixture was stirred at −40° C. for 30 minutes. Subsequently, 3.96 g (40 mmol) of trimethylnitrile silane was slowly added, and the mixture was stirred for 2 hours. Subsequently, 3.5 mL of triethylamine was dropwise added, and the reaction mixture was heated to room temperature. Subsequently, 5.5 g of solid sodium bicarbonate and 20.7 mL of water were added, and the obtained mixture was stirred for 10 minutes. Subsequently, the mixture was extracted with dichloromethane and water to obtain an organic extract, and the organic extract was washed with brine, then dried with anhydrous sodium sulfate, and concentrated under a reduce pressure. A crude slag was purified by column chromatography to obtain a product compound 16 of a gray solid, with a weight of 1.71 g, and a yield of 32%. Detection results of the prepared compound 16 were as follows: $^1$H NMR (400 MHz, DMSO-d6) δ8.57 (s, 1H), 8.36 (s, 1H), 7.41 (m, 2H), 7.22 (m, 3H), 7.09 (s, 2H), 6.17 (d, 1H), 4.99 (d, 1H), 3.97 (m, 1H), 3.74-3.33 (m, 6H), 2.88 (m, 1H), 2.04-1.92 (m, 2H), 1.28-1.14 (d, 9H). $^{13}$C NMR (100 MHz, DMSO-d6) δ173.4, 155.3, 152.5, 150.2, 149.8, 141.3, 130.2, 121.6, 120.5, 118.2, 92.2, 77.4, 75.0, 73.1, 69.1, 51.2, 26.5, 25.8, 22.4, 20.1. MSI-MS: 544.5 [M+H]$^+$.

Embodiment 17: (((((((5-(6-amino-2-fluoro-9H-purine-9-yl)-4-hydroxytetrahydrofuran-2-yl)methoxy)methyl)phosphoryl)bis(oxy)bis(methylene)bis(2,2-dimethylpropionic acid)

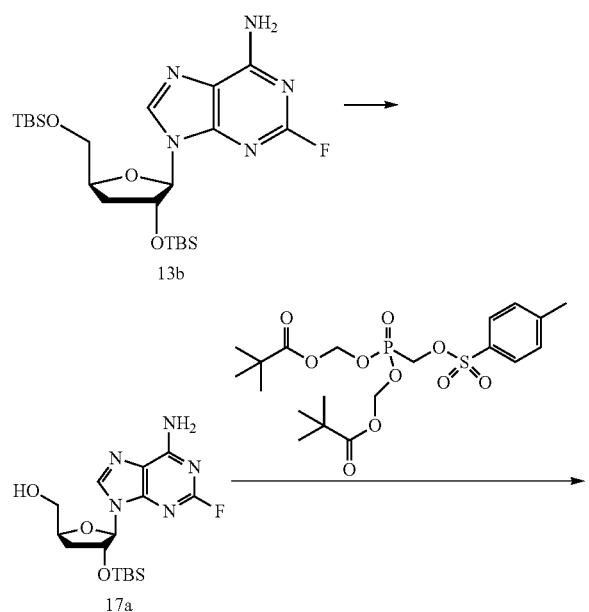

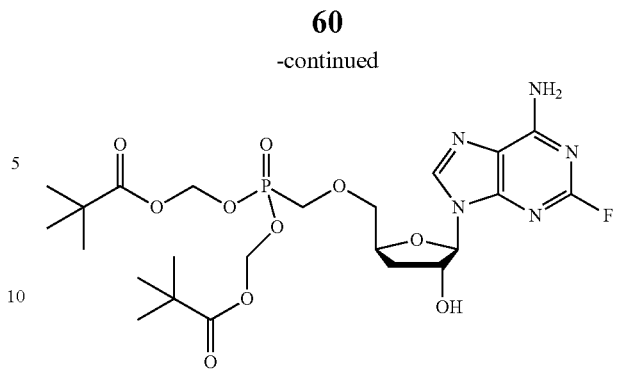

A compound 13b was prepared according to the method in Embodiment 13, the 13b was used as a raw material to prepare a compound 17a according to the protection method of 1b in Embodiment 1, and the compound 17a was used as a raw material to prepare a compound 17 according to the preparation method of 3a in Embodiment 3, wherein diethyl p-toluenesulfonyl methyl phosphonate was replaced by (((tolyloxy)methyl)phosphoryl)bis(oxy))bis(methylene)bis(2,2-dimethylpropionic acid) in equivalent amount, and the 1b was replaced by the 17a in equivalent amount, with a total yield of 61%. Detection results of the prepared compound 17 were as follows: $^1$H NMR (400 MHz, DMSO-d6) δ8.33 (s, 1H), 6.99 (s, 2H), 6.88 (s, 4H), 6.16 (d, 1H), 5.37 (d, 1H), 4.02 (m, 1H), 3.95 (m, 1H), 3.85 (s, 2H), 3.61-3.42 (m, 2H), 2.05-1.88 (m, 2H), 1.25 (s, 18H). $^{13}$C NMR (100 MHz, DMSO-d6) δ175.2, 158.3, 157.5, 148.6, 140.3, 119.2, 99.2, 92.2, 79.1, 74.8, 74.3, 71.2, 38.5, 35.8 26.8. MSI-MS: 592.5 [M+H]$^+$.

Embodiment 18: (((((5-(6-amino-9H-purine-9-yl)-3-fluoro-4-hydroxytetrahydrofuran-2-yl)methoxy)methyl)phosphoryl)bis(oxy))bis(methylene)bis(2,2-dimethylpropionic acid)

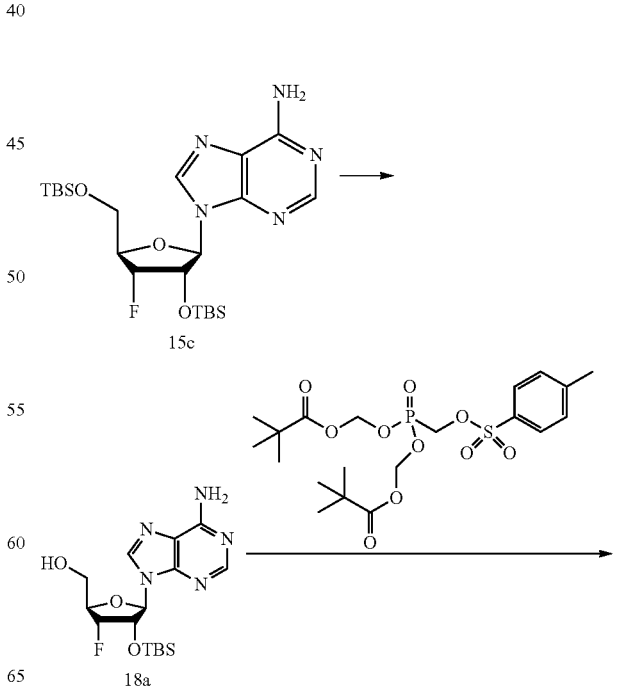

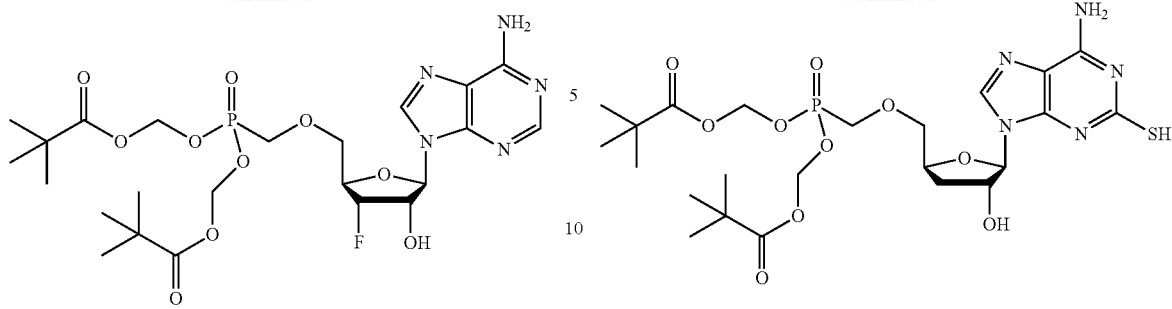

A compound 18b was prepared according to the method in Embodiment 15 and the protection method of 1b in Embodiment 1, and the compound 18a was used as a raw material to prepare a compound 18 according to the preparation method of 3a in Embodiment 3, wherein diethyl p-toluenesulfonyl methyl phosphonate was replaced by (((tolyloxy)methyl)phosphoryl)bis(oxy))bis(methylene)bis (2,2-dimethylpropionic acid) in equivalent amount, and the 1b was replaced by the 18a in equivalent amount, with a total yield of 34%. Detection results of the prepared compound 18 were as follows: $^1$H NMR (400 MHz, DMSO-d6) δ8.59 (s, 1H), 8.32 (s, 1H), 7.09 (s, 2H), 6.84 (s, 4H), 6.15 (d, 1H), 5.35 (d, 1H), 4.71-4.64 (m, 2H), 3.85 (m, 2H), 3.60-3.33 (m, 3H), 1.27 (s, 18H). $^{13}$C NMR (100 MHz, DMSO-d6) δ175.9, 157.3, 151.5, 149.8, 141.3, 118.9, 98.2, 92.8, 91.5, 79.4, 73.3, 71.4, 70.5, 38.6, 27.8. MSI-MS: 592.4 [M+H]$^+$.

A compound 14d was prepared according to the method in Embodiment 14, the 14d was used as a raw material to prepare a compound 19a according to the protection method of 1b in Embodiment 1, and the compound 19a was used as a raw material to prepare a compound 19 according to the preparation method of 3a in Embodiment 3, wherein diethyl p-toluenesulfonyl methyl phosphonate was replaced by (((tolyloxy)methyl)phosphoryl)bis(oxy))bis(methylene)bis (2,2-dimethylpropionic acid) in equivalent amount, and the 1b was replaced by the 19a in equivalent amount, with a total yield of 18%. Detection results of the prepared compound 19 were as follows: $^1$H NMR (400 MHz, DMSO-d6) δ12.12 (s, 1H), 8.34 (s, 1H), 7.01 (s, 2H), 6.84 (s, 4H), 6.12 (d, 1H), 5.35 (d, 1H), 4.01 (m, 1H), 3.93 (m, 1H), 3.85 (s, 2H), 3.63-3.37 (m, 2H), 2.06-1.85 (m, 2H), 1.27 (s, 18H). $^{13}$C NMR (100 MHz, DMSO-d6) δ175.8, 155.4, 152.5, 149.7, 140.5, 118.9, 98.7, 92.8, 78.1, 74.9, 74.7, 71.2, 38.7, 34.5, 27.5. MSI-MS: 606.6 [M+H]$^+$.

Embodiment 19: (((((5-(6-amino-2-mercapto-9H-purin-9-yl)-4-hydroxytetrahydrofuran-2-yl)methoxy) methyl)phosphoryl)bis(oxy)bis(methylene)bis(2,2-dimethylpropionic acid)

Embodiment 20: isopropyl(((((5-(6-amino-2-fluoro-9H-purin-9-yl)-4-hydroxytetrahydrofuran-2-yl) methoxy)methyl)(phenoxy)phosphoryl)alanine ester

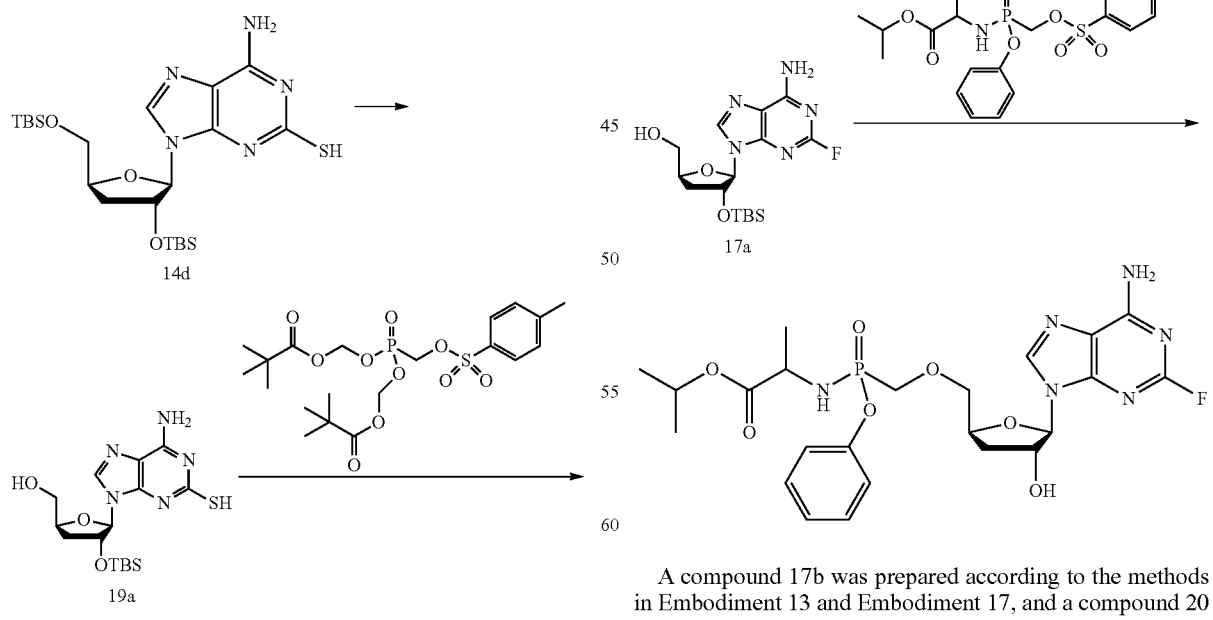

A compound 17b was prepared according to the methods in Embodiment 13 and Embodiment 17, and a compound 20 was prepared according to the method in Embodiment 7, wherein diethyl p-toluenesulfonyl methyl phosphonate was replaced by isopropyl(phenoxy((tolyloxy)methyl)phosphoryl)alanine ester in equivalent amount, and the 1b was replaced by the 17a, with a total yield of 67%. Detection results of the prepared compound 20 were as follows: ¹H NMR (400 MHz, DMSO-d6) δ8.37 (s, 1H), 7.40 (m, 2H), 7.20 (m, 3H), 7.02 (s, 2H), 6.15 (d, 1H), 5.38 (s, 1H), 4.94 (m, 1H), 4.00 (m, 1H), 3.95 (m, 1H), 3.71-3.53 (m, 5H), 3.34 (m, 1H), 2.06-1.82 (m, 2H), 1.28-1.14 (d, 9H). ¹³C NMR (100 MHz, DMSO-d6) δ172.1, 157.3, 156.8, 150.0, 149.8, 140.2, 121.3, 120.6, 119.2, 97.4, 76.6, 75.0, 74.8, 72.1, 69.4, 50.1, 34.5, 21.7, 19.5. MSI-MS: 553.5 [M+H]⁺.

Embodiment 21: N-(2-fluoro-3-hydroxy-5-(hydroxymethyl)tetrahydrofuran-2-yl)-9H-purine-6-yl) octadecylamine

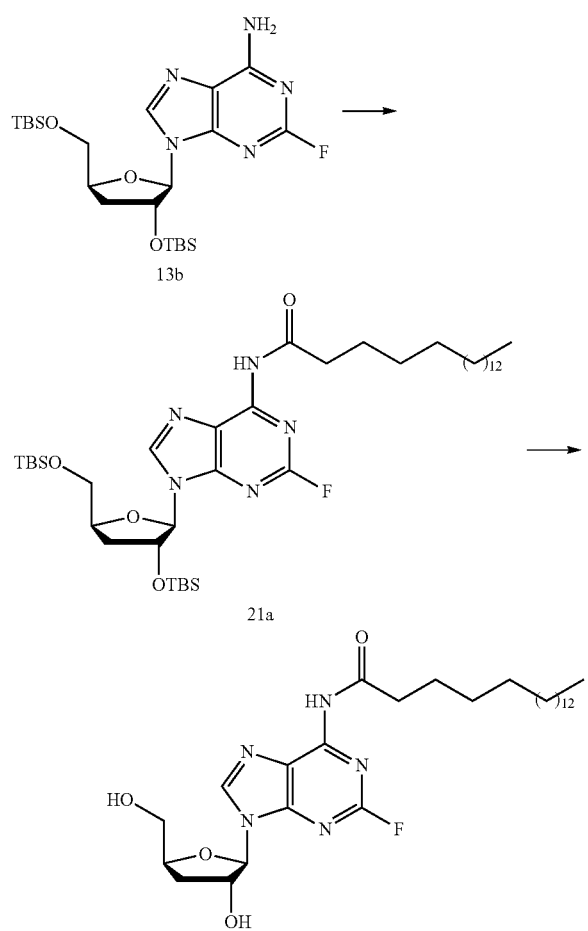

A compound 13b was prepared according to the method in Embodiment 13, the 13b was used as a raw material to prepare a compound 21a according to the preparation method of 10b from 10a in Embodiment 10, and the 21a was used as a raw material to prepare a compound 21 according to the deprotection method of 1a in Embodiment 1, with a total yield of 74%. Detection results of the prepared compound 21 were as follows: ¹H NMR (400 MHz, DMSO-d6) δ10.53 (s, 1H), 8.34 (s, 1H), 6.15 (d, 1H), 5.6 (d, 1H), 5.02 (m, 1H), 4.01 (m, 1H), 3.78 (m, 1H), 3.57 (m, 1H), 3.51 (m, 1H), 2.35 (m, 2H), 2.09-1.91 (m, 2H), 1.52 (m, 2H), 1.33-1.25 (m, 28H), 0.88 (m, 3H). ¹³C NMR (100 MHz, DMSO-d6) δ172.5, 153.5, 152.7, 148.6, 141.2, 122.4, 99.1, 84.5, 74.6, 63.4, 37.3, 34.2, 32.3, 29.4, 28.7, 25.7, 22.3, 14.5. (Some alkyl peaks were overlapped) MSI-MS: 536.6 [M+H]⁺.

Embodiment 22: N-(4-chloro-3-hydroxy-5-(hydroxymethyl)tetrahydrofuran-2-yl)-9H-purine-6-yl) octadecylamine

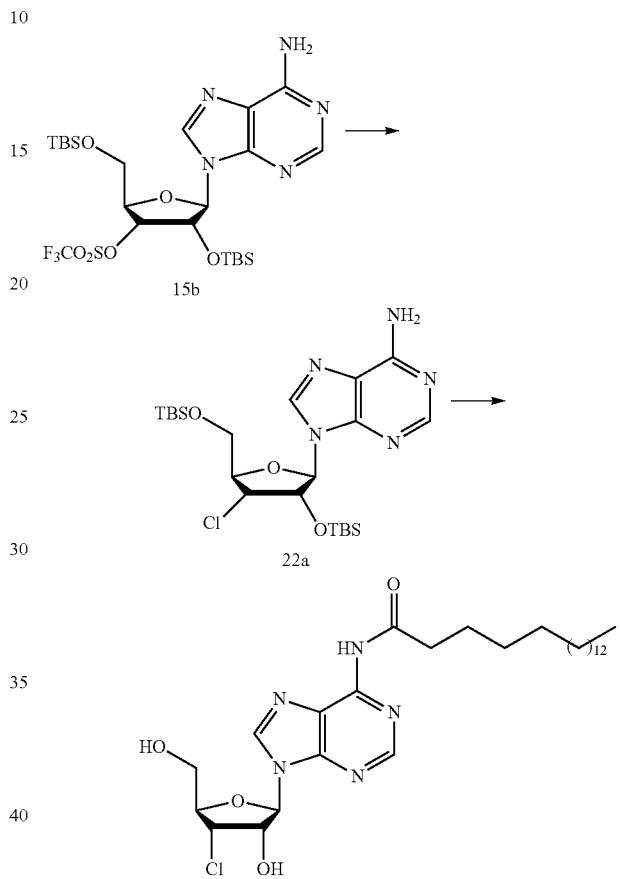

Adenosine was used as a raw material to prepare 15b according to the method in Embodiment 15, the 15b was used as a raw material, and 6.28 g (10 mmol) of 15b was dissolved in ethyl acetate (40 mL) under protection of nitrogen, added with 10 mL (22 mmol) of triethylamine solution of 37% hydrochloric acid, stirred and subjected to temperature rise to 70° C. for reaction for about 8 hours. The mixture was cooled to room temperature after complete reaction was shown in TLC, washed with saturated sodium bicarbonate solution to be neutral, then washed with saturated sodium chloride solution, dried with anhydrous sodium sulfate, and filtered, the filtrate was concentrated under a reduced pressure, and the residue was recrystallized with anhydrous methanol (30 mL) to obtain a solid 22a, with a weight of 1.95 g, and a yield of 38%, and MSI-MS: 515.2 [M+H]⁺.

The 22a was used as a raw material to prepare a compound 22 according to the preparation method of 10b from 10a in Embodiment 10 in combination with the deprotection method of 1a in Embodiment 1, with a total yield of 79%. Detection results of the prepared compound 22 were as follows: ¹H NMR (400 MHz, DMSO-d6) δ10.60 (s, 1H), 8.67 (s, 1H), 8.35 (s, 1H), 6.15 (d, 1H), 5.33 (d, 1H), 4.98

(m, 1H), 4.31 (m, 1H), 4.02 (m, 1H), 3.78 (m, 1H), 3.58 (m, 1H), 3.53 (m, 1H), 2.32 (m, 2H), 1.51 (m, 2H), 1.34-1.21 (m, 28H), 0.87 (m, 3H). $^{13}$C NMR (100 MHz, DMSO-d6) δ171.4, 152.5, 151.6, 148.4, 140.5, 121.4, 98.7, 77.5, 74.3, 68.1, 59.4, 38.2, 33.7, 31.5, 28.1, 27.5, 25.4, 22.1, 14.6. (Some alkyl peaks were overlapped) MSI-MS: 553.2 [M+H]$^+$.

Embodiment 23: (((((4-hydroxy-5-(6-(isoniazid)-9H-purin-9-yl)tetrahydrofuran-2-yl)methoxy)methyl)phosphoryl)bis (oxy))bis(methylene)bis(2,2-dimethylpropionic acid)

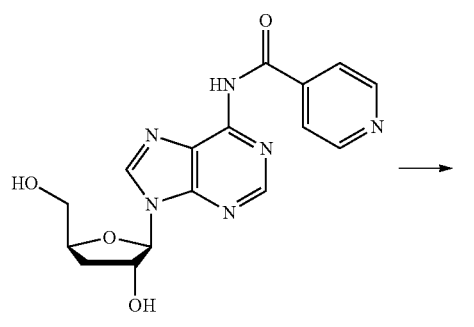

12

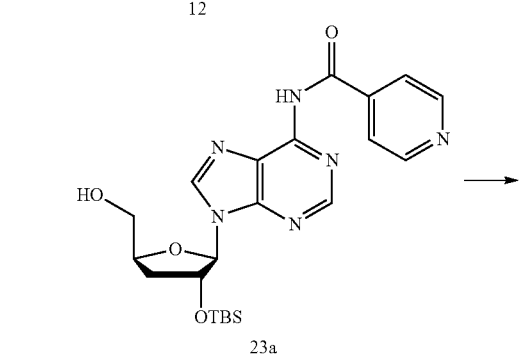

23a

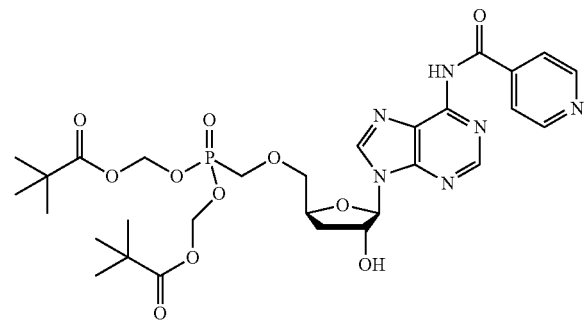

A compound 12 was used as a raw material to prepare a compound 23a according to the protection method of 1b in Embodiment 1, the compound 23a was used as a raw material to prepare a compound 23 according to the preparation process of 17 from 17a in Embodiment 17, the 17a was replaced by the 23a in equivalent amount in the reaction, and a total yield of the reaction was 81%. Detection results of the prepared compound 23 were as follows: $^1$H NMR (400 MHz, DMSO-d6) δ11.05, (s, 1H), 8.85 (d, 2H), 8.34 (s, 1H), 8.18 (s, 1H), 8.00 (d, 2H), 6.84 (s, 4H), 6.14 (d, 1H), 5.35 (d, 1H), 4.01 (m, 1H), 3.94 (m, 1H), 3.86 (s, 2H), 3.60-3.38 (m, 2H), 2.06-1.84 (m, 2H), 1.27 (s, 18H). $^{13}$C NMR (100 MHz, DMSO-d6) δ175.8, 165.1, 152.4, 151.5, 149.8, 149.6, 140.7, 140.2, 121.2, 120.1, 99.5, 92.8, 78.1, 74.7, 74.5, 71.4, 38.7, 34.5, 27.2. MSI-MS: 679.6 [M+H]$^+$.

Embodiment 24: isopropyl(((((4-hydroxy-5-(6-(isonicotinamide)-9H-purin-9-yl)tetrahydrofuran-2-yl)methoxy)methyl)(phenoxy)phosphoryl)alanine ester

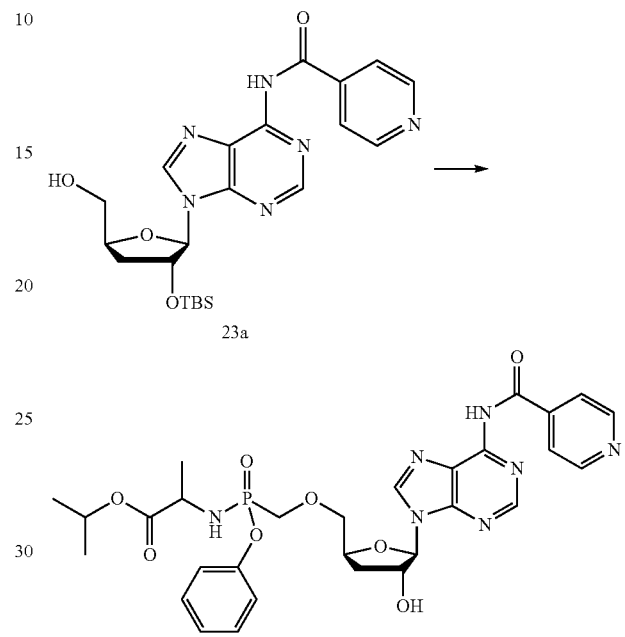

A compound 23a was prepared according to the method in Embodiment 23, and the 23a was used as a raw material to prepare a compound 24 according to the method in Embodiment 7, wherein the compound 1b was replaced by the 23a in equivalent amount, with a total yield of 85%. Detection results of the prepared compound 24 were as follows: $^1$H NMR (400 MHz, DMSO-d6) δ11.08 (s, 1H), 8.81 (d, 2H), 8.36 (s, 1H), 8.18 (s, 1H), 8.02 (d, 2H), 7.42 (m, 2H), 7.21 (m, 3H), 6.16 (d, 1H), 5.35 (s, 1H), 4.92 (m, 1H), 4.01-3.95 (m, 2H), 3.65-3.54 (m, 5H), 3.35 (m, 1H), 2.04-1.84 (m, 2H), 1.25-1.18 (d, 9H). $^{13}$C NMR (100 MHz, DMSO-d6) δ171.1, 165.2, 152.7, 151.8, 150.4, 149.8, 149.5, 140.5, 140.1, 130.4, 123.2, 121.8, 121.4, 120.2, 99.3, 76.7, 74.8, 74.5, 72.5, 69.8, 50.4, 34.7, 21.5, 19.3. MSI-MS: 640.6 [M+H]$^+$.

Embodiment 25: (5-(6-amino-9H-purine-9-yl)-3-azide-4-hydroxytetrahydrofuran-2-yl)dihydromethyl phosphate

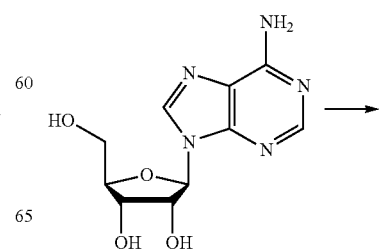

-continued

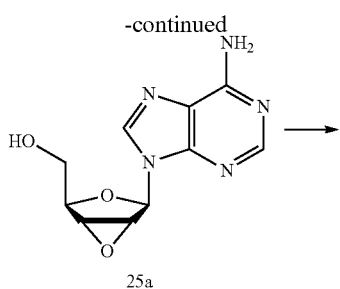

25a

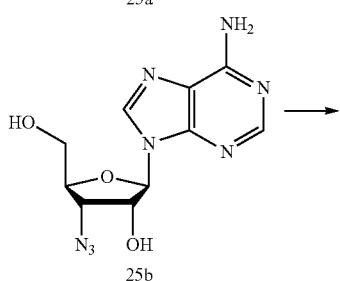

25b

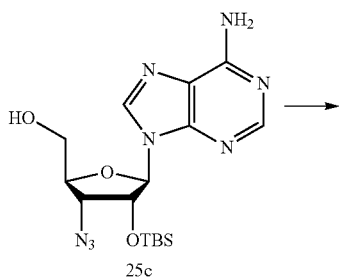

25c

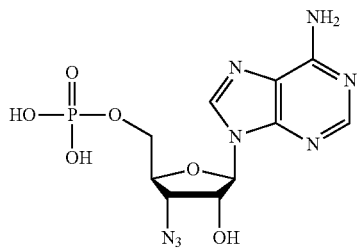

2.67 g (10.0 mmol) of adenosine and 5.78 g (22 mmol) of PPh₃ were added into a round-bottomed flask under an argon atmosphere, and then added with 18 mL of DMF, and the obtained mixture was stirred at room temperature until a solid was completely dissolved. The solution was cooled to 10° C., and quickly dropwise added with 4.4 ml (2.2 mmol) of diisopropyl azodiformate (DIAD), so that the reaction mixture reached room temperature. The mixture was stirred at 40° C. for 2 hours, then DMF was evaporated under a reduced pressure to obtain a viscous liquid, and the mixture was allocated between 150 mL of water and 100 mL of ether. A water layer was collected and washed with 100 mL of ether. An organic phase was concentrated under a reduced pressure, and a crude product was purified by column chromatography, and eluted with a mixture of DCM and an acetone solvent (3:1 to 2:3) to obtain a compound 25a of a white solid, with a weight of 1.84 g, and a yield of 74%, and detection results of the prepared compound were as follows: ¹H NMR (400 MHz, DMSO-d6) δ8.57 (s, 1H), 8.36 (s, 1H), 7.10 (s, 2H), 6.37 (d, 1H), 4.59 (m, 1H), 3.95 (s, 1H), 3.57-3.50 (m, 2H), 2.62-2.55 (m, 2H). ¹³C NMR (100 MHz, DMSO-d6) δ156.3, 152.5, 149.9, 140.5, 119.5, 90.4, 82.6, 63.5, 60.8, 59.6. MSI-MS: 250.2 [M+H]⁺.

2.49 g (10 mmol) of compound 25a and 2.6 g (40 mmol) of sodium azide were added into a flask, and additionally added with 20 mL of DMF as a solvent, the reaction was carried out at 120° C. for 16 hours, and the reaction was monitored by a TLC plate. Water was added for quenching after the reaction, a water phase was extracted with ethyl acetate (180 mL) thrice, organic phases were combined, and washed with water, and the solvent was removed under a reduced pressure to obtain a foamed solid 25b, with a weight of 2.22 g, and a yield of 76%, and MSI-MS: 293.2 [M+H]⁺.

The 25b was used as a raw material to prepare 25c according to the protection method of 1b in Embodiment 1, and the 25c was used as a raw material to prepare a compound 25 according to the method in Embodiment 2, wherein the 1b was replaced by the 25c in equivalent amount, with a yield of 76%. Detection results of the prepared compound 25 were as follows: ¹H NMR (400 MHz, DMSO-d6) δ8.57 (s, 1H), 8.38 (s, 1H), 7.09 (s, 2H), 6.17 (d, 1H), 5.35 (d, 1H), 4.27-4.24 (m, 2H), 4.19 (s, 2H), 4.02 (m, 1H), 3.81 (m, 1H), 1.75 (m, 1H). ¹³C NMR (100 MHz, DMSO-d6) δ158.2, 152.4, 149.8, 140.5, 119.4, 101.2, 78.1, 73.2, 68.4, 57.5. MSI-MS: 373.2 [M+H]⁺.

Embodiment 26: (((((5-(6-amino-9H-purine-9-yl)-3-azide-4-hydroxytetrahydrofuran-2-yl)methoxy)methyl) phosphoryl)bis(oxy))bis(methylene)bis(2,2-dimethylpropionic acid)

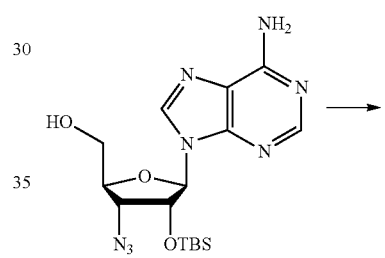

25c

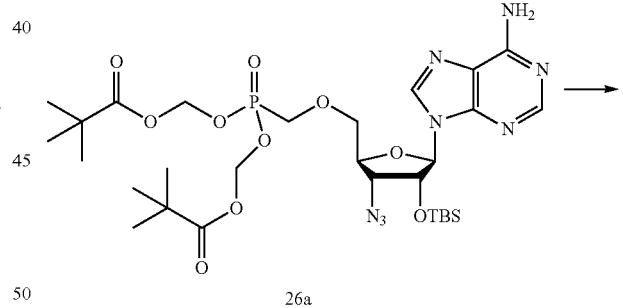

26a

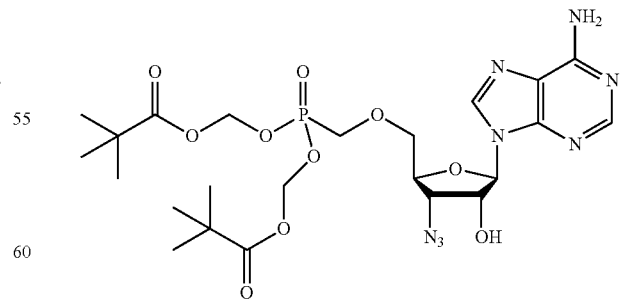

A compound 25c was prepared according to the preparation method in Embodiment 25, the 25c was used as a raw material to prepare a compound 26a according to the preparation method of 17 from 17a in Embodiment 17, and a compound 26 was prepared according to the deprotection method of 1b in Embodiment 1, wherein the 25c was replaced by the 17a in equivalent amount, with a total yield of 54%. Detection results of the prepared compound 26 were as follows: ¹H NMR (400 MHz, DMSO-d6) δ8.58 (s, 1H), 8.34 (s, 1H), 7.04 (s, 2H), 6.82 (s, 4H), 6.15 (d, 1H), 5.35 (d, 1H), 4.00 (m, 2H), 3.85 (s, 2H), 3.62-3.41 (m, 2H), 1.84 (m, 1H), 1.26 (s, 18H). ¹³C NMR (100 MHz, DMSO-d6) δ175.4, 157.3, 152.5, 149.7, 140.2, 119.5, 99.8, 92.8, 79.0, 72.3, 71.5, 71.1, 56.5, 38.8 27.6. MSI-MS: 615.6 [M+H]⁺.

Embodiment 27: isopropyl(((((5-(6-amino-9H-purine-9-yl)-3-azide-4-hydroxytetrahydrofuran-2-yl)methoxy)methyl)(phenoxy)phosphoryl)alanine ester Embodiment 28: isopropyl(((((3-azide-4-hydroxy-5-(6-(isoniazid)-9H-purin-9-yl)tetrahydrofuran-2-yl)methoxy)methyl)(phenoxy)phosphoryl)alanine ester

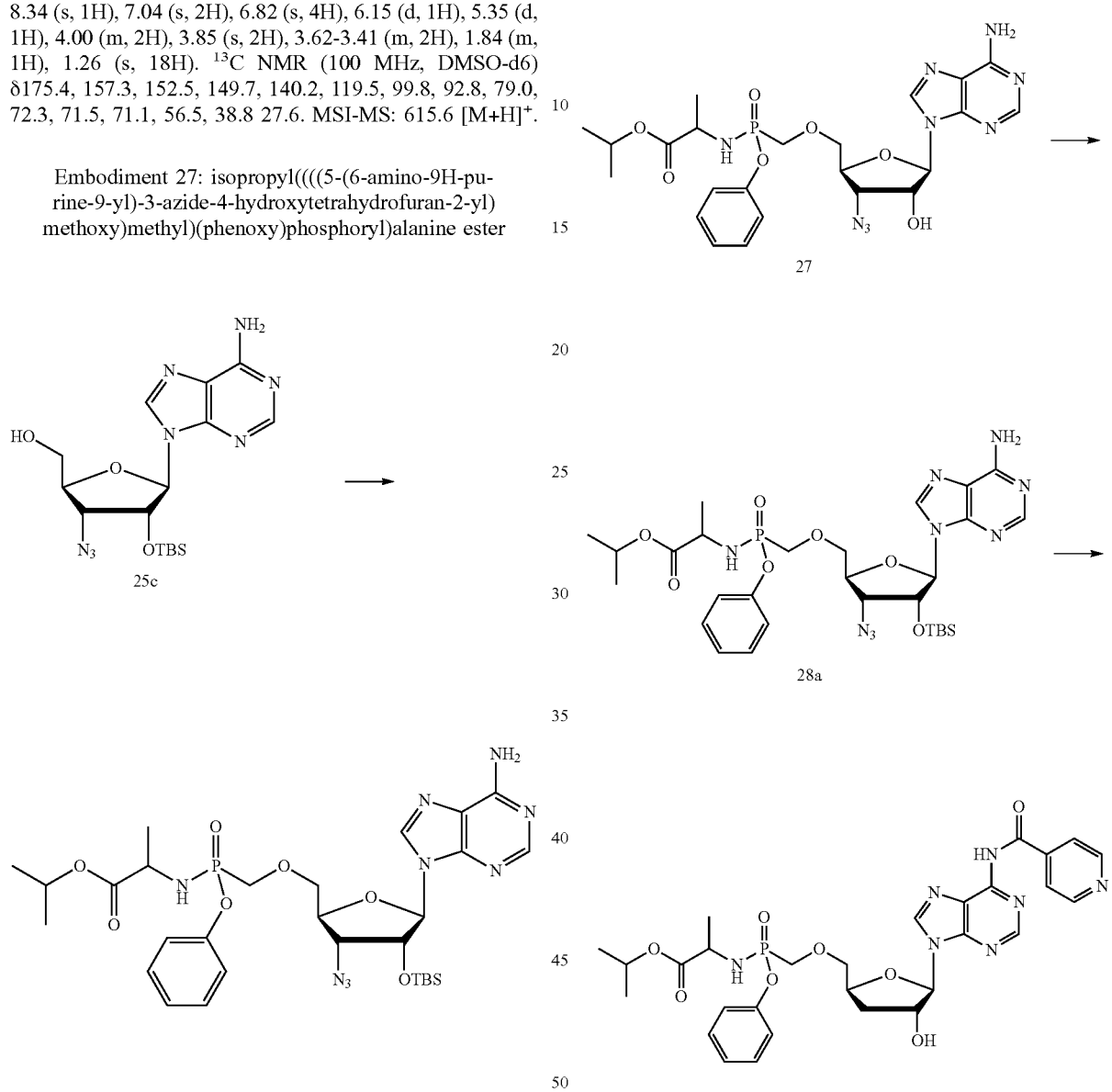

A compound 25c was prepared according to the protection method in Embodiment 25, and the 25c was used as a raw material to prepare a compound 27 according to the preparation method in Embodiment 7, wherein the 1b was replaced by the 25c in equivalent amount, with a total yield of 43%. Detection results of the prepared compound 27 were as follows: ¹H NMR (400 MHz, DMSO-d6) δ8.58 (s, 1H), 8.34 (s, 1H), 7.42 (m, 2H), 7.21 (m, 3H), 7.07 (s, 2H), 6.15 (d, 1H), 5.34 (s, 1H), 4.95 (d, 1H), 3.99 (m, 2H), 3.76-3.34 (m, 6H), 1.88 (m, 1H), 1.27-1.16 (d, 9H). ¹³C NMR (100 MHz, DMSO-d6) δ171.4, 156.4, 152.1, 150.1, 149.5, 140.3, 130.5, 121.2, 120.5, 119.4, 100.5, 78.4, 72.8, 72.0, 71.5, 69.1, 57.2, 50.5, 21.5, 19.1. MSI-MS: 576.5 [M+H]⁺.

The prepared compound 27 was used as a raw material, a compound 28a was prepared according to the protection method of 1a or 1b in Embodiment 1, and the compound 28a was used as a raw material to prepare a compound 28 according to the preparation method in Embodiment 12, wherein cordycepin or the 1b was replaced by the compound 28 in equivalent amount, with a total yield of 37%. Detection results of the prepared compound 28 were as follows: ¹H NMR (400 MHz, DMSO-d6) δ11.07 (s, 1H), 8.83 (d, 2H), 8.35 (s, 1H), 8.20 (s, 1H), 8.01 (d, 2H), 7.41 (m, 2H), 7.21 (m, 3H), 6.15 (d, 1H), 5.35 (s, 1H), 4.94 (d, 1H), 4.00 (m, 2H), 3.72-3.32 (m, 6H), 1.82 (m, 1H), 1.24-1.17 (d, 9H). ¹³C NMR (100 MHz, DMSO-d6) δ171.5, 164.5, 152.1, 151.6, 150.1, 149.8, 149.4, 140.7, 140.3, 130.2, 122.2, 121.5, 121.1, 120.4, 100.4, 78.7, 72.5, 72.1, 71.5, 69.2, 57.4, 50.8, 21.6, 19.2. MSI-MS: 681.6 [M+H]⁺.

Embodiment 29: 2-(6-amino-9H-purin-9-yl)-5-(hydroxymethyl)tetrahydrofuran-3-yl valine salt

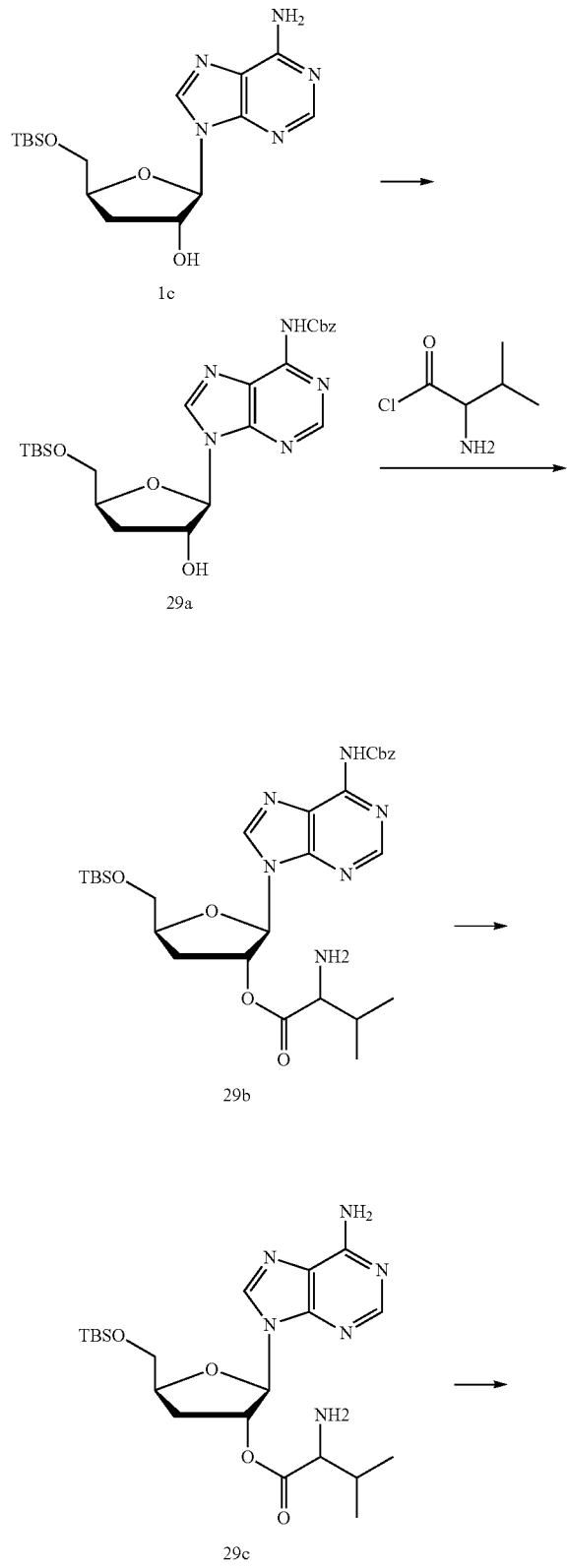

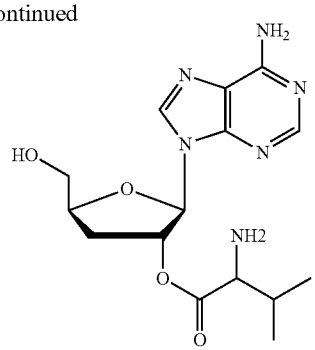

A compound 1c was prepared according to the protection method of 1c in Embodiment 1, the 1c was used as a raw material for further reaction, 9.95 g (27.2 mmol) of compound 1c and 4.88 g (27.2 mmol) of CbzCl were added into 38.5 mL of toluene and 38.5 mL of water, and additionally added with 4.70 g (34 mmol) of $K_2CO_3$, and the mixture was vigorously stirred at a temperature below 25° C. Subsequently, the mixture was stirred at room temperature for 3 hours, and then added with 0.275 g (2.72 mmol) of triethylamine and 5.78 g of sodium chloride in sequence, and the mixture was continuously stirred for 30 minutes. An organic layer was separated and concentrated to obtain a required oil product 29a, with a weight of 13.1 g, and a yield of 90%, and MSI-MS: 522.6 [M+Na]$^+$.

4.99 g (10 mmol) of compound 29a and 1.36 g (10 mmol) of valine acyl chloride were added with 60 mL of anhydrous pyridine in ice bath, the reaction was gradually subjected to temperature rise to 40° C. for reaction for 10 hours, the reaction was monitored by TLC, water and ethyl acetate were added for extraction after the reaction, an organic phase was reverse-extracted, the organic phase was collected for rotary evaporation to obtain an oil liquid 10b, and the oil liquid 10b was purified by column chromatography to obtain 5.03 g of purified product of 29b, with a yield of 84%, and MSI-MS: 625.5 [M+Na]$^+$.

5.99 g of compound 29b (10 mmol) was dissolved in 200 mL of methanol. Subsequently, 1.5 g of ammonium formate (30 mmol) and 0.75 g of 10% Pd—C were added, and the reaction mixture was stirred at room temperature for 10 minutes, and then heated and refluxed for 45 minutes. The mixture was filtered through diatomaceous earth, and the filtrate was evaporated to be dry to obtain 4.41 g of compound 29c, with a yield of 95%. The 29c was used as a raw material to prepare a compound 29 by deprotection according to the method of 1c in Embodiment 1, with a yield of 90%. Detection results of the prepared compound 29 were as follows: $^1$H NMR (400 MHz, DMSO-d6) δ8.89 (s, 2H), 8.58 (s, 1H), 8.37 (s, 1H), 7.05 (s, 2H), 6.73 (d, 1H), 5.01 (m, 1H), 4.92 (s, 1H), 4.27 (m, 1H), 3.75 (m, 1H), 3.56-3.47 (m, 2H), 2.38 (m, 1H), 2.13 (m, 1H), 1.89 (m, 1H), 0.98 (d, 6H). $^{13}$C NMR (100 MHz, DMSO-d6) δ172.1, 156.0, 152.3, 149.5, 140.1, 119.4, 102.2, 82.5, 74.4, 63.7, 59.5, 33.1, 30.5, 19.1. MSI-MS: 351.3 [M+H]$^+$.

Embodiment 30: 2-(6-amino-9H-purin-9-yl)-5-(phosphonoxy)methyl)tetrahydrofuran-3-yl valine salt

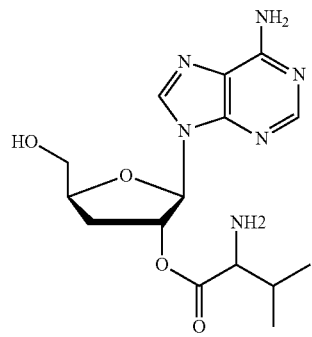

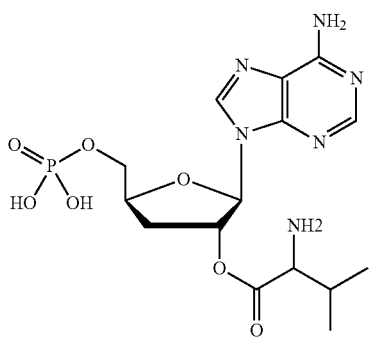

A compound 29 was used as a raw material to prepare a compound 30 by reaction according to the method in Embodiment 2, wherein the 1b was replaced by the 29 in equivalent amount to prepare the compound 30, with a yield of 84%. Detection results of the prepared compound 30 were as follows: ¹H NMR (400 MHz, DMSO-d6) δ8.90 (s, 2H), 8.56 (s, 1H), 8.33 (s, 1H), 7.04 (s, 2H), 6.75 (d, 1H), 5.00 (m, 1H), 4.27-4.02 (m, 5H), 3.73 (m, 1H), 2.36 (m, 1H), 2.16 (m, 1H), 1.88 (m, 1H), 0.96 (d, 6H). ¹³C NMR (100 MHz, DMSO-d6) δ172.4, 156.3, 152.5, 149.8, 140.2, 119.5, 101.2, 76.1, 74.2, 68.7, 59.3, 32.1, 30.4, 19.0. MSI-MS: 431.3 [M+H]⁺.

Embodiment 31: 2-(6-(isonicotinamide)-9H-purin-9-yl)-5-(phosphonyl)methyl)tetrahydrofuran-3-yl valine salt

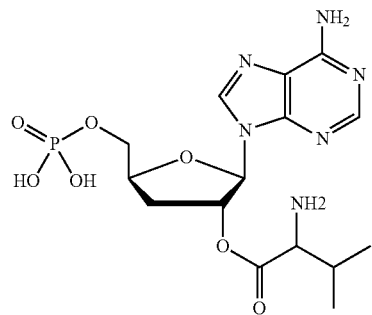

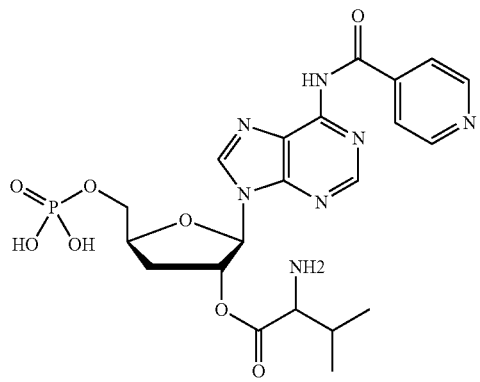

A compound 30 was used as a raw material to prepare a compound 31 according to the preparation method in Embodiment 12, wherein the 1a was replaced by the compound 30 in equivalent amount, with a yield of 91%. Detection results of the prepared compound 31 were as follows: ¹H NMR (400 MHz, DMSO-d6) δ11.08 (s, 1H), 8.92 (s, 2H), 8.82 (d, 2H), 8.34 (s, 1H), 8.20 (s, 1H), 8.02 (d, 2H), 6.73 (d, 1H), 5.03 (m, 1H), 4.29-4.01 (m, 5H), 3.75 (m, 1H), 2.39 (m, 1H), 2.15 (m, 1H), 1.88 (m, 1H), 0.97 (d, 6H). ¹³C NMR (100 MHz, DMSO-d6) δ171.4, 164.5, 152.3, 151.1, 149.9, 149.7, 140.5, 140.1, 123.7, 121.5, 101.7, 77.1, 74.5, 68.2, 59.8, 32.4, 30.8, 19.2. MSI-MS: 558.4 [M+Na]⁺.

Embodiment 32: (((5-(6-(isonicotinamide)-9H-purine-9-yl)-4-(pentoxy)tetrahydrofuran-2-yl)methoxy)methyl)phosphonic acid

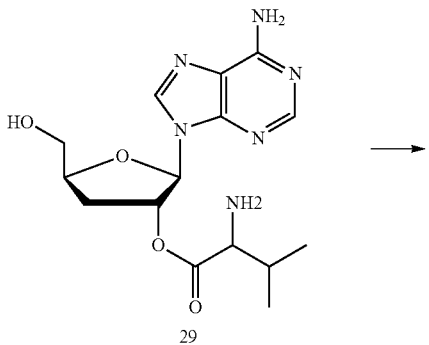

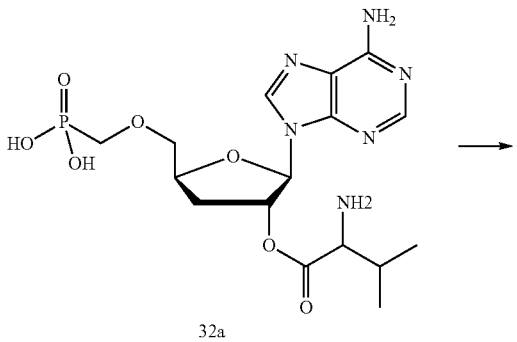

32a

75
-continued

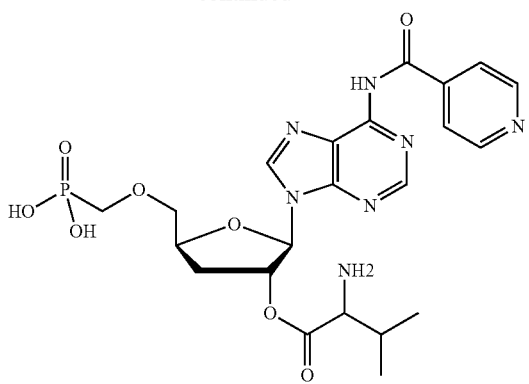

76

A compound 29 was used as a raw material to prepare a compound 32a according to the preparation method in Embodiment 3, wherein the compound 1b was replaced by the compound 29 in equivalent amount, with a yield of 77%. The compound 32a was used as a substrate to prepare a compound 32 according to the preparation method in Embodiment 12, wherein the 1a was replaced by the compound 32a in equivalent amount, with a yield of 90%. Detection results of the prepared compound 32 were as follows: $^1$H NMR (400 MHz, DMSO-d6) δ11.05 (s, 1H), 8.91 (s, 2H), 8.84 (d, 2H), 8.35 (s, 1H), 8.18 (s, 1H), 8.01 (d, 2H), 6.75 (d, 1H), 5.01 (m, 1H), 4.81 (s, 2H), 4.24 (m, 1H), 3.95 (m, 1H), 3.73 (d, 2H), 3.60-3.35 (m, 2H), 2.37 (m, 1H), 2.14 (m, 1H), 1.89 (m, 1H), 0.96 (d, 6H). $^{13}$C NMR (100 MHz, DMSO-d6) δ171.5, 165.5, 152.4, 151.1, 149.8, 140.7, 140.1, 123.5, 121.7, 102.7, 76.8, 76.6, 75.5, 74.3, 59.5, 32.5, 30.5, 18.9. MSI-MS: 550.4 [M+H]$^+$.

Embodiment 33: methyl(((2-(6-amino-9H-purin-9-yl)-5-(hydroxymethyl)tetrahydrofuran-3-yl)oxy)(phenoxy)phosphoryl)alanine salt

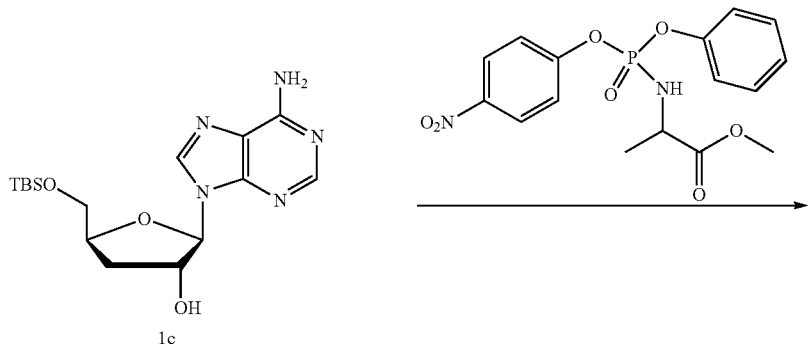

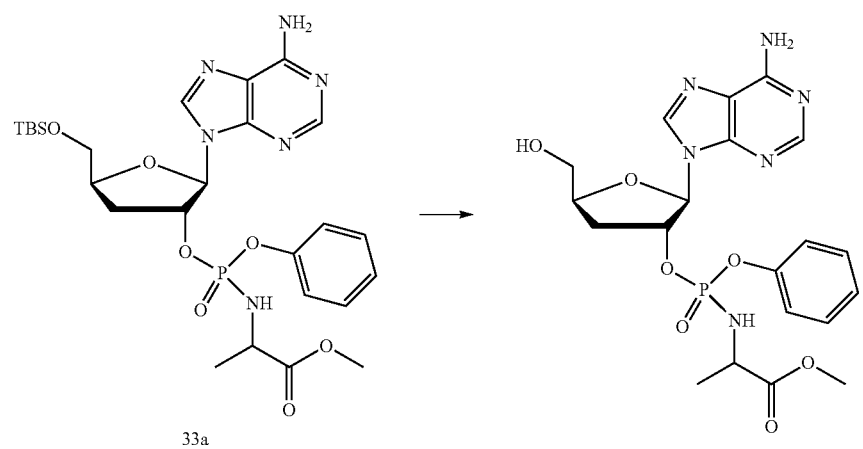

A compound 1c was used as a raw material to prepare a compound 33a according to the preparation method in Embodiment 6, wherein the compound 1b was replaced by the compound 1c in equivalent amount, with a yield of 62%, and a compound 33 was prepared by reacting the 33a according to the deprotection solution of 1c in Embodiment 1, with a yield of 90%. Detection results of the prepared compound 33 were as follows: $^1$H NMR (400 MHz, DMSO-d6) δ8.58 (s, 1H), 8.33 (s, 1H), 7.42 (m, 2H), 7.21 (m, 3H), 7.08 (s, 2H), 6.15 (d, 1H), 5.00 (m, 1H), 4.02 (m, 1H), 3.71-3.48 (m, 8H), 2.24-1.98 (m, 2H), 1.25 (d, 3H). $^{13}$C NMR (100 MHz, DMSO-d6) δ172.1, 156.1, 152.4, 149.9, 149.6, 140.3, 131.0, 121.5, 120.2, 119.6, 101.8, 82.1, 74.3, 63.4, 52.1, 46.2, 32.5, 19.2. MSI-MS: 439.4 [M+H]$^+$.

Embodiment 34: methyl(((5-(hydroxymethyl)-2-(6-(isonicotinamide)-9H-purin-9-yl)tetrahydrofuran-3-yl)oxy)(phenoxy)phosphoryl)alanine salt

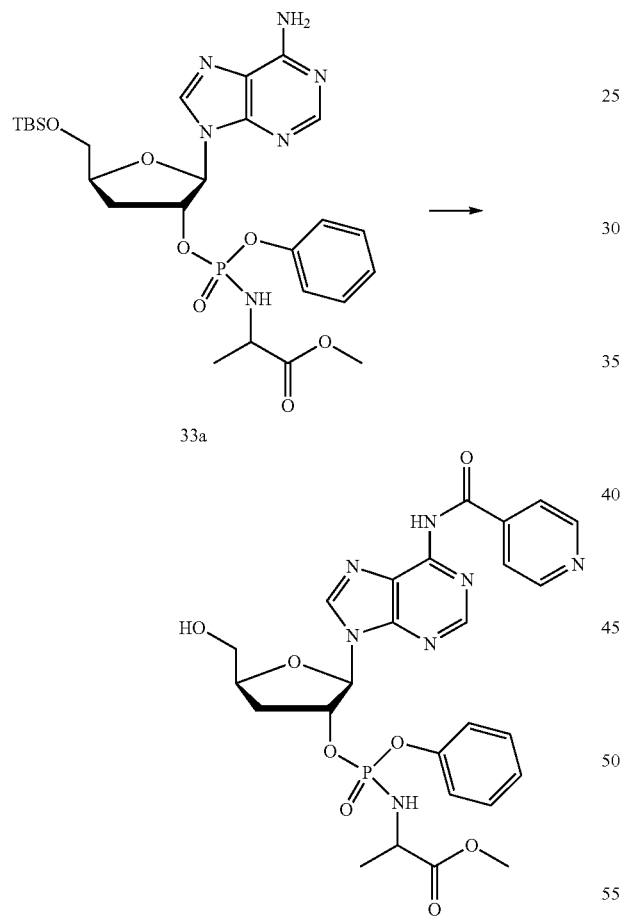

A compound 33a was prepared according to the process in Embodiment 33, and the 33a was used as a raw material to prepare a compound 34 according to the preparation method in Embodiment 12, wherein the 1a was replaced by the compound 33a in equivalent amount, with a total yield of 83%. Detection results of the prepared compound 34 were as follows: $^1$H NMR (400 MHz, DMSO-d6) δ11.02 (s, 1H), 8.81 (d, 2H), 8.34 (s, 1H), 8.17 (s, 1H), 8.02 (d, 2H), 7.41 (m, 2H), 7.23 (m, 3H), 6.16 (d, 1H), 4.98 (m, 1H), 4.01 (m, 1H), 3.78-3.47 (m, 8H), 2.25-1.97 (m, 2H), 1.27 (d, 3H). $^{13}$C NMR (100 MHz, DMSO-d6) δ171.4, 163.8, 152.1, 151.5, 150.4, 149.8, 149.7, 140.8, 140.5, 130.2, 122.5, 121.7, 121.2, 119.9, 102.4, 82.5, 74.5, 63.5, 51.7, 46.3, 32.7, 19.4. MSI-MS: 598.5 [M+H]$^+$.

Embodiment 35: (5-(2-((E)-2-bromocarbonyl)-6-(isonicotinamide)-9H-purin-9-yl)-4-hydroxytetrahydrofuran-2-yl)dihydromethyl phosphate

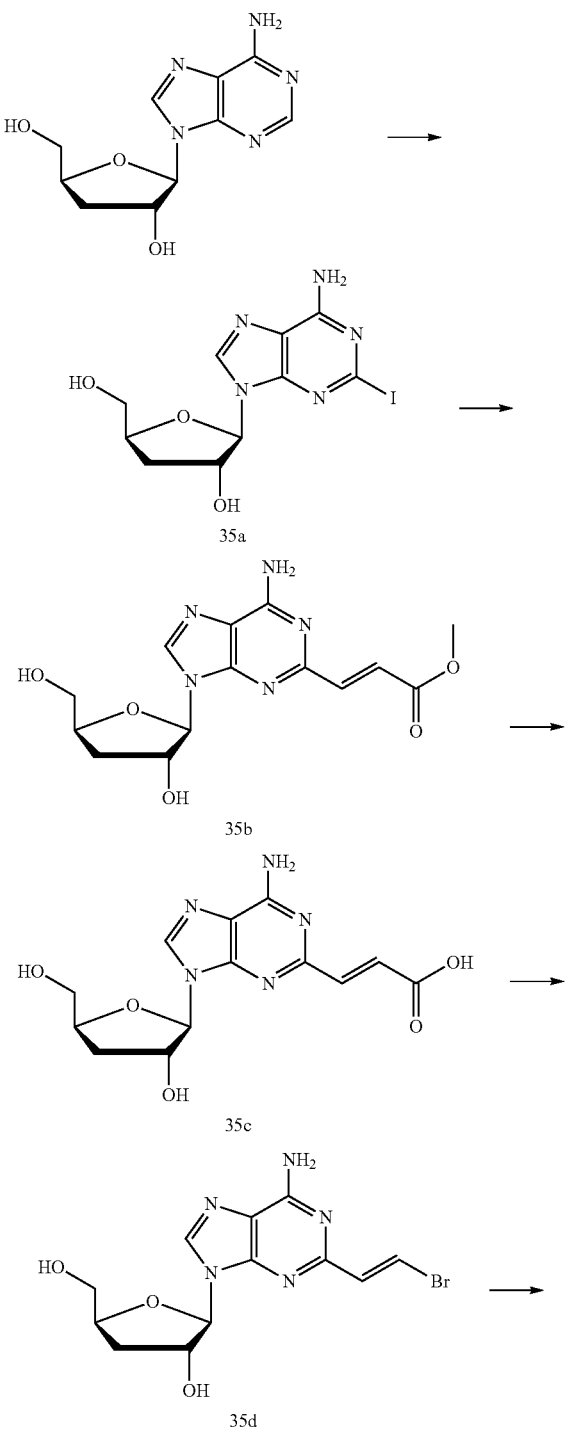

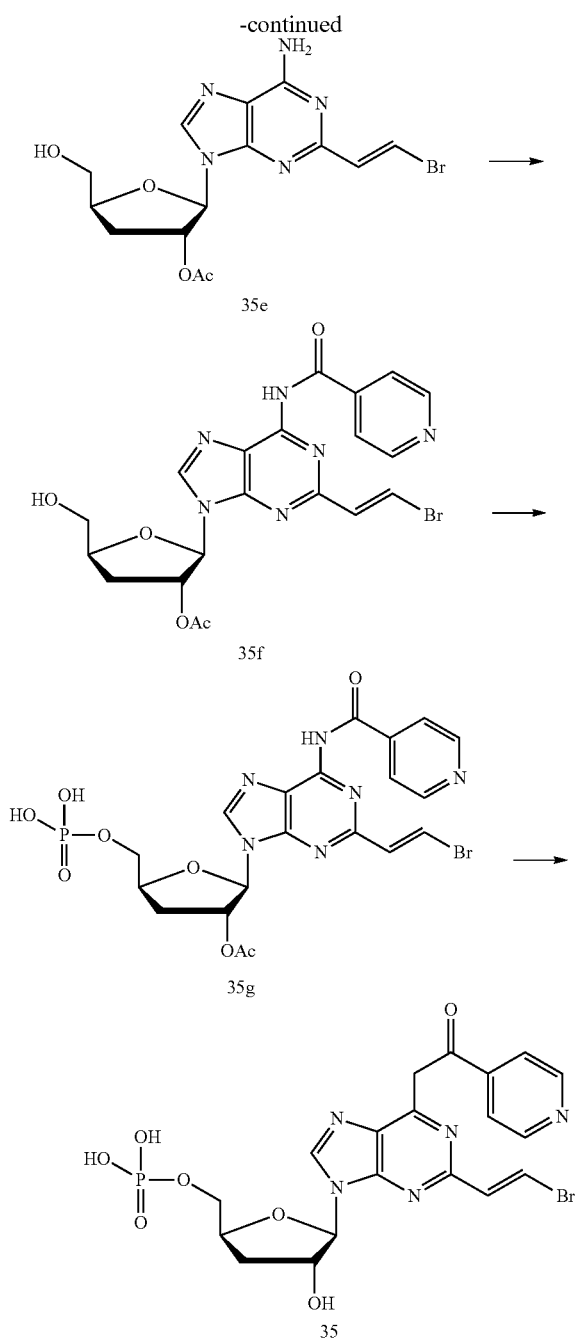

acrylate were added, the reaction was carried out at 80° C. for 2 hours and then finished, the mixture was filtered, and the filtrate was collected, allowed to stand, and then filtered again to obtain a white flocculent solid, which was a compound 35b, with a weight of 2.41 g, and a yield of 72.7%, and MSI-MS: 336.4 [M+H]+.

g of compound 35b was dropwise added with 12 mL of sodium hydroxide solution (2 mol/L), stirred at room temperature for 3 hours, and then dropwise added with concentrated hydrochloric acid in ice bath until a pH value was 1. At the moment, a large number of white precipitates were generated. A white solid 35c was obtained by suction filtration, with a weight of 0.88 g, and a yield of 92%, and MSI-MS: 322.6 [M+H]+.

3.21 g (10 mmol) of compound 35c was added into 120 mL of water, heated to 100° C. and stirred, and then added with 2.07 g (15 mmol) of anhydrous potassium carbonate, 2.67 g (15 mmol) of NBS was dissolved in 22.5 mL of acetone and 22.5 mL of water respectively, and the mixed solution was dropwise added into a flask, which was finished within 135 minutes. The mixture was stirred for 3 hours, the reaction was stopped, a half of the solvent was removed, and the remaining solution was placed in a refrigerator overnight. A large number of needle-like brown crystals were precipitated and subjected to suction filtration to obtain a compound 35d, with a weight of 1.78 g, and a yield of 50%, and MSI-MS: 357.3 [M+H]+.

1.78 g (5 mmol) of compound 35d was added with 40.00 mL of anhydrous pyridine and 8.5 mL of acetic anhydride in ice bath. The reaction was monitored by HPLC, and the reaction was ended after reacting for about 5 hours. The solvent was removed to obtain a viscous liquid 35e, with a weight of 1.76 g, and a yield of 80%. The compound 35e was prepared into a compound 35f by the method in Embodiment 16, with a yield of 95%; and the compound 35f was prepared into a compound 35 by the phosphorylation method in Embodiment 2 and the deprotection method in Embodiment 1, with a yield of 72%. Detection results of the prepared compound 35 were as follows: $^1$H NMR (400 MHz, DMSO-d6) δ11.05 (s, 1H), 8.84 (d, 2H), 8.31 (s, 1H), 8.02 (d, 2H), 7.11 (d, 1H), 6.70 (d, 1H), 6.11 (d, 1H), 5.35 (s, 1H), 4.31-4.02 (m, 5H), 3.76 (m, 1H), 2.07-1.84 (m, 2H). $^{13}$C NMR (100 MHz, DMSO-d6) δ164.5, 152.6, 151.8, 149.8, 149.7, 140.9, 140.3, 134.5, 124.3, 123.4, 121.5, 98.5, 74.5, 74.3, 68.5, 34.7. MSI-MS: 542.2 [M+H]+.

Embodiment 36: 3-((5-(6-amino-2-fluoro-9H-purin-9-yl)-4-hydroxytetrahydrofuran-2-yl)methoxy)-5-(hydroxymethyl)cyclopentane-1,2-diol 2.51 g (10 mmol) of cordycepin was dissolved in dilute nitric acid, heated to 110° C., and added with 1.26 g (5 mmol) of elemental iodine for reaction for 4 hours, and the reaction was monitored by TLC. The mixture was extracted with petroleum ether after the reaction, a water phase was collected, an organic phase solution was extracted with deionized water, and water phases were combined for rotary evaporation to obtain a compound 35a, with a weight of 2.72 g, and a yield of 72%, and MSI-MS: 378.2 [M+H]+.

100 mL of anhydrous 1,4-dioxane was added into a reactor, introduced with argon for protection, heated to 70° C., added with 0.11 g (0.5 mmol) of palladium acetate, 0.26 g (1 mmol) of triphenylphosphine and 1.8 mL of triethylamine in sequence, and stirred for about 30 minutes. 3.77 g (10 mmol) of compound 35a and 2.59 g (30 mmol) of methyl

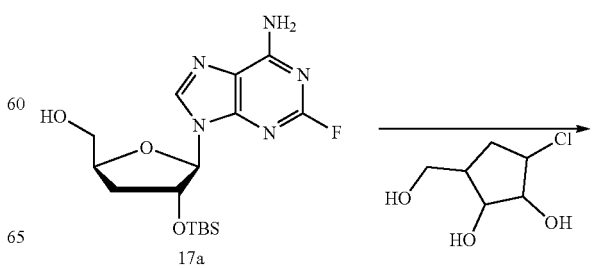

17a

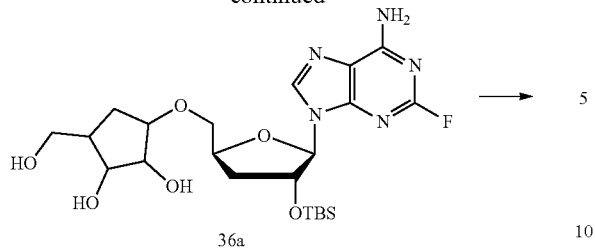

36a

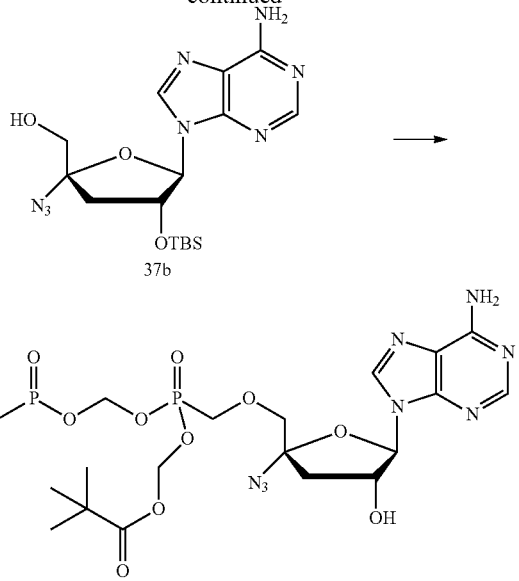

37b

A compound 17a was prepared according to the method in Embodiment 17, and the 17a was used as a raw material to prepare a compound 36a according to the preparation method in Embodiment 8, wherein 2-chloro-3-hydroxypropyl valine was replaced by 3-chloro-5-(hydroxymethyl)cyclopentane-1,2-diol in equivalent amount, and a compound 36 was prepared after deprotecting the compound 36a, with a total yield of 41%. Detection results of the prepared compound 36 were as follows: $^1$H NMR (400 MHz, DMSO-d6) δ8.37 (s, 1H), 7.01 (s, 2H), 6.15 (d, 1H), 5.92 (s, 1H), 5.37 (d, 1H), 4.38 (s, 1H), 4.25 (s, 1H), 4.02 (m, 2H), 3.84 (m, 1H), 3.65-3.31 (m, 6H), 2.07-1.82 (m, 2H), 1.70-1.44 (m, 3H). $^{13}$C NMR (100 MHz, DMSO-d6) δ156.1, 153.5, 149.8, 140.3, 119.5, 99.2, 83.5, 81.2, 76.2, 75.7, 74.8, 73.1, 64.1, 34.9, 34.7, 31.5. MSI-MS: 416.8 [M+H]$^+$.

Embodiment 37: Preparation of Compound: (((((5-(6-amino-9H-purine-9-yl)-2-azide-4-hydroxytetrahydrofuran-2-yl)methoxy)methyl)phosphoryl)bis(oxy)bis(methylene)bis(2,2-dimethylpropionic acid), with a Preparation Process as Follows

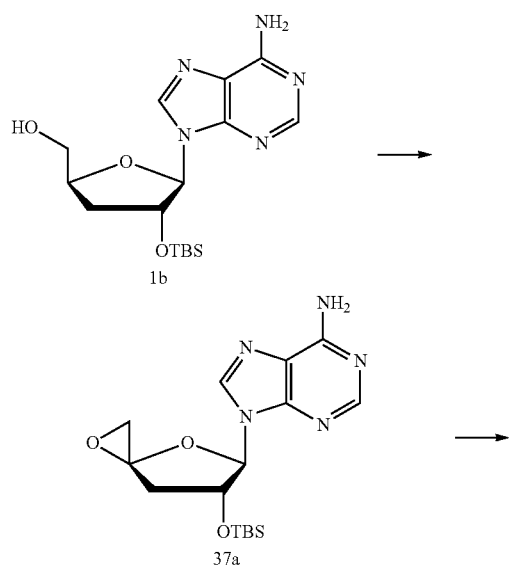

3.65 g (10 mmol) of compound 1b and 3.44 g (20 mmol) of m-chloroperoxybenzoic acid were added into a reaction flask, added with 100 mL of anhydrous dichloromethane for dissolution, and additionally added with 2.13 g (15 mmol) of phosphorus pentoxide in ice bath, and the reaction was gradually subjected to temperature rise to 40° C. for 3 hours. The mixture was filtered after the reaction, added with 100 mL of saturated sodium bicarbonate for a quenching reaction, additionally washed with 50 mL of dichloromethane twice, and reversely extracted with 60 mL of saturated sodium bicarbonate twice, organic phases were combined, concentrated under a reduced pressure, and subjected to column chromatography to obtain a compound 37a, with a weight of 1.49 g, and a yield of 41%. The prepared compound was detected as follows: $^1$H NMR (400 MHz, DMSO-d6) δ8.56 (s, 1H), 8.36 (s, 1H), 7.10 (s, 2H), 6.16 (d, 1H), 4.02 (s, 1H), 2.75-2.45 (m, 2H), 2.13 (d, 2H), 0.99 (s, 9H), 0.22 (s, 6H). $^{13}$C NMR (100 MHz, DMSO-d6) δ156.5, 152.5, 149.8, 140.4, 119.6, 102.5, 85.9, 69.3, 52.7, 42.5, 30.8, 25.8, 0. MSI-MS: 364.5 [M+H]$^+$.

3.63 g (10 mmol) of compound 37a and 2.6 g (40 mmol) of sodium azide were added into a flask, and additionally added with 20 mL of DMF as a solvent, the reaction was carried out at 120° C. for 16 hours, and the reaction was monitored by a TLC plate. Water was added for quenching after the reaction, a water phase was extracted with ethyl acetate (180 mL) thrice, organic phases were combined, and washed with water, and the solvent was removed under a reduced pressure to obtain a foamed solid 37b, with a weight of 2.77 g, and a yield of 68%. The 37b was used as a raw material to prepare a compound 37 according to the preparation method of the compound 17 from the compound 17a in Embodiment 17, wherein the compound 37b was replaced by the 17a in equivalent amount, with a total yield of 50%. Detection results of the prepared compound 37 were as follows: $^1$H NMR (400 MHz, DMSO-d6) δ8.58 (s, 1H), 8.34 (s, 1H), 7.07 (s, 2H), 6.82 (d, 4H), 6.15 (d, 1H), 5.34 (d, 1H), 4.02 (m, 1H), 3.84 (d, 2H), 3.61-3.42 (m, 2H), 2.11-1.80 (m, 2H), 1.28 (d, 18H). $^{13}$C NMR (100 MHz, DMSO-d6) δ175.2, 156.3, 152.6, 149.9, 140.2, 119.4, 100.3, 93.1, 90.2, 81.0, 71.5, 68.8, 38.6, 36.2, 27.4. MSI-MS: 637.6 [M+Na]$^+$.

Embodiment 38: Preparation of Compound: (5-(6-amino-2-((E)-2-bromocarbonyl)-9H-purine-9-yl)-4-hydroxytetrahydrofuran-2-yl)dihydromethyl phosphate, with a Reaction Process as Follows

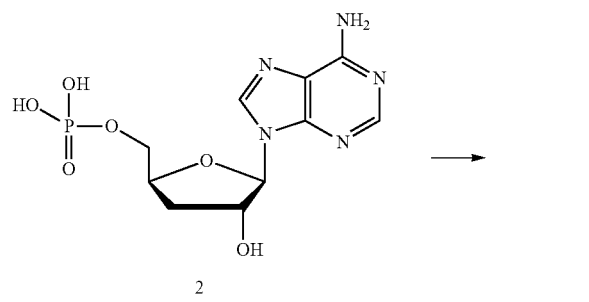

2

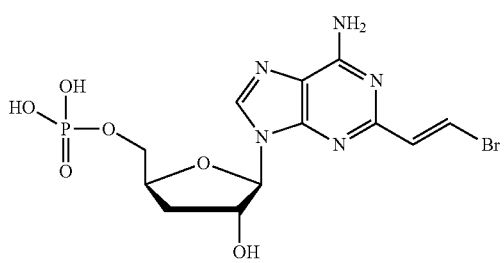

A compound 2 was used as a raw material to prepare a compound 38 from the compound 2 according to the method in Embodiment 35, with an overall yield of 24%. Detection results of the prepared compound 38 were as follows: $^1$H NMR (400 MHz, DMSO-d6) δ8.35 (s, 1H), 7.09 (d, 1H), 6.95 (s, 2H), 6.68 (d, 1H), 6.15 (d, 1H), 5.35 (s, 1H), 4.27-4.02 (m, 5H), 3.74 (m, 1H), 2.07-1.84 (m, 2H). $^{13}$C NMR (100 MHz, DMSO-d6) δ156.1, 152.3, 149.8, 140.2, 134.9, 124.2, 119.5, 98.7, 74.9, 74.3, 68.1, 34.5. MSI-MS: 458.3 [M+N]$^+$.

Embodiment 39: Preparation of Compound: (5-(6-amino-8-(isopropylamino)-9H-purin-9-yl)-4-hydroxytetrahydrofuran-2-yl)dihydromethyl phosphate, with a Preparation Process as Follows

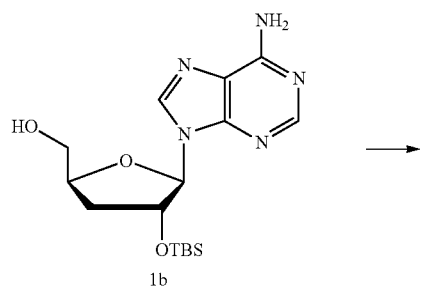

1b

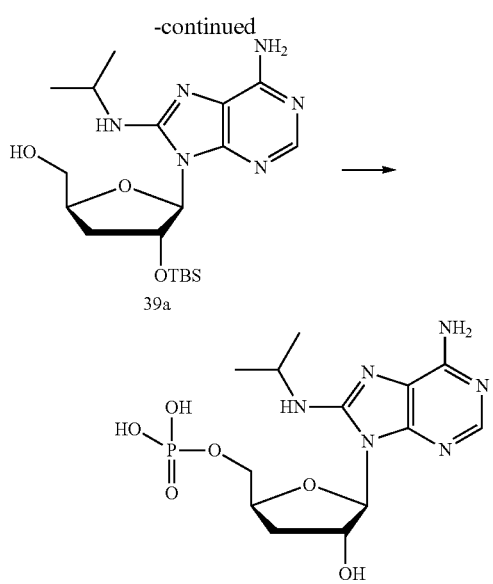

A compound 1b was used as a raw material to prepare a compound 39. 3.65 g (10 mmol) of compound 1b and 1.18 g (20 mmol) of 2-propylamine were added into a reaction flask first, and added with 60 mL of dioxane as a solvent, the mixture was refluxed at 80° C. for reaction for 20 hours, and the reaction was monitored by TLC. The reaction solution was concentrated after the reaction, and then added with 50 mL of water and 50 mL of ethyl acetate for extraction twice, organic phases were combined, and concentrated under a reduced pressure to obtain an oil liquid, and the oil liquid was purified by column chromatography to obtain a light yellow oil liquid, which was a compound 39a, with a weight of 1.44 g and a yield of 34%.

The compound 39a was used as a raw material to prepare a compound 39 according to the preparation method in Embodiment 2, wherein the 1b was replaced by the 39a in equivalent amount, with a yield of 91%. Detection results of the prepared compound 39 were as follows: $^1$H NMR (400 MHz, DMSO-d6) δ8.15 (s, 1H), 7.05 (s, 2H), 6.15 (d, 1H), 5.98 (s, 1H), 5.38 (s, 1H), 4.28-3.95 (m, 6H), 3.75 (m, 1H), 2.05-1.81 (m, 2H), 1.18 (d, 6H). $^{13}$C NMR (100 MHz, DMSO-d6) δ153.1, 152.3, 151.5, 149.8, 118.5, 99.7, 74.8, 74.5, 68.5, 46.5, 34.3, 23.5. MSI-MS: 389.3 [M+H]$^+$.

Embodiment 40: Preparation of Compound: 3-((5-(6-amino-9H-purin-9-yl)-4-hydroxytetrahydrofuran-2-yl)methoxy)-5-(hydroxymethyl)cyclopentane-1,2-diol, with a Preparation Process as Follows

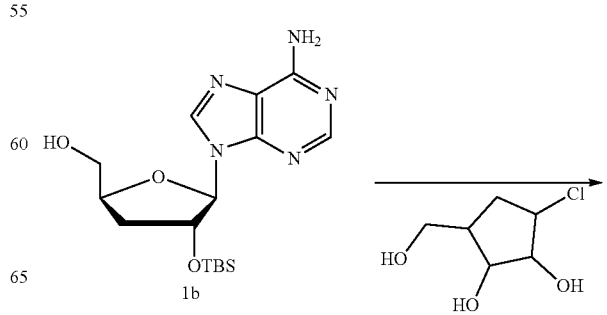

1b

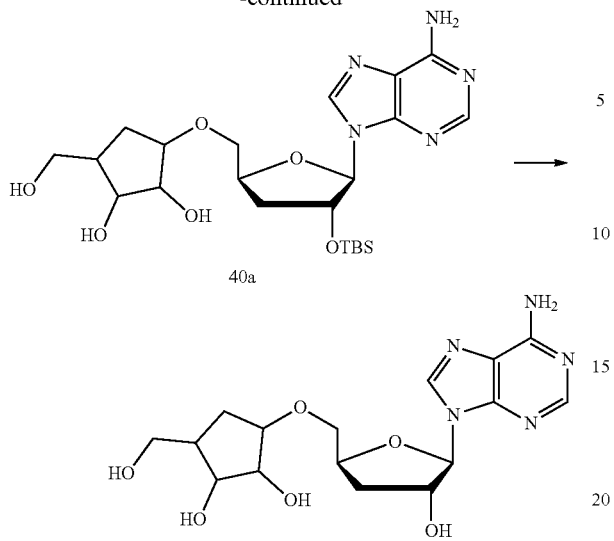

A compound 1b was used as a raw material to prepare a compound 40 according to the preparation method in Embodiment 8, wherein 2-chloro-3-hydroxypropyl valine was replaced by 3-chloro-5-(hydroxymethyl)cyclopentane-1,2-diol in equivalent amount, with a total yield of 46%. Detection results of the prepared compound 40 were as follows: $^1$H NMR (400 MHz, DMSO-d6) δ8.58 (s, 1H), 8.37 (s, 1H), 7.04 (s, 2H), 6.15 (d, 1H), 5.91 (s, 1H), 5.37 (d, 1H), 4.37 (s, 1H), 4.25 (s, 1H), 4.00 (m, 2H), 3.82 (m, 1H), 3.63-3.32 (m, 6H), 2.08-1.81 (m, 2H), 1.71-1.45 (m, 3H). $^{13}$C NMR (100 MHz, DMSO-d6) δ156.3, 153.4, 149.7, 140.2, 119.4, 99.5, 83.4, 81.1, 76.1, 75.5, 74.9, 73.6, 64.4, 34.9, 34.7, 31.6. MSI-MS: 382.3 [M+H]$^+$.

Embodiment 41: Anti-Tumor Experimental Effect of Modified Derivative of Cordycepin on Liver Cancer A mouse transplanted liver cancer model was established and a drug was evaluated. 2.5×10$^5$ Hep-1-6 liver cancer cells were suspended in 100 μL of PBS to be inoculated into an outer side of thigh of left lower limb of C57BL/6j nude mice. One week later, when the transplanted tumor reached about 100 mm$^3$, the mice were randomly divided into 12 groups, with 10 mice in each group, comprising a blank group, a cordycepin control group and drug groups (compounds 2, 3, 5, 7, 15, 24, 27, 31, 35, and 40). The blank group was intragastrically administered with a nutritional agent such as a corn steep liquor and DMSO as a solvent control every other day, and the cordycepin control group and the drug groups were intragastrically administered with a compound drug (500 ug/time/animal) respectively every other day, and the groups were continuously observed for 14 days. Changes of tumor sizes of liver tumors in the two groups of mice were observed, the mice were killed after the experiment, blood and corresponding tissue samples were collected, tumor bodies were immediately photographed and weighed, and some tumor tissues were fixed in a formalin solution to be further detected. Two vertical diameters (length and width) of the transplanted tumor were measured with a caliper every two days to calculate a size of the transplanted tumor. Experimental results of changes of tumor volumes and tumor results treated in the blank group, the cordycepin control group and the drug groups within 14 days were shown in FIG. 1. The volume was calculated according to formula: tumor volume (mm$^3$)=½×(length×width)$^2$. The experimental results show that the separate use of the drug groups can obviously inhibit the growth of tumors in mice, with an effect better than that of the cordycepin control group, wherein the compound 24 has an excellent anti-tumor effect (reduced from 900 mm$^3$ to <100 mm$^3$)(P<0.001), indicating that the compound drug groups have an efficacy of killing the liver cancer cells or an efficacy of activating tumor immunity.

Embodiment 42: Anti-Tumor Experimental Effect of Modified Derivative of Cordycepin on Small Cell Lung Cancer Anti-tumor dose-effect relationship curves of cordycepin and compounds 1, 2, 4, 5, 7, 8, 10, 12, 16, 18, 21, 23, 24, 35 and 38 in small cell lung cancer cell lines H1048, H446 and H69 were analyzed by an MTT experimental method. Calculation results of median inhibitory concentration (IC$_{50}$) were summarized as shown in the table below. Results of an in-vitro anti-tumor experiments show that, compared with the cordycepin, an effective concentration of a modified cordycepin derivative on tumor cells is reduced, wherein the compounds 35 and 38 both have a strong killing effect on the three lines of cells in vitro, but the compounds also have higher toxicity, followed by the compounds 18 and 21. The IC$_{50}$ values of the cordycepin in the small cell lung cancer cell lines H1048 and H446 are both higher than 100 μM, with a high concentration of action, so that a large amount of drug may be needed to take effect in practical application.

TABLE 1

| Compound number | IC$_{50}$ (μM) of compounds in three lines of small cell lung cancer cells | | |
|---|---|---|---|
| | H446 | H1048 | H69 |
| Cordycepin | 123.10 | 171.60 | 63.12 |
| 1 | 23.77 | 27.45 | 20.59 |
| 2 | 76.75 | 55.33 | 50.17 |
| 4 | 54.34 | 42.14 | 43.17 |
| 5 | 43.34 | 40.92 | 53.39 |
| 7 | 20.46 | 12.10 | 9.59 |
| 8 | 10.45 | 14.47 | 14.78 |
| 10 | 12.14 | 10.41 | 9.48 |
| 12 | 18.12 | 22.17 | 19.47 |
| 16 | 19.06 | 25.54 | 23.30 |
| 18 | 6.53 | 4.31 | 6.74 |
| 21 | 4.58 | 6.38 | 2.95 |
| 23 | 16.45 | 17.35 | 20.17 |
| 24 | 17.16 | 24.38 | 25.48 |
| 35 | 21.43 | 32.57 | 21.48 |
| 38 | 0.97 | 1.37 | 1.25 |

Embodiment 43: Determination of Maximum Tolerance Dose of Modified Derivative of Cordycepin to In-Vivo Experiment of Zebrafish 240 3 dpf wild-type AB-line zebrafish were randomly selected in an 8-well plate, with 30 zebrafish in each well, and 3 mL of fish culture water in each well, the cordycepin was diluted according to a maximum lethal dose, dissolved in DMSO, and added into each well according to a concentration gradient (the maximum lethal dose was diluted by 100 times, in which 8 concentration gradient values were taken for the experiment), and meanwhile, a normal control group, a solvent control group G (5% glucose) and a solvent control group D (DMSO) were set. During the experiment, the zebrafish in each group were cultured at 35° C., after the zebrafish were treated to be 5 dpf with a sample to be tested, lethal and developmental malformation conditions of the zebrafish in different doses were investigated respectively, and a maximum tolerance dose (MTD) of the sample to be tested to normal zebrafish was determined under a concentration when survival rate>90% and teratogenicity<20%. The cordycepin was selected as the control group, and other compounds 2, 5, 6, 7, 9, 11, 13, 20, 24, 25, 28, 35, 36, 37 and 39 were selected to test the MTD to the zebrafish according to the above method. Test results were shown in Table 2.

TABLE 2

Maximum tolerance doses (MTD) of natural products and positive control drug in zebrafish model

| Compound number | MTD |
|---|---|
| Cordycepin | 995 μM |
| 2 | 845 μM |
| 5 | 525 μM |
| 6 | 384 μM |
| 7 | 62 μM |
| 9 | 14 μM |
| 11 | 75 μM |
| 13 | 50 nM |
| 20 | 120 nM |
| 24 | 5 μM |
| 25 | 12 μM |
| 28 | 5 μM |
| 35 | 25 nM |
| 36 | 20 nM |
| 37 | 170 nM |
| 39 | 28 μM |

Embodiment 44: In-Vivo Inhibition Effect of Modified Derivative of Cordycepin on Zebrafish Suffering from Small Cell Lung Cancer Models of zebrafish bearing transplanted tumors of small cell lung cancers of H69, H446 and H1048 cells were respectively established: $1\times10^6$ mL suspensions of the H69, H446 and H1048 cells were respectively prepared and placed in a serum-free cell culture medium, 5 mL of red fluorescent dye (CM-DiI) cell labeling solution was added into each milliliter of cell suspension, mixed gently and evenly, incubated at 37° C. for 20 minutes, centrifuged at 1,500 rpm for 5 minutes to remove a supernatant, and added with the serum-free culture medium again for resuspension, and then the above steps were repeated twice to obtain a cell suspension to be labeled. The cell suspension was transplanted into yolk sacs of the zebrafish by micro-injection, each zebrafish was transplanted with about 100 cells, a transplanted tumor model of a zebrafish-human small cell lung cancer sensitive strain was established, and the zebrafish injected with ovarian cancer cells were cultured to be 3 dpf at 35° C.

Figure 2:
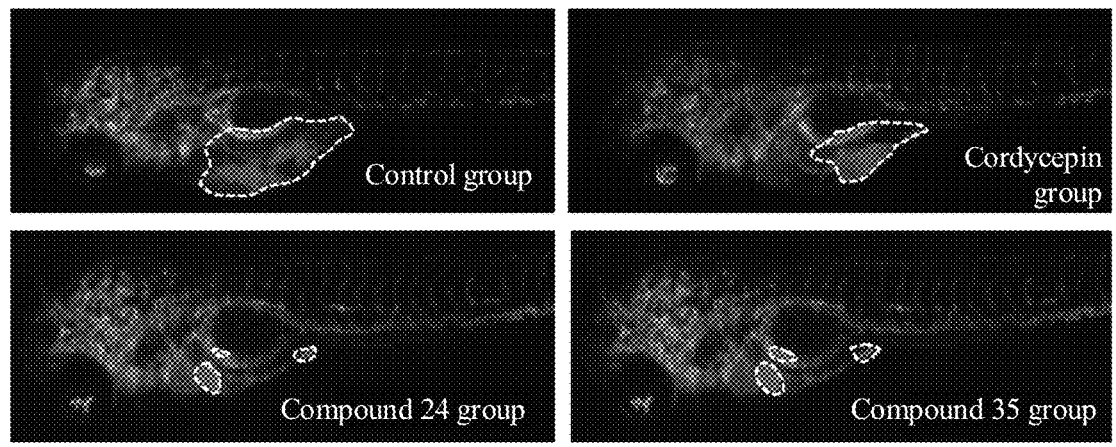
FIG. 2 shows inhibition effects of a control group and various compound groups on a tumor-bearing zebrafish model of small cell lung cancer H446 cells.

Value-added effects of the cordycepin and the prepared compounds 2, 5, 6, 7, 9, 11, 13, 20, 24, 25, 28, 35, 36, 37 and 39 on anti-small cell lung cancer of the zebrafish in vivo were tested: when the tumor-bearing zebrafish model was inhibited to be 3 dpf, the zebrafish with good consistency in transplanted tumor were selected under a microscope, and randomly distributed into a 6-well plate, with 30 zebrafish in each well. In the case of 3 dpf, the above compounds were diluted according to the MTD dose, dissolved in DMSO and added into each well. Meanwhile, a normal control group, a model control group and a solvent control group (DMSO) were set, with 3 mL of fish culture water in each well. After the zebrafish in each experimental group were continuously cultured at 35° C. to be 5 dpf, 10 zebrafish in each experimental group were randomly selected, observed under a fluorescence microscope, and photographed, images were saved, and analyzed by Nikon NIS-Elements l3.10 advanced image processing software, and fluorescence intensities (S) of transplanted tumors of the zebrafish were calculated. Inhibition results were shown in Table 3 below, wherein inhibition results of the control group, the cordycepin group, the compound 24 and compound 35 groups on H446 small cell lung cancer-transplanted zebrafish were as shown in FIG. 2. Growth inhibition effects of a Xiaoaiping injection and paclitaxel applied alone on a zebrafish-human ovarian cancer sensitive strain were calculated by overall fluorescence intensity according to a formula as follows:

Tumor growth inhibition effect (%)=S(model control group)−S(drug group)/S(model control group)×100%

TABLE 3

Effects of various compounds on proliferation of three cell lines in zebrafish model

| Compound number | H69 M ± SEM (%) | H446 M ± SEM (%) | H1048 M ± SEM (%) |
|---|---|---|---|
| Cordycepin (995 μM) | 57.53 ± 11.08 | 61.19 ± 7.62 | 60.32 ± 4.95 |
| 2 (845 μM) | 63.93 ± 5.37 | 65.42 ± 7.45 | 65.74 ± 4.41 |
| 5 (125 μM) | 67.70 ± 6.97 | 75.02 ± 9.54 | 76.72 ± 4.55 |
| 6 (384 μM) | 64.20 ± 3.23 | 67.04 ± 4.75 | 71.43 ± 4.78 |
| 7 (62 μM) | 68.41 ± 4.22 | 71.30 ± 4.27 | 67.34 ± 4.07 |
| 9 (14 μM) | 70.32 ± 6.84 | 76.53 ± 10.43 | 74.89 ± 10.52 |
| 11 (75 μM) | 79.06 ± 7.43 | 74.37 ± 4.39 | 87.67 ± 6.12 |
| 13 (50 nM) | 64.09 ± 1.23 | 66.64 ± 4.43 | 68.74 ± 5.05 |
| 20 (120 nM) | 70.41 ± 2.34 | 68.76 ± 3.52 | 70.16 ± 3.14 |
| 24 (5 μM) | 68.62 ± 4.79 | 84.92 ± 2.69 | 83.41 ± 5.83 |
| 25 (12 μM) | 68.74 ± 3.47 | 66.41 ± 3.59 | 70.15 ± 4.08 |
| 28 (5 μM) | 83.55 ± 4.59 | 76.46 ± 8.03 | 99.61 ± 8.81 |
| 35 (25 nM) | 69.55 ± 6.28 | 79.06 ± 2.28 | 81.91 ± 6.37 |
| 36 (20 nM) | 78.36 ± 4.59 | 76.07 ± 4.16 | 78.37 ± 4.75 |
| 37 (170 nM) | 72.24 ± 2.49 | 71.74 ± 3.18 | 73.48 ± 3.87 |
| 39 (28 μM) | 64.17 ± 3.16 | 65.65 ± 4.07 | 68.52 ± 4.14 |

Figure 3:
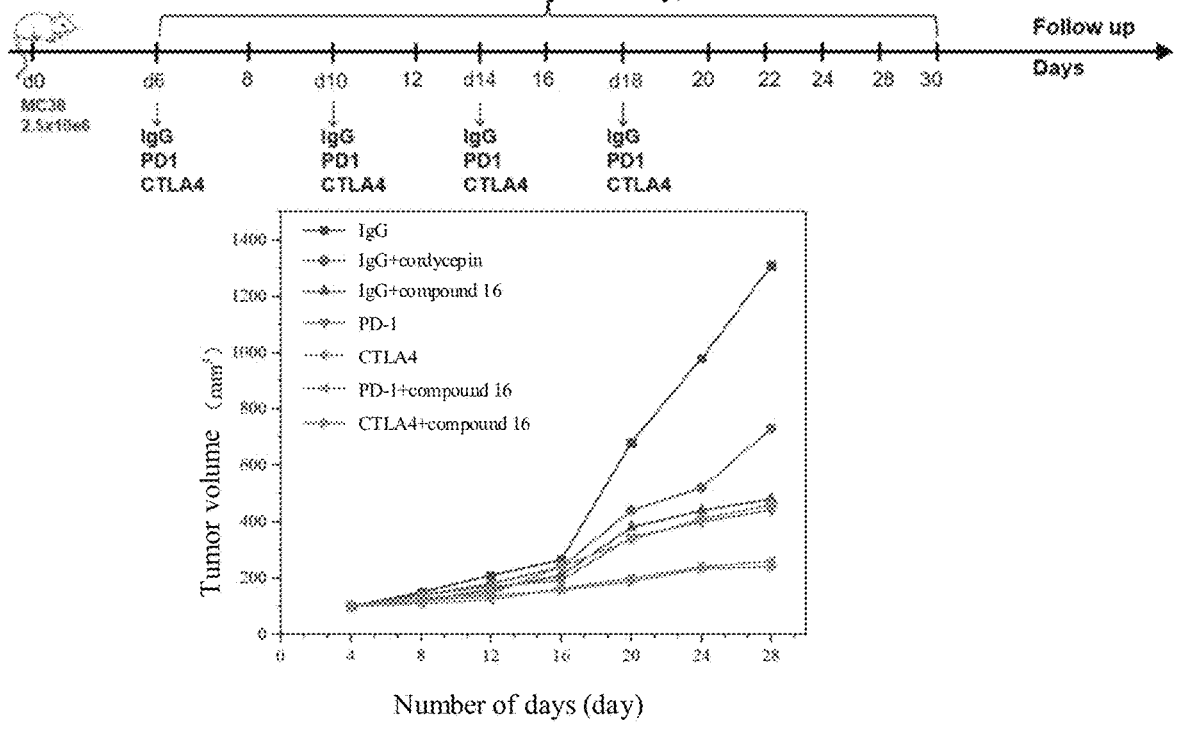
FIG. 3 shows inhibition effects of a compound 16 and an immune checkpoint inhibitor on a mouse model transplanted with colon cancer MC38 cells.

Embodiment 45: Inhibition Experiment Effect of Modified Derivative of Cordycepin on Colon Cancer A mouse transplanted colon cancer model was established and a drug was evaluated. $2.5\times10^6$ MC-38 colon cancer cells were suspended in 100 μL of PBS to be inoculated into an outer side of thigh of left lower limb of C57BL/6j nude mice. One week later, when the transplanted tumor reached about 100 mm$^3$, the mice were randomly divided into seven groups, with 8 mice in each group, comprising a control group IgG, a compound 16 drug+IgG group, a PD-1 antibody treatment group, a CTLA4 monoclonal antibody treatment group, a compound 16 drug+PD-1 combined treatment group and a compound 16 drug+CTLA4 monoclonal antibody combined treatment group respectively. The control group IgG was intragastrically administrated with immunoglobulin G (IgG) (500 ug/time/animal) every day for 28 consecutive days. The cordycepin+IgG was intragastrically administrated with the immunoglobulin G (IgG) and the cordycepin (500 ug/time/animal in both cases) every day for 28 consecutive days. The compound 16 drug+IgG group was intragastrically administrated with the immunoglobulin G (IgG) and a compound 16 drug (500 ug/time/animal in both cases) every day for 28 consecutive days. The antibody treatment group was intragastrically administrated with an antibody (500 ug/time/animal) every 4 days for 28 consecutive days. The compound 16 drug+antibody combined treatment group was intragastrically administrated an immunoglobulin compound 16 drug (500 ug/time/animal) every day, and intragastrically administrated the antibody (500 ug/time/animal) every 4 days for 28 consecutive days. The mice were killed after the experiment, blood and corresponding tissue samples were collected, tumor bodies were immediately photographed and weighed, and some tumor tissues were fixed in a formalin solution to be further detected. Two vertical diameters (length and width) of the transplanted tumor were measured with a caliper every two days to calculate a size of the transplanted tumor, and a tumor value was calculated according to a formula: tumor volume (mm$^3$)=½×(length×width)$^2$, and changes of tumor sizes of colon cancer in seven groups of mice were observed. Results were shown in FIG. 3. 28 days later, the experimental results show that the cordycepin has an anti-proliferation effect on the colon cancer (the size is reduced from 1,300 mm$^3$ to 730 mm$^3$), the compound 16 used alone has a more obvious anti-tumor growth effect than the cordycepin (the size is reduced from 1,300 mm$^3$ to 480 mm$^3$)(P<0.01), and immune checkpoint inhibitors PD-1 and CTLA4 used alone also have a significant anti-tumor growth effect (the size is reduced from 1,300 mm$^3$ to about 448 mm$^3$) (P<0.01). When the compound 16 and the immune checkpoint inhibitors PD-1 and CTLA4 are respectively used at the same time, a synergistic effect of them can greatly improve the anti-tumor effect (the size is reduced from 1,300 mm$^3$ to about 260 mm$^3$).

Figure 4:
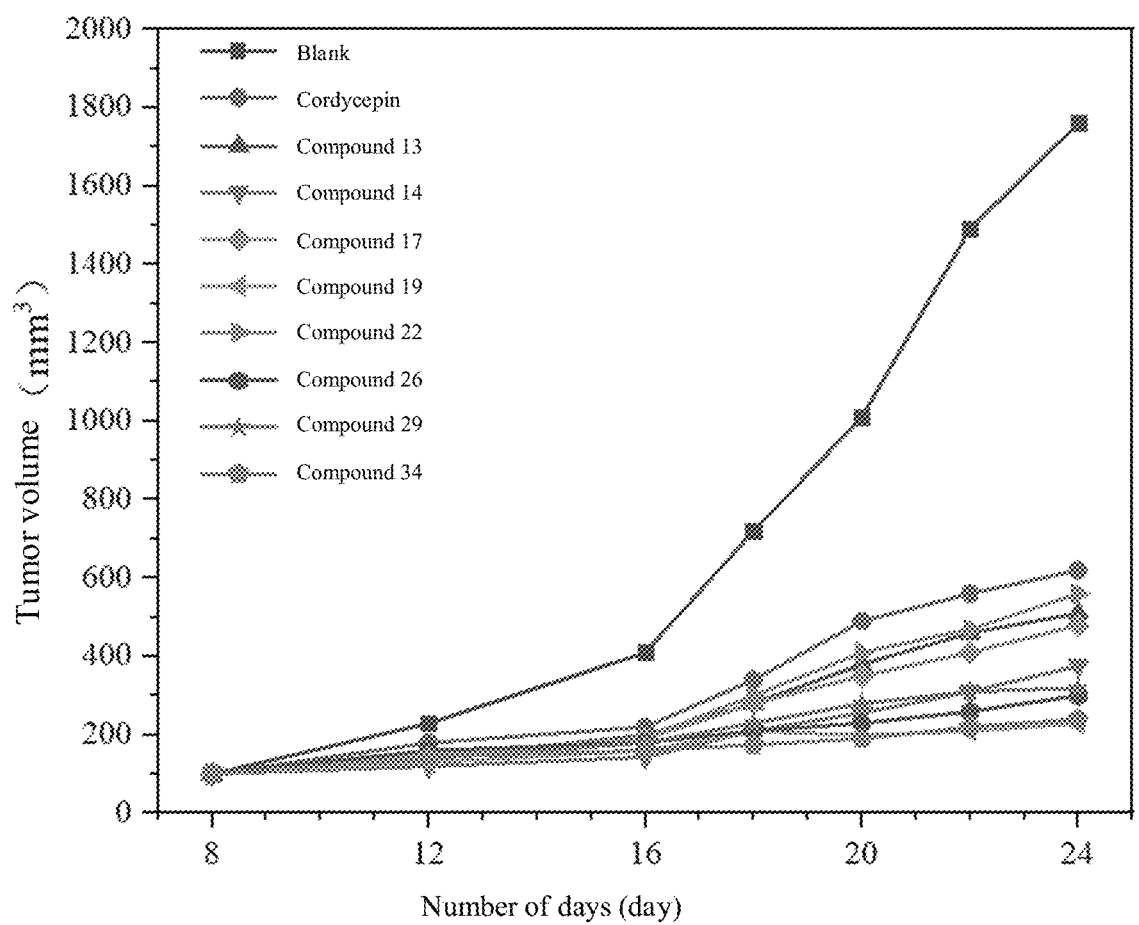
FIG. 4 shows anti-tumor effects of the control group and the compound group on a mouse model transplanted with melanoma B16-F10.

Embodiment 46: Inhibition Experiment Effect of Modified Derivative of Cordycepin on Melanoma A mouse transplanted melanoma model was established and a drug was evaluated. $2.5\times10^5$ B16-F10 melanoma cells were suspended in 100 μL of PBS to be inoculated into an outer side of thigh of left lower limb of C57BL/6j nude mice. One week later, when the transplanted tumor reached about 100 mm$^3$, the mice were randomly divided into ten groups, with 10 mice in each group, comprising a blank control group, a cordycepin group, a compound 13 group, a compound 14 group, a compound 17 group, a compound 19 group, a compound 22 group, a compound 26 group, a compound 29 group and a compound 34 group respectively. The blank control group was intragastrically administrated with a nutritional agent such as a corn steep liquor and DMSO as a solvent control every day for 24 consecutive days, and the compound groups were intragastrically administrated with corresponding compounds (500 ug/time/animal in all cases) every other day for 24 consecutive days. Changes of melanoma sizes in the ten groups of mice were observed every 4 days in an early stage and every two days in a late stage. The mice were killed after the experiment, blood and corresponding tissue samples were collected, tumor bodies were immediately photographed and weighed, and some tumor tissues were fixed in a formalin solution to be further detected. Two vertical diameters (length and width) of the transplanted tumor were measured with a caliper every two days to calculate a size of the transplanted tumor, and a tumor value was calculated according to a formula: tumor volume (mm$^3$)=½×(length×width)$^2$. Experimental results were shown in FIG. 4. The experimental results show that the cordycepin itself can inhibit the proliferation of melanoma (reduced from 1760 mm$^3$ to 600 mm$^3$), and the modified derivative of the cordycepin has a better effect than the cordycepin (reduced from 1760 mm$^3$ to <560 mm$^3$), wherein the compounds 19 and 34 used alone can obviously inhibit the tumor growth of the mice (reduced from 1760 mm$^3$ to about 240 mm$^3$) P<0.001). The above results suggest that the synthesized product has the effect of killing tumor cells.

Embodiment 46-1: A Compound 27 was Used to Inhibit Melanoma by the Above Method, which had the Same Inhibition Effect as a Compound 26

Embodiment 47: Inhibition Experiment Effect of Modified Derivative of Cordycepin on Ovarian Cancer A mouse transplanted ovarian cancer model was established and a drug was evaluated. $2.5\times10^6$ IDB ovarian cancer cells were suspended in 100 μL of PBS to be inoculated into an outer side of thigh of left lower limb of C57BL/6j nude mice. About one week later, when the transplanted tumor reached about 100 mm$^3$, the mice were randomly divided into five groups, with 10 mice in each group, comprising a control group, a cordycepin group, a compound 24 drug group, a PD-1+TIM3 antibody treatment group, a compound 24 drug+PD-1+TIM3 antibody treatment group respectively. The control group was intragastrically administrated with immunoglobulin G (IgG) (500 ug/time/animal) every day for 15 consecutive days. The cordycepin group was intragastrically administrated with the cordycepin (500 ug/time/animal) every day under configuration with PBS for 15 consecutive days. The compound 24 drug group was intragastrically administrated with the compound 24 (500 ug/time/animal) every day under configuration with PBS for 15 consecutive days. The PD-1+TIM3 antibody treatment group was intragastrically administrated with antibody PD-1+TIM3 (500 ug/time/animal respectively) every 4 days for 15 consecutive days. The compound 24 drug+PD-1+TIM3 antibody treatment group was intragastrically administrated an immunoglobulin compound 24 drug (500 ug/time/animal) every day, and intragastrically administrated the antibody PD-1+TIM3 (500 ug/time/animal respectively) every 4 days for 15 consecutive days.

Figure 5:
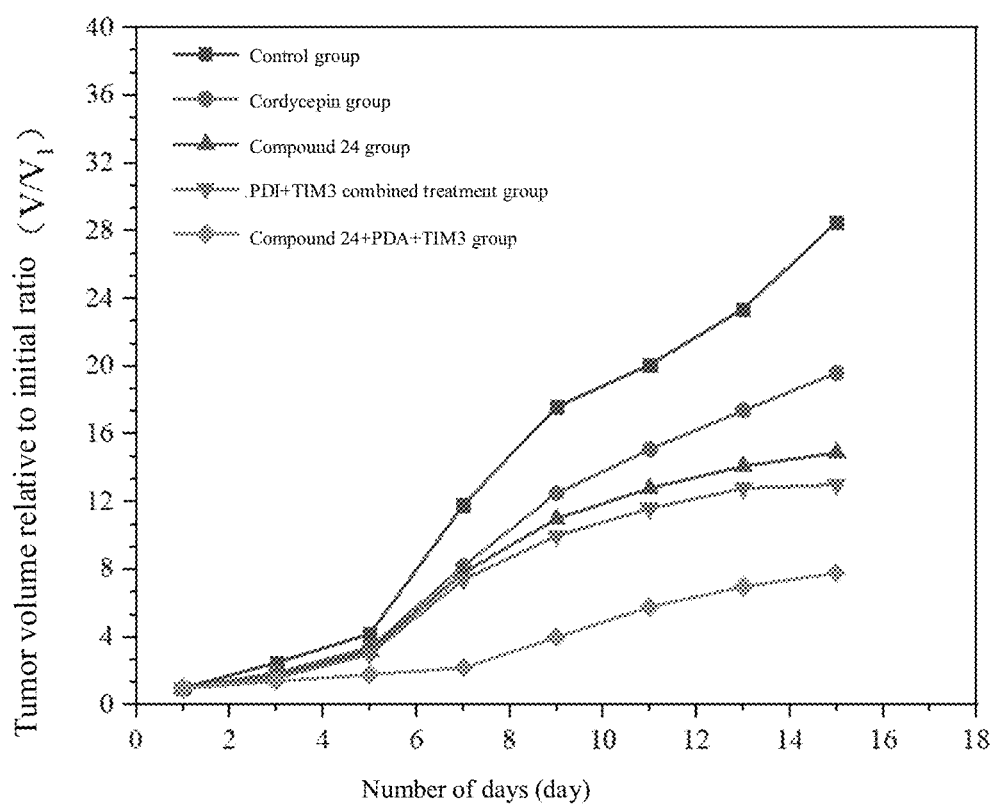
FIG. 5 shows inhibition effects of a compound 24 and the immune checkpoint inhibitor on a homotransplanted tumor model of a mouse with an ID8 ovarian cancer.

Changes of sizes of ovarian tumors in five groups of mice were observed every two days. The mice were killed after the experiment, blood and corresponding tissue samples were collected, tumor bodies were immediately photographed and weighed, and some tumor tissues were fixed in a formalin solution to be further detected. Two vertical diameters (length and width) of the transplanted tumor were measured with a caliper every two days to calculate a size of the transplanted tumor, and a tumor value was calculated according to a formula: tumor volume $(mm^3)=½×(length× width)^2$, Results were shown in FIG. 5. The experimental results show that the cordycepin has an anti-proliferation effect on the ovarian cancer (the size is reduced by 1.5 times in 15 days), the compound 24 used alone has a more obvious anti-tumor growth effect than the cordycepin (the size is reduced by about 2 times in 15 days), and immune checkpoint inhibitors PD-1 and CTLA4 used alone also have a significant anti-tumor growth effect (the size is reduced by more than 2 times in 15 days). When the compound 24 and the immune checkpoint inhibitors PD-1 and CTLA4 are respectively used at the same time, the anti-tumor effect can be greatly improved (the size is reduced by about 4 times in 15 days).

Embodiment 48: Inhibition Experiment Effect of Modified Derivative of Cordycepin on In-Vitro-Gastric Cancer Cells Anti-tumor dose-effect relationship curves of the cordycepin and 40 compounds prepared in gastric cancer cell lines AGS and BGC-823 were analyzed by an MTT experimental method. Calculation results of median inhibitory concentration ($IC_{50}$) were summarized as shown in Table 4 below. Results of an in-vitro anti-tumor experiments show that, compared with the cordycepin, an effective concentration of a modified cordycepin derivative on tumor cells is reduced.

TABLE 4

$IC_{50}$ (μM) of cordycepin and modified compounds of cordycepin in gastric cancer cells

| Compound | AGS | BGC-823 |
|---|---|---|
| Cordycepin | 372 | 235 |
| 1 | 81.67 | 64.41 |
| 2 | 142 | 209 |
| 3 | 86.72 | 61.39 |
| 4 | 64.33 | 86.16 |
| 5 | 72.74 | 91.48 |
| 6 | 66.77 | 73.16 |
| 7 | 2.46 | 1.61 |
| 8 | 27.78 | 18.82 |
| 9 | 0.46 | 1.24 |
| 10 | 136 | 82.41 |
| 11 | 13.03 | 10.31 |
| 12 | 1.23 | 1.34 |
| 13 | 32.45 | 36.75 |
| 14 | 12.87 | 18.57 |
| 15 | 18.43 | 20.72 |
| 16 | 0.14 | 0.19 |
| 17 | 1.32 | 2.39 |
| 18 | 0.41 | 0.69 |
| 19 | 0.46 | 0.76 |
| 20 | 0.94 | 1.37 |
| 21 | 2.46 | 4.38 |
| 22 | 45.04 | 53.73 |
| 23 | 0.89 | 1.31 |
| 24 | 0.13 | 0.09 |
| 25 | 47.56 | 58.47 |
| 26 | 57.41 | 46.58 |
| 27 | 8.42 | 10.17 |
| 28 | 3.47 | 5.42 |
| 29 | 32.48 | 41.39 |
| 30 | 75.42 | 64.17 |
| 31 | 41.25 | 33.64 |
| 32 | 23.04 | 19.82 |
| 33 | 36.47 | 29.51 |
| 34 | 19.37 | 24.16 |
| 35 | 69.42 | 71.03 |
| 36 | 103 | 90.24 |
| 37 | 64.23 | 56.11 |
| 38 | 134 | 104 |
| 39 | 187 | 167 |
| 40 | 164 | 189 |

Figure 6:
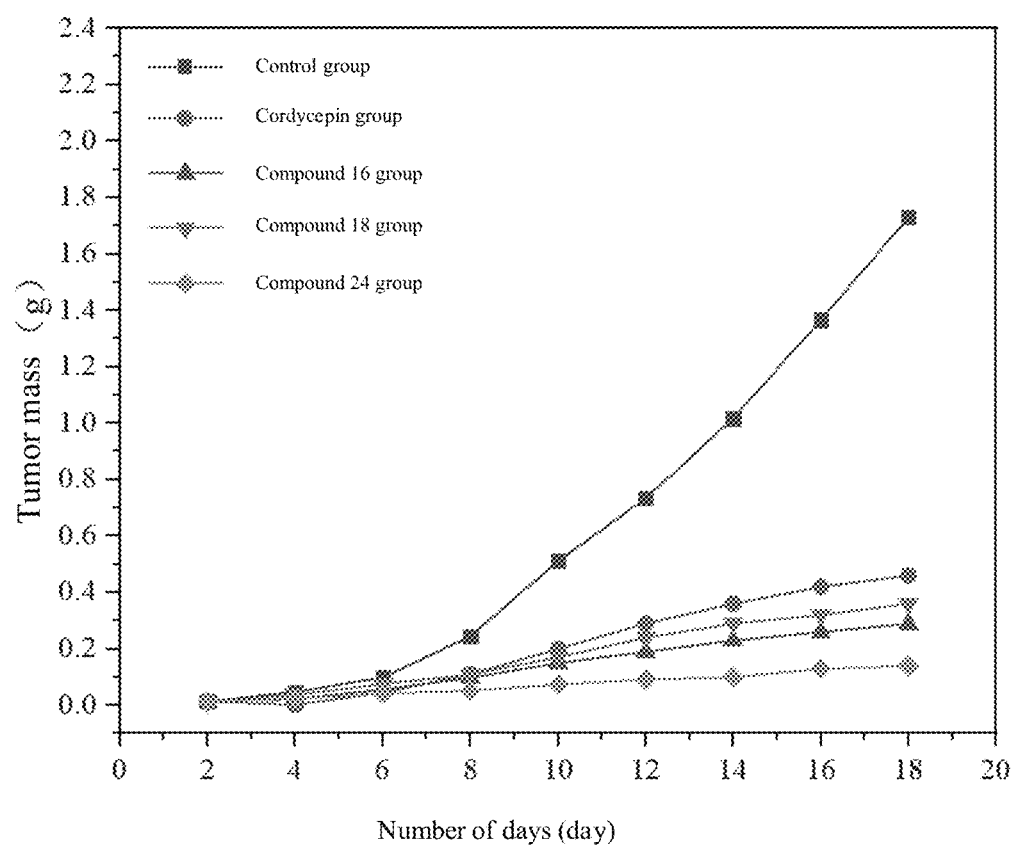
FIG. 6 shows anti-tumor effects of the control group and the compound group on a mouse model transplanted with gastric cancer BGC-823 cells.

Embodiment 49: In-Vivo Tumor Inhibition Experimental Effect of Modified Derivative of Cordycepin on Gastric Cancer-Mouse Model A mouse transplanted gastric cancer model was established and a drug was evaluated. $2×10^7$ BGC-823 gastric cancer cells were suspended in 100 μL of PBS to be inoculated into an anterior chest wall of C57BL/6j nude mice, disinfection was carried out with 75% ethanol, and the most obvious part of apical impulse was touched with hand to inoculate the cells to a left ventricle in a second intercostal space about 3 mm to the left of the sternum. About one week later, when the transplanted tumor reached about 100 $mm^3$, the mice were randomly divided into five groups, with 10 mice in each group, comprising a control group, a cordycepin group, and compound 16, compound 18 and compound 24 drug groups respectively. The control group was intragastrically administered with a nutritional agent such as a corn steep liquor and DMSO as a solvent control every day; the cordycepin group was intragastrically administered with the cordycepin (500 ug/time/animal) every day under configuration with DMSO; and the compound drug groups were intragastrically administered with the compounds (500 ug/time/animal) every day under configuration with DMSO. The administration was carried out for 18 consecutive days. Changes of gastric tumor sizes in the five groups of mice were observed every two days, the mice were killed after the experiment, blood and corresponding tissue samples were collected, and tumor bodies were immediately photographed and weighed. Weighing experimental results were shown in FIG. 6. It can be seen from the experimental results that the cordycepin can effectively inhibit the proliferation of gastric tumors, which is about 4 times lower than that of the control group (reduced from 1.73 g to 0.46 g), and the modified cordycepin has a more obvious effect than the cordycepin, wherein the compound 24 group is about 12 times lower than that of the control group (reduced from 1.73 g to 0.14 g).

Figure 7:
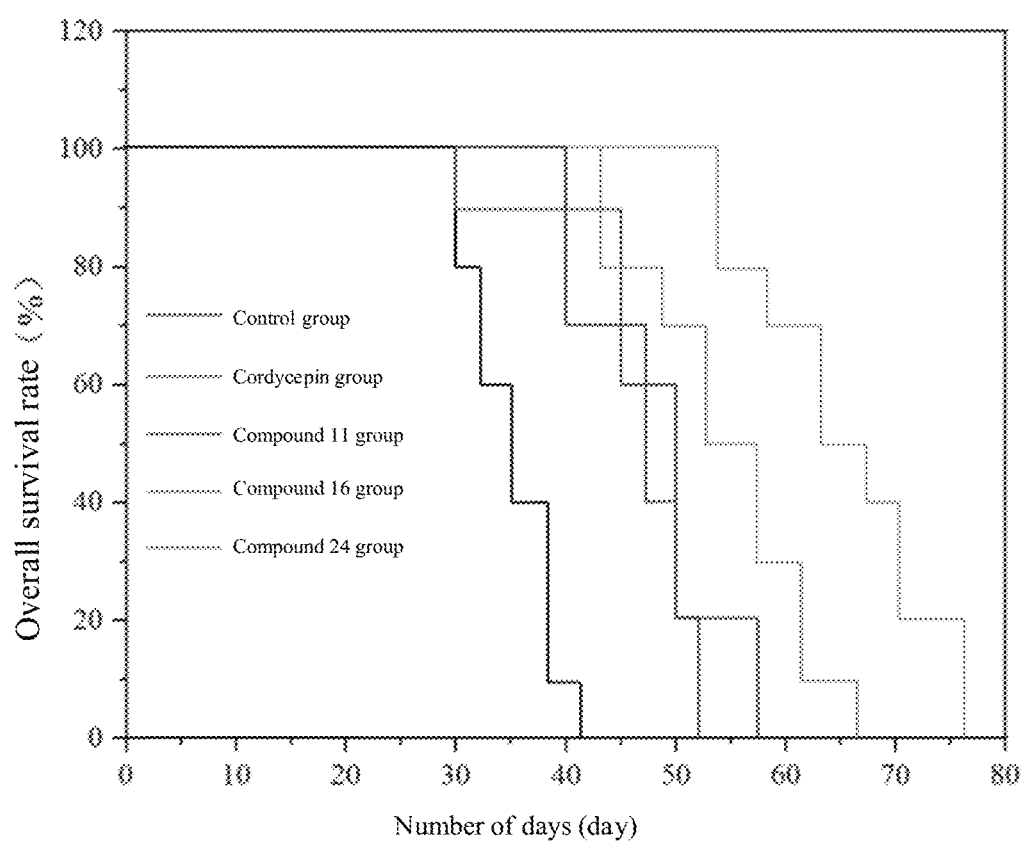
FIG. 7 shows anti-tumor effects of the control group and the compound group on a mouse model transplanted with pancreatic cancer Pan02-luc cells.

Embodiment 50: In-Vivo Tumor Inhibition Experimental Effect of Modified Derivative of Cordycepin on Pancreatic Cancer-Mouse Model A mouse transplanted pancreatic cancer model was established and a drug was evaluated: pancreatic cancer Pan02-luc cells were placed in a DMEM culture medium containing 10% fetal bovine serum in a $CO_2$ incubator at 37° C. Trypsin ED-TA was subjected to digestive passage, and was passaged every 2 days to 3 days. When a number of the cells reached a required number, the cells in logarithmic growth period were resuspended with the culture medium to be $1\times10^7$/mL. C57BL/6j nude mice were fed under a pathogen-free condition, and when the mice grew to 6 weeks, 200 uL of pancreatic cancer Pan02-uc cells were subcutaneously injected into a right dorsal axil of each mouse, and a transplanted tumor appeared within about one week, indicating that the model was established successfully. The mice were randomly divided into five groups, with 10 mice in each group, comprising a control group, a cordycepin group, and compound 11, compound 16 and compound 24 drug groups respectively. The control group was intragastrically administrated with a nutritional agent such as a corn steep liquor and DMSO as a solvent control every day; the cordycepin group was intragastrically administrated with the cordycepin (500 ug/time/animal) every day under configuration with DMSO; and the compound drug groups were intragastrically administrated with the compounds (500 ug/time/animal) every day under configuration with DMSO. The administration was continuously performed for 24 days. Subsequently, survival rates of the five groups of mice were observed every day, and median survival time was studied. Experimental results were shown in FIG. 7. The experimental results show that the cordycepin administrated alone has significantly prolonged the survival time of the tumor-bearing mice (increased from 41 days to 52 days), and the compound groups further prolong the survival time of the tumor-bearing mice (increased from 41 days to >58 days), wherein the compound 24 has the best effect, which prolongs the survival time of the tumor-bearing mice by nearly half (increased from 41 days to 76 days).

The above is only the preferred embodiments of the present invention, and it should be pointed out that those of ordinary skills in the art may further make several improvements and decorations without departing from the principle of the present invention, and these improvements and decorations should also be regarded as falling within the scope of protection of the present invention. All the unspecified components in the embodiments can be realized by the prior art.

What is claimed is:

1. A cordycepin derivative is compound 24

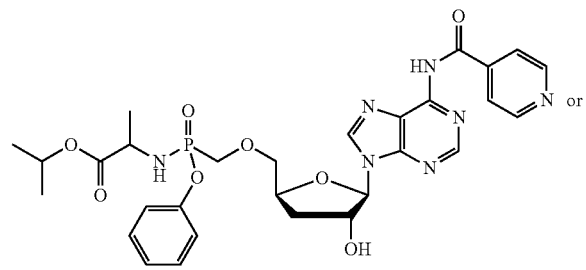

or compound 20

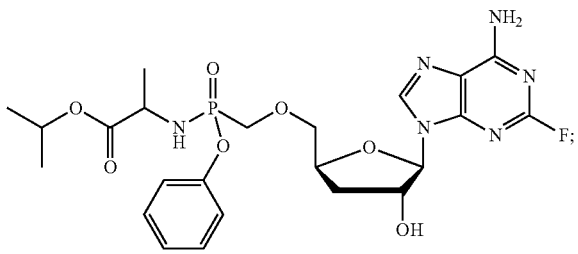

or a pharmaceutically acceptable salt thereof.

2. A pharmaceutical composition comprising at least one cordycepin derivative of claim 1, or the pharmaceutically acceptable salt thereof; and at least one immune checkpoint inhibitor.

3. The pharmaceutical composition according to claim 2, wherein the immune checkpoint inhibitor is selected from the group consisting of a PD-1 monoclonal antibody, CTLA4 monoclonal antibody, and a combination of the PD-1 monoclonal antibody and the CTLA4 monoclonal antibody.

4. The pharmaceutical composition according to claim 2, wherein a ratio of the cordycepin derivative: the immune checkpoint inhibitor is 1:0.2-5 by weight.

5. The pharmaceutical composition according to claim 4, wherein the ratio of the cordycepin derivative: the immune checkpoint inhibitor is 1:0.8-1.2 by weight.

6. The pharmaceutical composition according to claim 2, wherein the pharmaceutical composition is prepared as a tablet, a pill, a capsule, a syrup, an injection, a sustained to release agent, or a kit.

7. A method for preventing and treating a disease by administering the cordycepin derivative of claim 1, or the pharmaceutically acceptable salt thereof to a subject in need, wherein the disease is a tumor.

8. The method according to claim 6, wherein the tumor is selected from the group consisting of a gastric cancer, a pancreatic cancer, a liver cancer, a small cell lung cancer, a non-small cell lung cancer, a colorectal cancer, an esophageal cancer, a prostate cancer, melanoma, glioma, and an ovarian cancer.

* * * * *